US012673948B2

(12) United States Patent
Zhang et al.

(10) Patent No.: US 12,673,948 B2
(45) Date of Patent: Jul. 7, 2026

(54) SULFOXIMINE-CONTAINING ATR INHIBITOR COMPOUND

(71) Applicant: Chia Tai Tianqing Pharmaceutical Group Co., Ltd., Lianyungang City (CN)

(72) Inventors: Mnsheng Zhang, Nanjing City (CN); Yan Zhu, Nanjing City (CN); Baomin Liu, Nanjing City (CN); Kuo Gai, Nanjing City (CN); Shaowei Chen, Nanjing City (CN); Wei Shi, Nanjing City (CN)

(73) Assignee: CHIA TAI TIANQING PHARMACEUTICAL GROUP CO., LTD., Lianyungang (CN)

( * ) Notice: Subject to any disclaimer, the term of this patent is extended or adjusted under 35 U.S.C. 154(b) by 339 days.

(21) Appl. No.: 18/569,592

(22) PCT Filed: May 12, 2022

(86) PCT No.: PCT/CN2022/092494
§ 371 (c)(1),
(2) Date: Dec. 12, 2023

(87) PCT Pub. No.: WO2022/237875
PCT Pub. Date: Nov. 17, 2022

(65) Prior Publication Data

US 2025/0026750 A1 Jan. 23, 2025

(30) Foreign Application Priority Data

May 12, 2021 (CN) ........................ 202110517129.X

(51) Int. Cl.

| | |
|---|---|
| ***C07D 471/04*** | (2006.01) |
| ***A61K 31/5377*** | (2006.01) |
| ***A61K 31/541*** | (2006.01) |
| ***A61P 35/00*** | (2006.01) |
| ***C07D 519/00*** | (2006.01) |

(52) U.S. Cl.
CPC ........ *C07D 471/04* (2013.01); *A61K 31/5377* (2013.01); *A61K 31/541* (2013.01); *A61P 35/00* (2018.01); *C07D 519/00* (2013.01)

(58) Field of Classification Search
None
See application file for complete search history.

(56) References Cited

U.S. PATENT DOCUMENTS

2016/0287604 A1 10/2016 Aktiengesellschaft
2019/0016713 A1 1/2019 Di Francesco et al.

FOREIGN PATENT DOCUMENTS

| | | | | |
|---|---|---|---|---|
| CN | 102311448 A | 1/2012 | | |
| CN | 111484491 A | 8/2020 | | |
| JP | 2017523987 A | 8/2017 | | |
| WO | WO2013049722 A1 | 4/2013 | | |
| WO | WO2016020320 A1 | 2/2016 | | |
| WO | WO2019178590 A1 | 9/2019 | | |
| WO | WO2020020288 A1 | 1/2020 | | |
| WO | WO-2020087170 A1 * | 5/2020 | .............. | A61P 35/00 |
| WO | WO2020254831 A1 | 12/2020 | | |
| WO | WO2020259601 A1 | 12/2020 | | |
| WO | WO2021012049 A1 | 1/2021 | | |

OTHER PUBLICATIONS

First Office Action for the Eurasian patent Application No. 202392841, mailed on May 7, 2024.
English translation of the first Office Action for the Eurasian patent Application No. 202392841, mailed on May 7, 2024.
First Office Action issued on May 29, 2025 for counterpart Saudi Arabian patent application No. 523451431, along with the English translation.
Extended European Search Report issued on Aug. 5, 2025 for counterpart European patent application No. 22806837.5.
English translation of the International search report issued for patent application No. PCT/CN2022/092494 mailed on Aug. 10, 2022.
English translation of abstract from CN102311448A.
English translation of abstract from CN111484491A.

(Continued)

*Primary Examiner* — Bethany P Barham
(74) *Attorney, Agent, or Firm* — TOPE-MCKAY & ASSOCIATES

(57) ABSTRACT

A sulfoximine-containing ATR inhibitor compound as represented by formula (I), a preparation method therefor, a pharmaceutical composition containing same, and the use thereof in the treatment of ATR-related or ATR-mediated diseases and/or conditions.

(I)

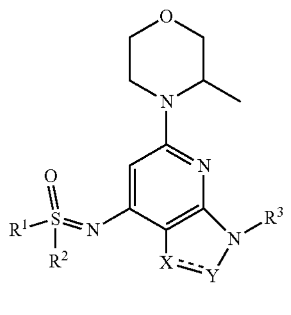

19 Claims, No Drawings

(56) References Cited

OTHER PUBLICATIONS

Peter G. M. Wuts, Theodora W. Greene, "Greene's Protective Groups in Organic Synthesis" (4th Ed), First published:Apr. 10, 2006, Hoboken, New Jersey: John Wiley & Sons, Inc., pp. 737-1028.

First Office Action issued for corresponding Japanese Patent Application 2023-568698, mailed on Feb. 10, 2026, and it's English translation.

First Office Action issued and search report for corresponding AE Patent Application P6002888/2023 mailed on Mar. 10, 2026, and it's English translation.

First Office Action issued on Apr. 2, 2026 for counterpart Taiwan patent application No. 111117801, and it's English translation.

Search report issued on Apr. 2, 2026 for counterpart Taiwan patent application No. 111117801, and it's English translation.

* cited by examiner

SULFOXIMINE-CONTAINING ATR INHIBITOR COMPOUND

TECHNICAL FIELD

The present application relates to a sulfoximine-containing ATR inhibitor compound, a preparation method therefor, a pharmaceutical composition comprising the compound, and use thereof in treating an ATR-related or ATR-mediated disease and/or disorder.

BACKGROUND

Ataxia telangiectasia mutated gene Rad3-related kinase (ATR) is a protein kinase that responds to cells with DNA damage. Upon activation, ATR can regulate, through a variety of signals, cellular life processes, including cell cycle arrest, inhibition of origins of replication, initiation of replication forks, and repair of DNA duplexes. ATR kinase works with ATM (ataxia-telangiectasia mutated) kinase and many other proteins to modulate cellular responses to DNA damage, commonly referred to as the DNA damage response (DDR). When DNA damage is recognized by a cell through DDR, it will immediately activate the DNA repair program and activate cell cycle checkpoints to arrest the normal cell cycle, thereby providing time for DNA repair. Without DDR, cells would be more susceptible to endogenous cell damage or to DNA damage arising from chemotherapy and radiotherapy for cancer treatment and would die more easily.

Many cancer cells have defects in the DNA repair pathway, showing great dependence on the remaining intact DNA repair proteins, including ATR. ATR is a key member of DDR that responds to damaged DNA replication. It is critical for maintaining genomic stability and integrity and promoting cell survival. Many cancer cells rely more on the ATR pathway than normal cells to regulate cellular DNA damage repair to promote cell survival, which makes ATR a promising target for cancer treatment. Therefore, ATR inhibitors have potential therapeutic effects on such tumor cells.

There has been no ATR inhibitor on the market. The research and development of safer and more effective ATR inhibitors is of great significance.

SUMMARY

In one aspect, the present application provides a compound of formula (I), a stereoisomer thereof or a pharmaceutically acceptable salt thereof, (I)

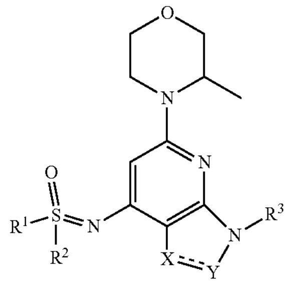

wherein

- ------ is a double bond, X is selected from $CR^a$, and Y is selected from N; or, ------ is a single bond, X is selected from C═O, and Y is selected from $NR^b$;

- $R^a$ is selected from the group consisting of hydrogen, hydroxy, cyano, halogen, $C_{1-6}$ alkyl, $C_{1-6}$ alkoxy, $C_{1-6}$ alkylamino, $C_{3-10}$ cycloalkyl, 3-10 membered heterocycloalkyl and $C_{3-10}$ cycloalkyl-$C_{2-6}$ alkynyl, wherein the $C_{1-6}$ alkyl, $C_{1-6}$ alkoxy, $C_{1-6}$ alkylamino, $C_{3-10}$ cycloalkyl, 3-10 membered heterocycloalkyl and $C_{3-10}$ cycloalkyl-$C_{2-6}$ alkynyl are optionally substituted with one or more halogen, hydroxy or cyano substituents;
- $R^b$ is selected from the group consisting of hydrogen and $C_{1-6}$ alkyl;
- $R^1$ and $R^2$ are each independently selected from the group consisting of $C_{1-10}$ alkyl, $C_{3-10}$ cycloalkyl, 3-10 membered heterocycloalkyl, $C_{6-10}$ membered aryl and 5-10 membered heteroaryl, wherein the $C_{3-10}$ cycloalkyl, 3-10 membered heterocycloalkyl, $C_{6-10}$ membered aryl and 5-10 membered heteroaryl are optionally substituted with one or more $R^c$;
- or $R^1$ and $R^2$, together with the sulfur atom to which they are attached, form 3-10 membered heterocyclyl, and the 3-10 membered heterocyclyl is optionally substituted with one or more $R^d$;
- $R^c$ and $R^d$ are each independently selected from the group consisting of halogen, hydroxy, amino, $C_{1-6}$ alkyl, $C_{1-6}$ alkoxy, $C_{1-6}$ alkyl-C(O)—, $C_{1-6}$ alkyl-S(O)$_2$—, $C_{3-10}$ cycloalkyl, 3-10 membered heterocycloalkyl, $C_{6-10}$ membered aryl and 5-10 membered heteroaryl;
- $R^3$ is selected from 5-10 membered heteroaryl optionally substituted with one or more $R^e$;
- $R^e$ is selected from the group consisting of hydroxy, amino, halogen, $C_{1-6}$ alkyl, $C_{1-3}$ haloalkyl, $C_{3-6}$ cycloalkyl and 3-6 membered heterocycloalkyl.

In some embodiments, $R^a$ is selected from the group consisting of hydrogen, halogen, $C_{1-6}$ alkyl, $C_{1-6}$ alkoxy, $C_{3-10}$ cycloalkyl and $C_{3-10}$ cycloalkyl-$C_{2-6}$ alkynyl, wherein the $C_{1-6}$ alkyl, $C_{1-6}$ alkoxy, $C_{3-10}$ cycloalkyl and $C_{3-10}$ cycloalkyl-$C_{2-6}$ alkynyl are optionally substituted with one or more halogens.

In some embodiments, $R^a$ is selected from the group consisting of hydrogen, hydroxy, halogen and $C_{1-6}$ alkyl, wherein the $C_{1-6}$ alkyl is optionally substituted with one or more halogens. In some embodiments, $R^a$ is selected from the group consisting of hydrogen, hydroxy, halogen and $C_{1-3}$ alkyl, wherein the $C_{1-3}$ alkyl is optionally substituted with one or more halogens.

In some embodiments, $R^a$ is selected from the group consisting of hydrogen, halogen, $C_{1-4}$ alkyl, $C_{1-4}$ alkoxy, $C_{3-6}$ cycloalkyl and $C_{3-6}$ cycloalkyl-$C_{2-4}$ alkynyl, wherein the $C_{1-4}$ alkyl, $C_{1-4}$ alkoxy, $C_{3-6}$ cycloalkyl and $C_{3-6}$ cycloalkyl-$C_{2-4}$ alkynyl are optionally substituted with one or more halogens.

In some embodiments, $R^a$ is selected from the group consisting of hydrogen, fluorine, chlorine, bromine, iodine, methyl, ethyl, n-propyl, isopropyl, n-butyl, isobutyl, tert-butyl, methoxy, ethoxy, n-propoxy, isopropoxy, cyclopropyl, cyclobutyl, cyclopentyl, cyclohexyl, cyclopropylethynyl and cyclopropylpropynyl, wherein the methyl, ethyl, n-propyl, isopropyl, n-butyl, isobutyl, tert-butyl, methoxy, ethoxy, n-propoxy, isopropoxy, cyclopropyl, cyclobutyl, cyclopentyl, cyclohexyl, cyclopropylethynyl and cyclopropylpropynyl are optionally substituted with one or more halogens. In some embodiments, $R^a$ is selected from the group consisting of hydrogen, bromine, methyl, n-propyl, isobutyl, tert-butyl, methoxy, cyclopropyl and cyclopropylethynyl, wherein the methyl, n-propyl, isobutyl, tert-butyl, methoxy, cyclopropyl and cyclopropylethynyl are optionally substituted with one or more halogens.

In some embodiments, $R^a$ is selected from the group consisting of hydrogen, bromine, methyl, trifluoromethyl, 3,3,3-trifluoropropyl, isobutyl, tert-butyl, difluoromethoxy, cyclopropyl and cyclopropylethynyl.

In some embodiments, $R^a$ is selected from the group consisting of hydrogen and halogen.

In some embodiments, $R^a$ is selected from the group consisting of hydrogen, fluorine, chlorine and bromine.

In some embodiments, $R^a$ is selected from the group consisting of hydrogen and bromine.

In some embodiments, $R^b$ is selected from the group consisting of hydrogen and $C_{1-3}$ alkyl. In some embodiments, $R^b$ is selected from hydrogen.

In some embodiments, ------ is a double bond, X is selected from $CR^a$, and Y is selected from N.

In some embodiments, ------ is a single bond, X is selected from C═O, and Y is selected from $NR^b$.

In some embodiments, ------ is a double bond, X is selected from the group consisting of CH and CBr, and Y is selected from N. In some embodiments, ------ is a single bond, X is selected from C═O, and Y is selected from NH.

In some embodiments, $R^1$ and $R^2$ are each independently selected from the group consisting of $C_{1-6}$ alkyl, $C_{3-8}$ cycloalkyl, 3-8 membered heterocycloalkyl, phenyl and 5-6 membered heteroaryl, wherein the $C_{3-8}$ cycloalkyl, 3-8 membered heterocycloalkyl, phenyl and 5-6 membered heteroaryl are optionally substituted with one or more $R^c$.

In some embodiments, $R^1$ and $R^2$ are each independently selected from the group consisting of $C_{1-4}$ alkyl, $C_{3-6}$ cycloalkyl, 3-6 membered heterocycloalkyl, phenyl and 5-6 membered heteroaryl, wherein the $C_{3-6}$ cycloalkyl, 3-6 membered heterocycloalkyl, phenyl and 5-6 membered heteroaryl are optionally substituted with one or more $R^c$.

In some embodiments, $R^1$ and $R^2$ are each independently selected from the group consisting of methyl, ethyl, n-propyl, isopropyl, n-butyl, isobutyl, tert-butyl, cyclopropyl, cyclobutyl, cyclopentyl, cyclohexyl, phenyl, pyrrolyl, thienyl, pyridinyl, pyrimidinyl and furanyl, wherein the cyclopropyl, cyclopentyl, cyclohexyl, phenyl, pyrrolyl, thienyl, pyridinyl, pyrimidinyl and furanyl are optionally substituted with one or more $R^c$.

In some embodiments, $R^1$ and $R^2$ are each independently selected from the group consisting of methyl, ethyl, tert-butyl, cyclopropyl, cyclopentyl, cyclohexyl, phenyl and pyridinyl, wherein the cyclopropyl, cyclopentyl, cyclohexyl, phenyl and pyridinyl are optionally substituted with one or more $R^c$. In some embodiments, the structural unit

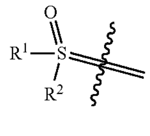

is selected from the group consisting of

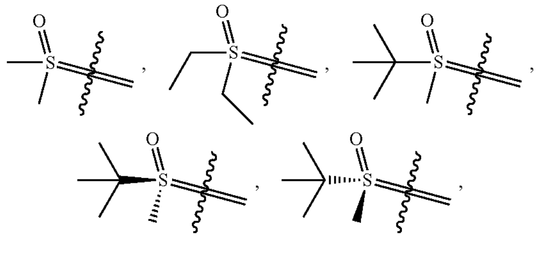

-continued

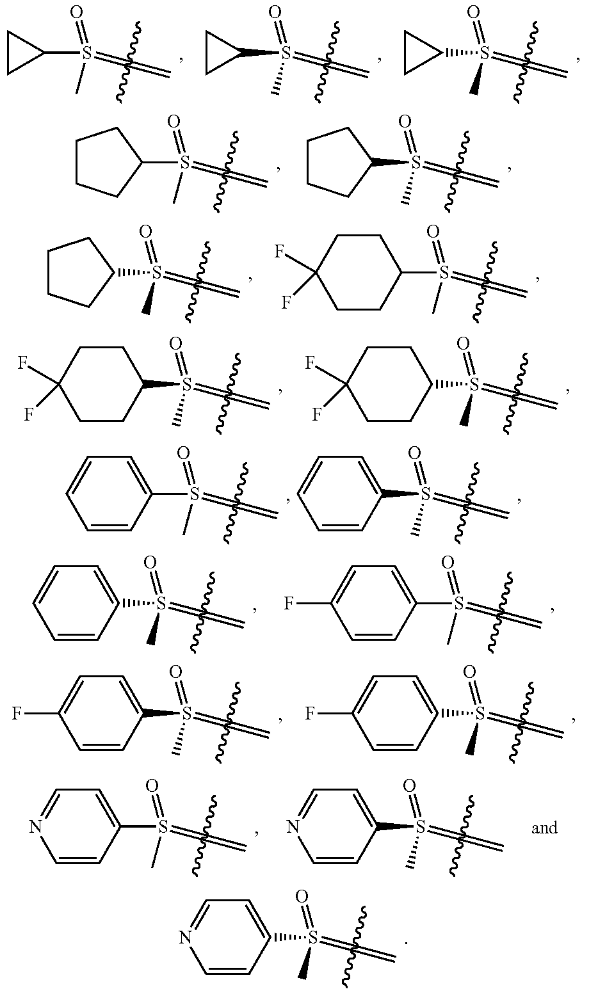

In some embodiments, $R^1$ and $R^2$ are each independently selected from the group consisting of $C_{1-3}$ alkyl, $C_{3-4}$ cycloalkyl, phenyl and 5-6 membered heteroaryl, wherein the $C_{3-4}$ cycloalkyl, phenyl and 5-6 membered heteroaryl are optionally substituted with one or more $R^c$.

In some embodiments, $R^1$ and $R^2$ are each independently selected from the group consisting of methyl, ethyl, cyclopropyl, phenyl and pyridinyl.

In some embodiments, the structural unit

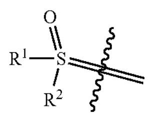

is selected from the group consisting of

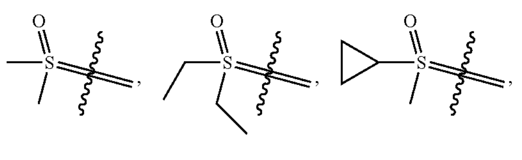

-continued

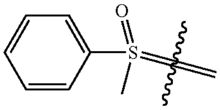

and

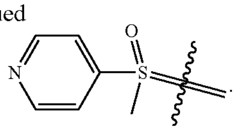

In some embodiments, $R^c$ and $R^d$ are each independently selected from the group consisting of halogen, hydroxy, amino, $C_{1-4}$ alkyl, $C_{1-4}$ alkoxy, $C_{1-4}$ alkyl-C(O)—, $C_{1-4}$ alkyl-$S(O)_2$—, $C_{3-8}$ cycloalkyl, 3-8 membered heterocycloalkyl, $C_{6-8}$ membered aryl and 5-8 membered heteroaryl.

In some embodiments, $R^c$ and $R^d$ are each independently selected from the group consisting of halogen, hydroxy, amino, $C_{1-3}$ alkyl, $C_{1-3}$ alkoxy, $C_{1-3}$ alkyl-C(O)—, $C_{1-3}$ alkyl-$S(O)_2$—, $C_{3-6}$ cycloalkyl, 3-6 membered heterocycloalkyl, phenyl and 5-6 membered heteroaryl.

In some embodiments, $R^c$ and $R^d$ are each independently selected from the group consisting of fluorine, chlorine, bromine, hydroxy, amino, methyl, ethyl, n-propyl, isopropyl, methoxy, ethoxy, n-propoxy, isopropoxy, $CH_3C(O)$—, $CH_3CH_2C(O)$—, $CH_3CH_2CH_2C(O)$—, $(CH_3)_2CH(O)$—, $CH_3S(O)_2$—, $CH_3CH_2S(O)_2$—, $CH_3CH_2CH_2S(O)_2$—, $(CH_3)_2CHS(O)_2$—, cyclopropyl, cyclopentyl, cyclohexyl, tetrahydrofuranyl, tetrahydropyrrolyl, piperazinyl, piperidinyl, phenyl, furanyl, pyrrolyl, thienyl, pyridinyl and pyrimidinyl.

In some embodiments, $R^c$ and $R^d$ are each independently selected from the group consisting of halogen, hydroxy, amino, $C_{1-4}$ alkyl and $C_{1-4}$ alkoxy. In some embodiments, $R^c$ and $R^d$ are each independently selected from the group consisting of halogen, hydroxy, amino, $C_{1-3}$ alkyl and $C_{1-3}$ alkoxy. In some embodiments, $R^c$ and $R^d$ are each independently selected from the group consisting of halogen and $C_{1-3}$ alkyl.

In some embodiments, $R^c$ is selected from the group consisting of halogen, hydroxy, amino, $C_{1-3}$ alkyl, $C_{1-3}$ alkoxy, $C_{1-3}$ alkyl-C(O)— and $C_{1-3}$ alkyl-$S(O)_2$—. In some embodiments, $R^c$ is selected from the group consisting of halogen, hydroxy and amino. In some embodiments, $R^c$ is selected from the group consisting of fluorine, chlorine and bromine. In some embodiments, $R^c$ is selected from bromine.

In some embodiments, $R^1$ and $R^2$, together with the sulfur atom to which they are attached, form 4-, 5-, 6-, 7-, 8-, 9- or 10-membered heterocycloalkyl, and the heterocycloalkyl is optionally substituted with one or more $R^d$.

In some embodiments, $R^1$ and $R^2$, together with the sulfur atom to which they are attached, form 4-6 membered mono heterocycloalkyl or 7-10 membered spiro heterocycloalkyl, and the mono heterocycloalkyl and spiro heterocycloalkyl are optionally substituted with one or more $R^d$.

In some embodiments, $R^1$ and $R^2$, together with the sulfur atom to which they are attached, form 4-, 5- or 6-membered mono heterocycloalkyl, or 7- or 9-membered spiro heterocycloalkyl, and the mono heterocycloalkyl and spiro heterocycloalkyl are optionally substituted with 1, 2 or 3 $R^d$. In some embodiments, $R^1$ and $R^2$, together with the sulfur atom to which they are attached, form

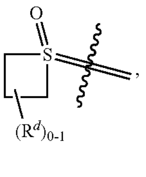

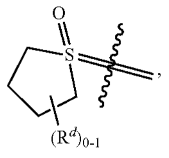

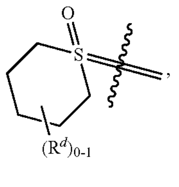

-continued

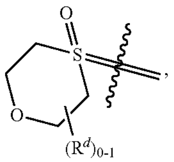

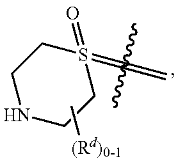

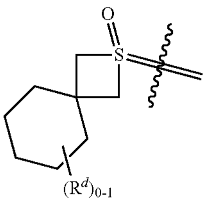

or

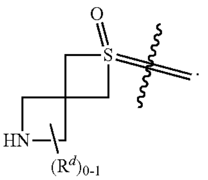

In some embodiments, $R^1$ and $R^2$, together with the sulfur atom to which they are attached, form

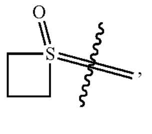

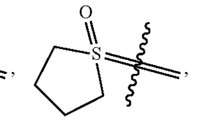

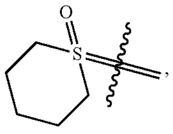

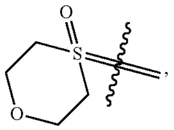

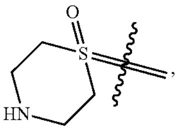

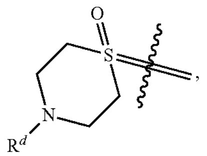

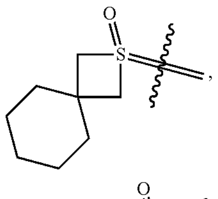

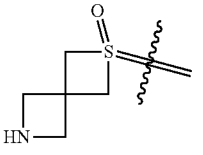

or

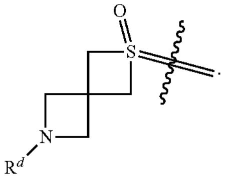

In some embodiments, $R^d$ is selected from the group consisting of halogen, hydroxy, amino, $C_{1-3}$ alkyl, $C_{1-3}$ alkoxy, $C_{1-3}$ alkyl-C(O)—, $C_{1-3}$ alkyl-$S(O)_2$—, $C_{3-6}$ cycloalkyl, 3-6 membered heterocycloalkyl (e.g., 3-, 4-, 5- or 6-membered), phenyl and 5-6 membered heteroaryl. In some embodiments, $R^d$ is selected from the group consisting of halogen, hydroxy, amino, $C_{1-3}$ alkyl and $C_{1-3}$ alkoxy. In some embodiments, $R^d$ is selected from the group consisting of $C_{1-3}$ alkyl and $C_{1-3}$ alkoxy.

In some embodiments, $R^d$ is selected from $C_{1-6}$ alkyl. In some embodiments, $R^d$ is selected from $C_{1-3}$ alkyl. In some embodiments, $R^d$ is selected from the group consisting of methyl, ethyl, n-propyl and isopropyl. In some embodiments, $R^d$ is selected from methyl.

In some embodiments, $R^1$ and $R^2$ are each independently selected from the group consisting of methyl, ethyl, tert-butyl, cyclopropyl, cyclopentyl, cyclohexyl, phenyl and

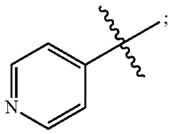 [SMILES: *c1ccncc1];

or $R^1$ and $R^2$, together with the sulfur atom to which they are attached, form

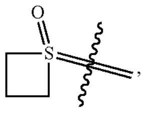, 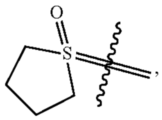, 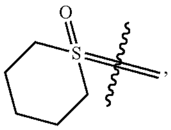,

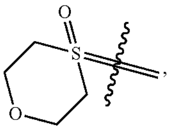, 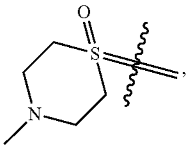,

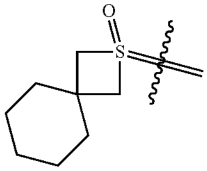 or 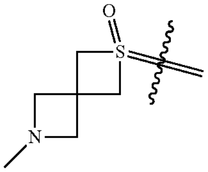.

In some embodiments, $R^1$ and $R^2$ are each independently selected from the group consisting of methyl, ethyl, cyclopropyl, phenyl and

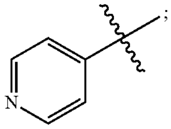 [SMILES: *c1ccncc1];

or $R^1$ and $R^2$, together with the sulfur atom to which they are attached, form

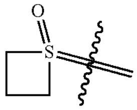, 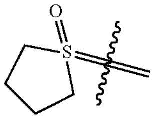, 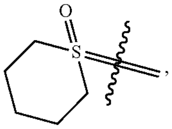,

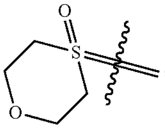, 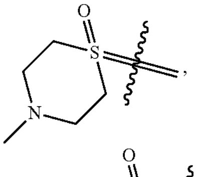,

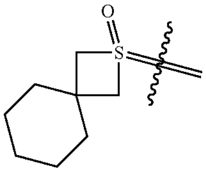 or 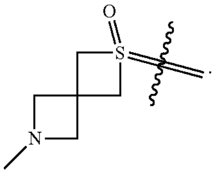.

In some embodiments, the structural unit

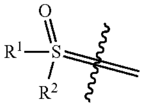

is selected from the group consisting of

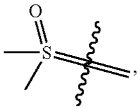, 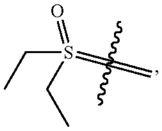, 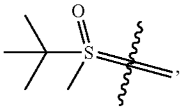,

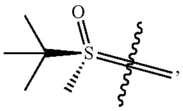, 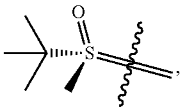, 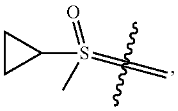,

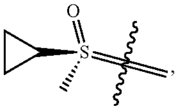, 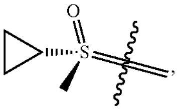, 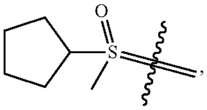,

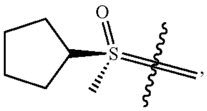, 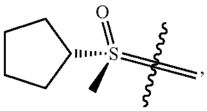,

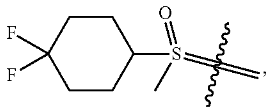, 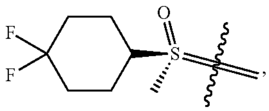,

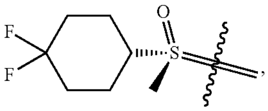, 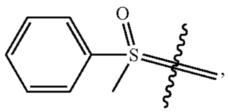,

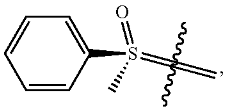, 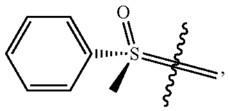,

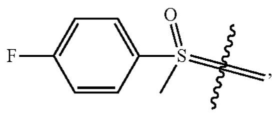, 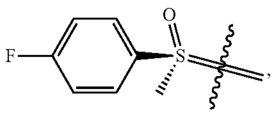,

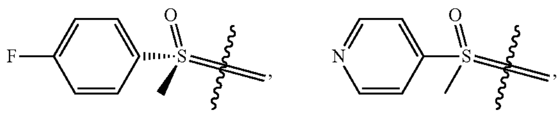,

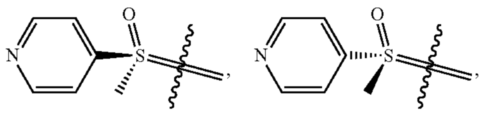,

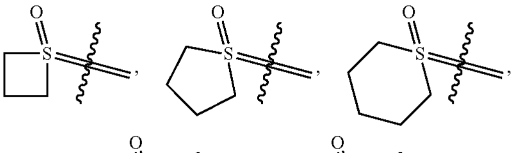,

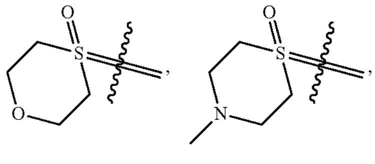,

-continued

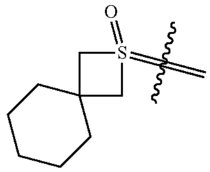 and 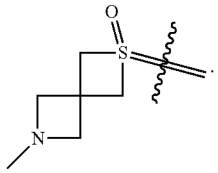.

In some embodiments, the structural unit

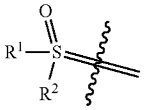

is selected from the group consisting of

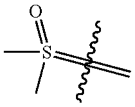, 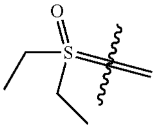, 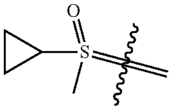,

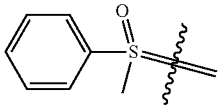, 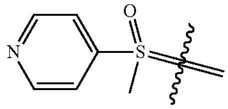,

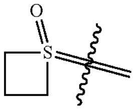, 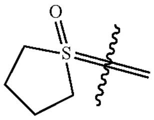, 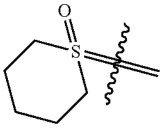,

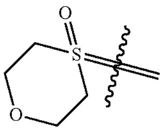, 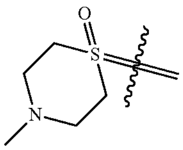,

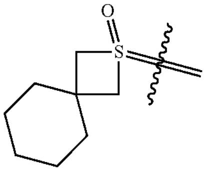 and 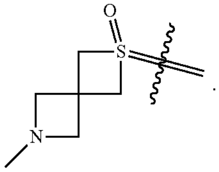.

In some embodiments, $R^3$ is selected from 5-6 membered heteroaryl optionally substituted with one or more $R^e$.

In some embodiments, $R^3$ is selected from 5-membered heteroaryl optionally substituted with one or more $R^e$.

In some embodiments, $R^3$ is selected from 5-membered N-containing heteroaryl optionally substituted with one or more $R^e$.

In some embodiments, $R^3$ is selected from pyrazolyl optionally substituted with one or more $R^e$.

In some embodiments, $R^3$ is selected from pyrazolyl optionally substituted with one $R^e$.

In some embodiments, $R^3$ is selected from the group consisting of

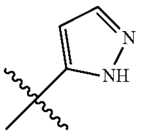 and 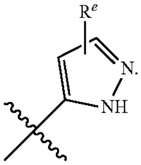

In some embodiments, $R^3$ is selected from the group consisting of

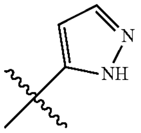 and 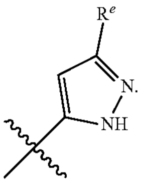

In some embodiments, $R^e$ is selected from the group consisting of hydroxy, amino, halogen, $C_{1-3}$ alkyl, $C_{1-3}$ haloalkyl, $C_{3-6}$ cycloalkyl and 3-6 membered heterocycloalkyl.

In some embodiments, $R^e$ is selected from the group consisting of $C_{1-3}$ alkyl, $C_{1-3}$ haloalkyl and $C_{3-6}$ cycloalkyl.

In some embodiments, $R^e$ is selected from the group consisting of methyl, trifluoromethyl and cyclopropyl.

In some embodiments, $R^3$ is selected from the group consisting of

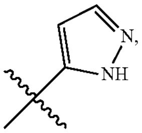 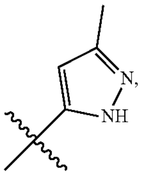 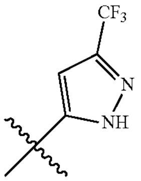 and 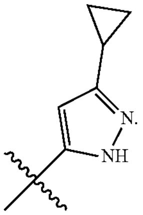

In some embodiments, $R^3$ is selected from

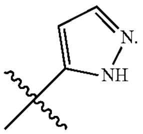 [SMILES: *c1ccn[nH]1]

In some embodiments, the compound of formula (I), the stereoisomer thereof or the pharmaceutically acceptable salt thereof of the present application is selected from a compound of formula (II), a stereoisomer thereof or a pharmaceutically acceptable salt thereof, (II)

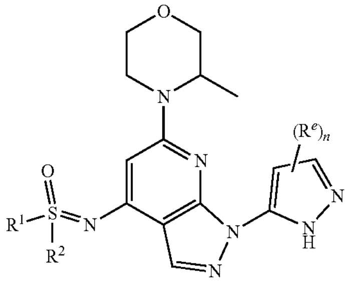

wherein $R^1$, $R^2$ and $R^e$ are as defined above;

n is selected from the group consisting of 0, 1 and 2. In some embodiments, n is selected from the group consisting of 0 and 1.

In some embodiments, the structural unit

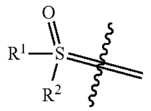

is as defined above.

In some embodiments, the compound of formula (I), the stereoisomer thereof or the pharmaceutically acceptable salt thereof of the present application is selected from a compound of formula (III), a stereoisomer thereof or a pharmaceutically acceptable salt thereof, (III)

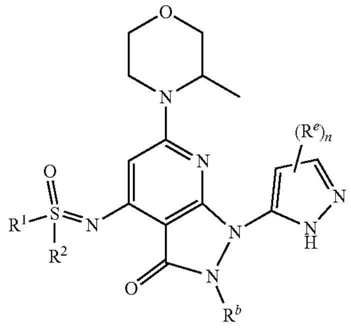

wherein $R^1$, $R^2$, $R^b$ and $R^e$ are as defined above;

n is selected from the group consisting of 0, 1 and 2. In some embodiments, n is selected from the group consisting of 0 and 1.

In some embodiments, the structural unit

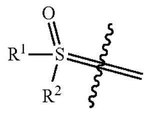

is as defined above.

In some embodiments, the compound of formula (I), the stereoisomer thereof or the pharmaceutically acceptable salt thereof of the present application is selected from the group consisting of a compound of formula (I-a), a compound of formula (I-b), a compound of formula (II-a), a compound of formula (II-b), a compound of formula (III-a), a compound of formula (III-b), a stereoisomer thereof and a pharmaceutically acceptable salt thereof, (I-a)

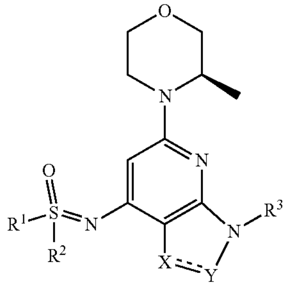

(I-b)

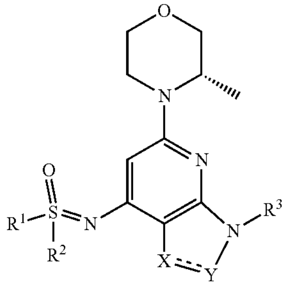

(II-a)

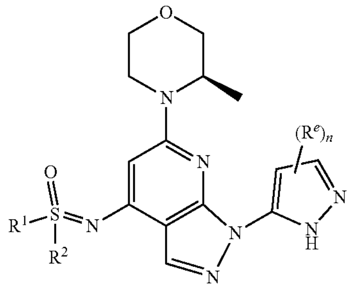

(II-b)

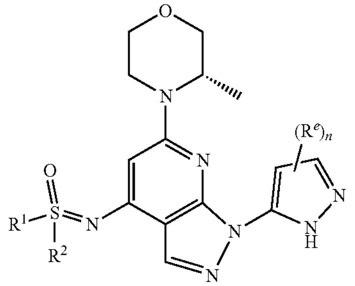

(III-a)

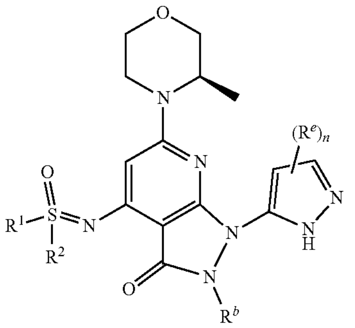

-continued (III-b)

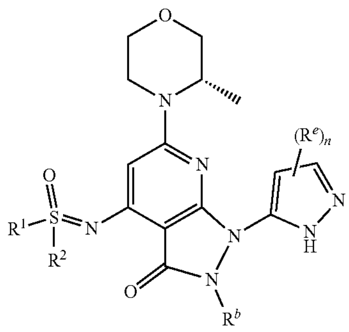

wherein X, Y, $R^1$, $R^2$, $R^3$, $R^b$ and $R^e$ are as defined above;

n is selected from the group consisting of 0, 1 and 2. In some embodiments, n is selected from the group consisting of 0 and 1.

In some embodiments, the structural unit

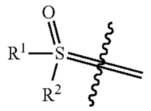

is as defined above.

In some embodiments, the heteroatoms in the heterocyclyl, heterocycloalkyl and heteroaryl are selected from the group consisting of N, O and S; further, the number of heteroatoms may be selected from the group consisting of 1, 2 and 3.

In some embodiments, the “one or more” is selected from the group consisting of one, two, three, four, five and six. In some embodiments, the “one or more” is selected from the group consisting of one, two and three. In some embodiments, the “one or more” is selected from the group consisting of one and two.

In some embodiments, the present application encompasses the variables defined above and embodiments thereof, as well as any combination thereof.

In some embodiments, the compound of formula (I) of the present application is selected from the group consisting of the following compounds, stereoisomers thereof and pharmaceutically acceptable salts thereof:

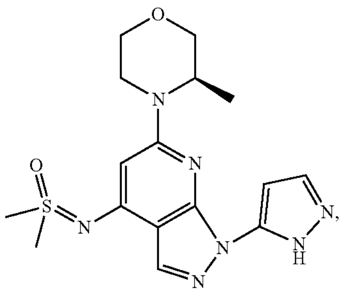

-continued

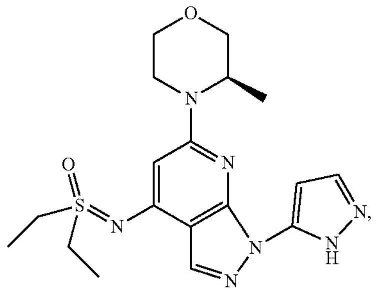

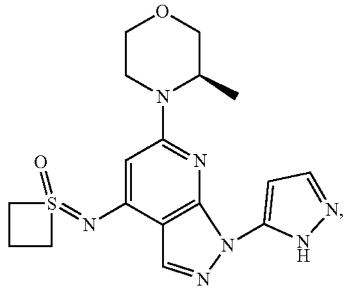

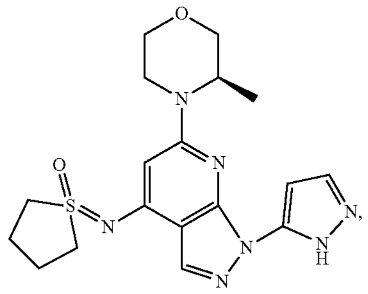

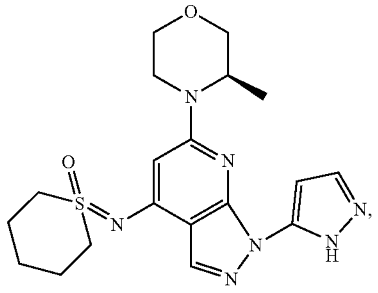

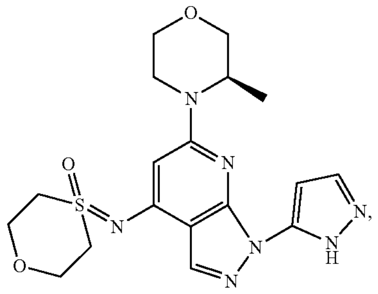

-continued
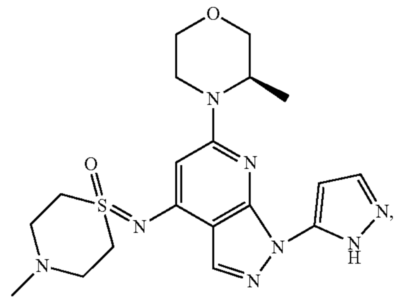
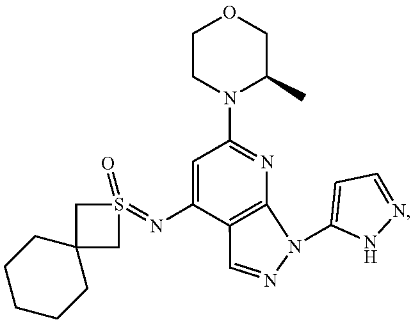
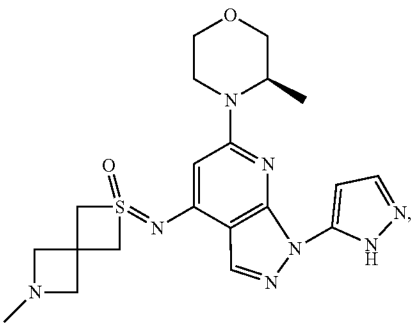
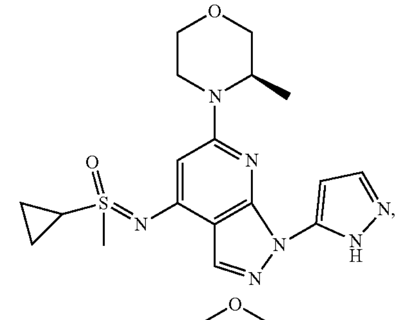
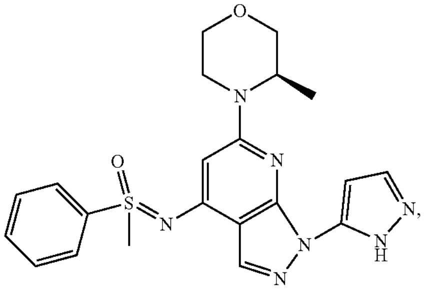
-continued
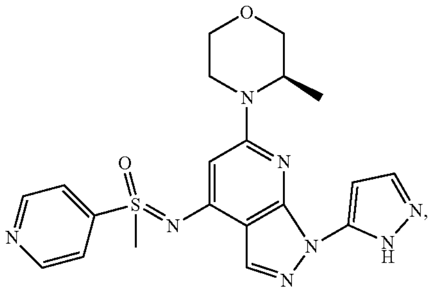
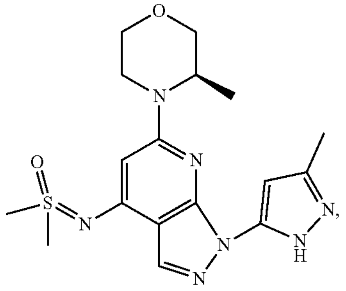
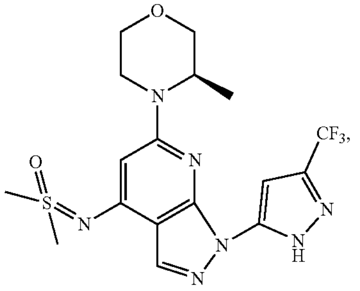
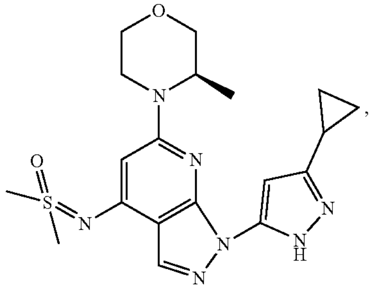
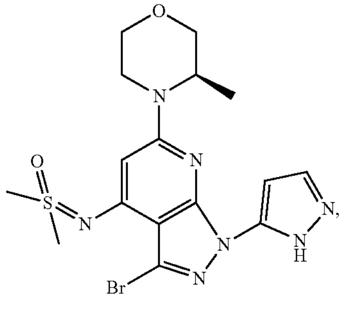

-continued
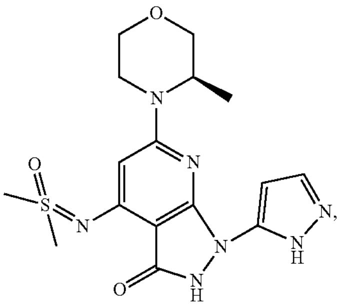
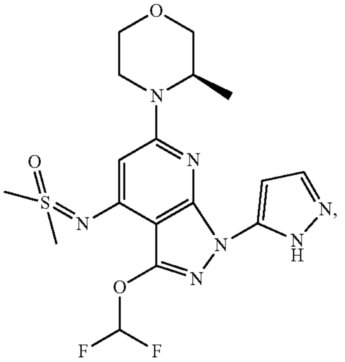
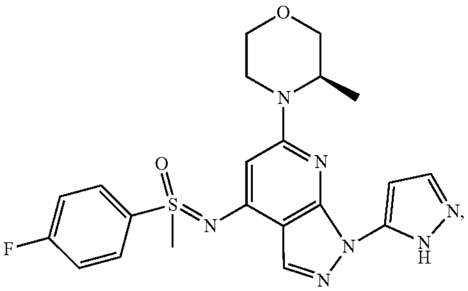
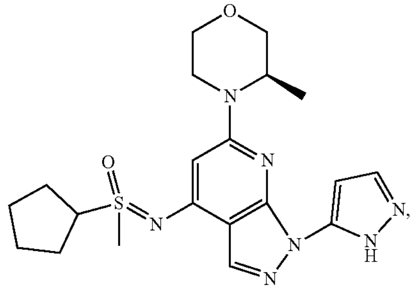
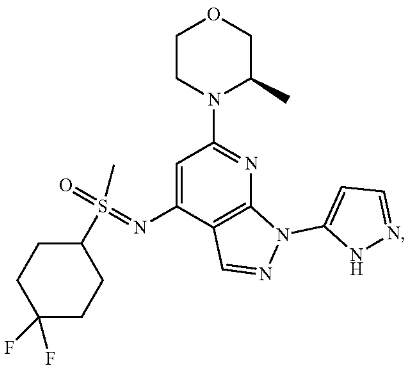
-continued
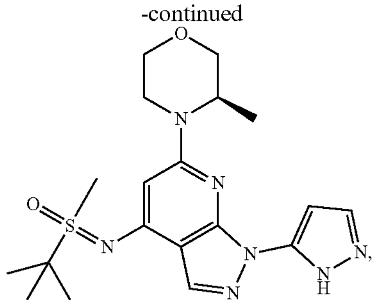
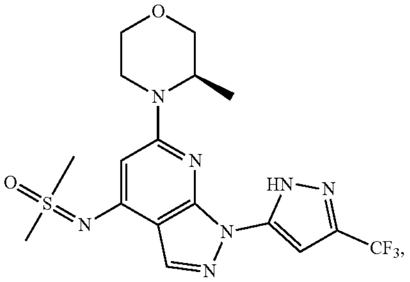
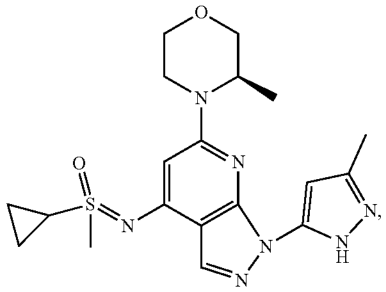
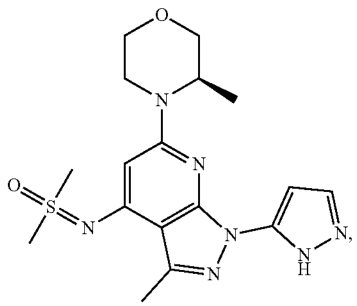
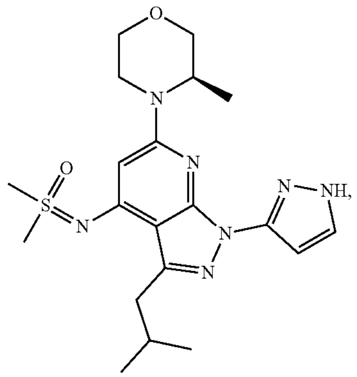

-continued
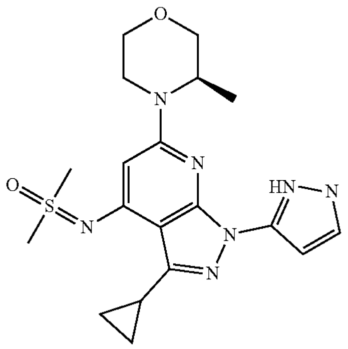
,
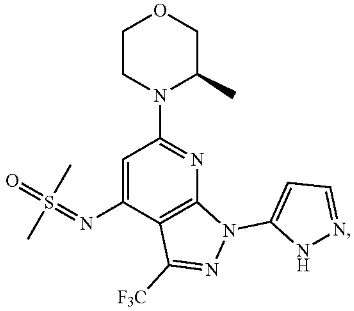
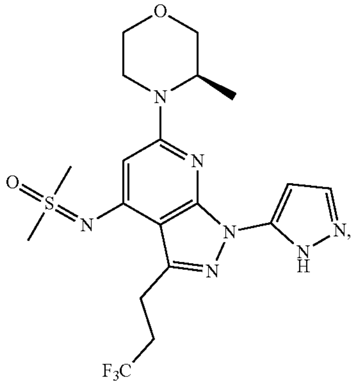
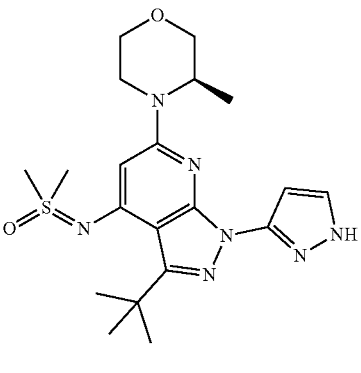
and
-continued
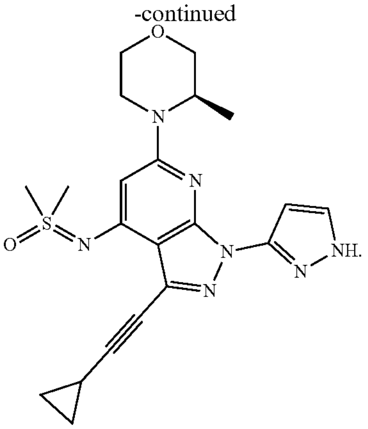
In some embodiments, the compound of formula (I) of the present application is selected from the group consisting of the following compounds, stereoisomers thereof and pharmaceutically acceptable salts thereof.
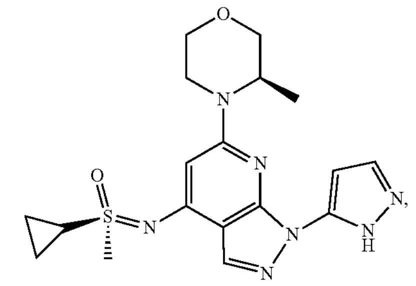
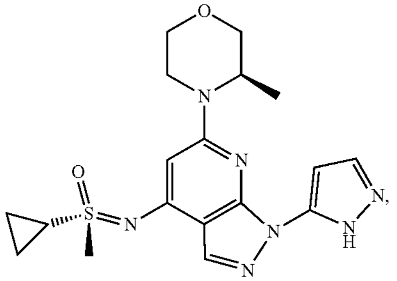
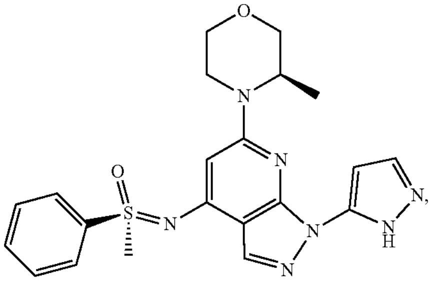
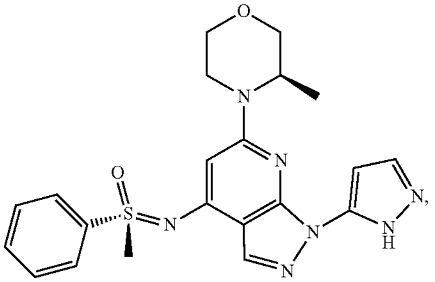

-continued
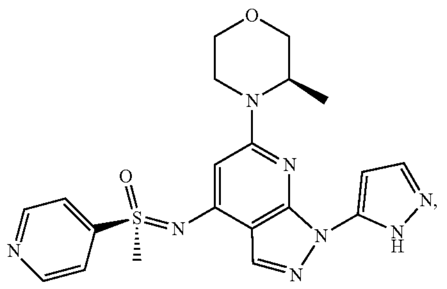
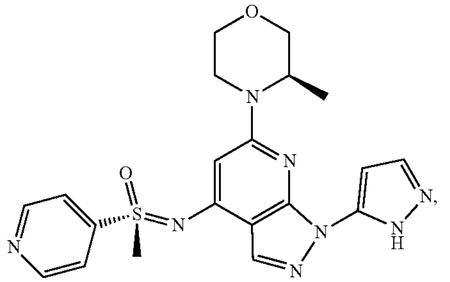
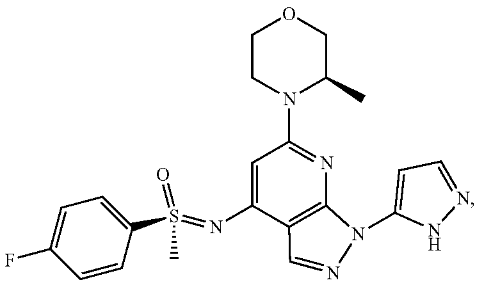
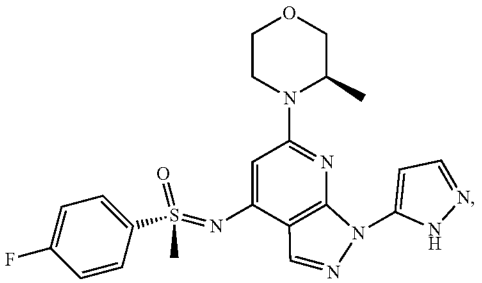
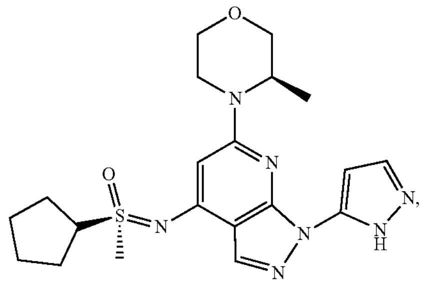
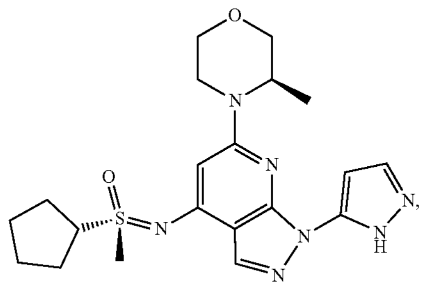
-continued
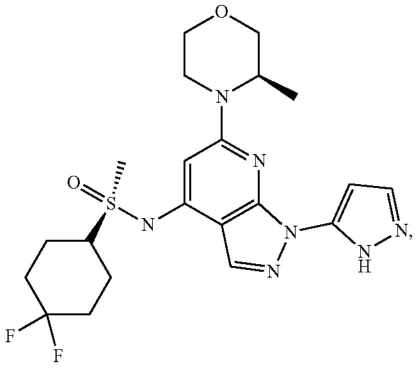
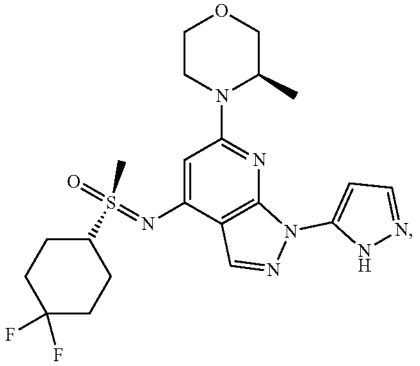
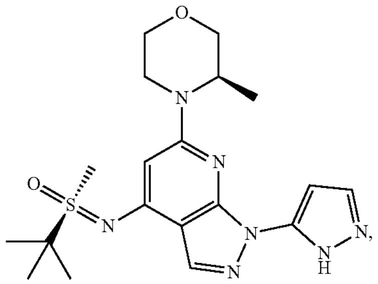
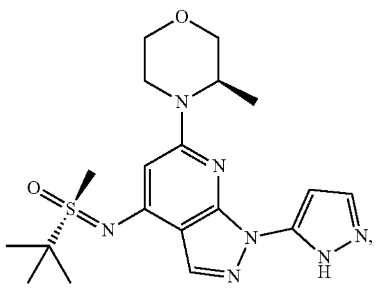
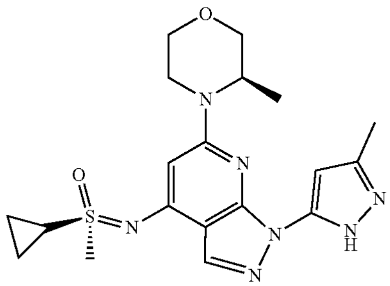
and -continued

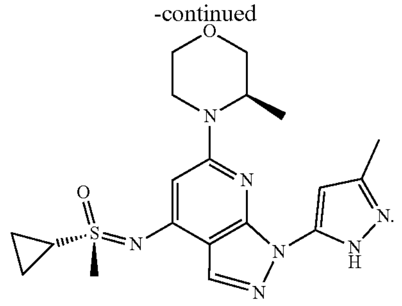

In another aspect, the present application provides a pharmaceutical composition comprising the compound, the stereoisomer thereof or the pharmaceutically acceptable salt thereof of the present application. In some embodiments, the pharmaceutical composition of the present application further comprises a pharmaceutically acceptable excipient.

In another aspect, the present application provides a method for inhibiting ATR kinase in a mammal, the method comprising administering to a mammal, preferably a human, in need of such treatment a therapeutically effective amount of the compound, the stereoisomer thereof or the pharmaceutically acceptable salt thereof, or the pharmaceutical composition thereof, described above.

In another aspect, the present application provides use of the compound, the stereoisomer thereof or the pharmaceutically acceptable salt thereof, or the pharmaceutical composition thereof, described above for preparing a medicament for inhibiting ATR kinase.

In another aspect, the present application provides use of the compound, the stereoisomer thereof or the pharmaceutically acceptable salt thereof, or the pharmaceutical composition thereof, described above in inhibiting ATR kinase.

In another aspect, the present application provides the compound, the stereoisomer thereof or the pharmaceutically acceptable salt thereof, or the pharmaceutical composition thereof, described above for inhibiting ATR kinase.

In another aspect, the present application provides a method for treating an ATR-related or ATR-mediated disease and/or disorder in a mammal, the method comprising administering to a mammal, preferably a human, in need of such treatment a therapeutically effective amount of the compound, the stereoisomer thereof or the pharmaceutically acceptable salt thereof, or the pharmaceutical composition thereof, described above.

In another aspect, the present application provides use of the compound, the stereoisomer thereof or the pharmaceutically acceptable salt thereof, or the pharmaceutical composition thereof, described above for preparing a medicament for treating an ATR-related or ATR-mediated disease and/or disorder.

In another aspect, the present application provides use of the compound, the stereoisomer thereof or the pharmaceutically acceptable salt thereof, or the pharmaceutical composition thereof, described above in treating an ATR-related or ATR-mediated disease and/or disorder.

In another aspect, the present application provides the compound, the stereoisomer thereof or the pharmaceutically acceptable salt thereof, or the pharmaceutical composition thereof, described above for use in treating an ATR-related or ATR-mediated disease and/or disorder.

In some embodiments, the ATR-related or ATR-mediated disease and/or disorder is selected from a hyperproliferative disease, such as cancer. In some embodiments, the cancer is selected from the group consisting of liver cancer, ovarian cancer, breast cancer, skin cancer, colorectal cancer, lung cancer, lymphoma, and the like.

The compound of the present application has good in vitro inhibitory activity against kinases and cell proliferation, shows stable in vivo and in vitro metabolism, and has relatively good in vivo exposure, half-life and bioavailability.

Definitions

Unless otherwise stated, the following terms used in the present application shall have the following meanings. A certain term, unless otherwise specifically defined, should not be considered uncertain or unclear, but construed according to its common meaning in the field. When referring to a trade name, it is intended to refer to its corresponding commercial product or its active ingredient. Chemical bond "------" represents a single bond or a double bond depending on the groups connected to the two ends of the chemical bond. For example, chemical bond "------" is a double bond when X and Y connected to the two ends of the chemical bond are $CR^a$ or N, respectively; chemical bond "------" is a single bond when one of X and Y connected to the two ends of the chemical bond is CO or $NR^a$. Those skilled in the art will appreciate that the selection of X and Y does not break the valence-bond rules.

The term "substituted" means that any one or more hydrogen atoms on a specific atom are substituted by substituents, as long as the valence of the specific atom is normal and the resulting compound is stable. When the substituent is oxo (namely =O), it means that two hydrogen atoms are substituted and oxo is not available on an aromatic group.

The terms "optional" or "optionally" means that the subsequently described event or circumstance may, but does not necessarily, occur. The description includes instances where the event or circumstance occurs and instances where it does not. For example, being optionally substituted with a group means being unsubstituted, or substituted with one or more such groups. Specifically, for example, an ethyl group being "optionally" substituted with a halogen means that the ethyl group may be unsubstituted ($CH_2CH_3$), monosubstituted (for example, $CH_2CH_2F$), polysubstituted (for example, $CHFCH_2F$, $CH_2CHF_2$, etc.) or fully substituted ($CF_2CF_3$). It will be appreciated by those skilled in the art that for any groups comprising one or more substituents, any substitutions or substituting patterns which may not exist or can not be synthesized spatially are not introduced. $C_{m-n}$ as used herein means that the portion has an integer number of carbon atoms in the given range. For example, "$C_{1-6}$" means that the group may have 1 carbon atom, 2 carbon atoms, 3 carbon atoms, 4 carbon atoms, 5 carbon atoms or 6 carbon atoms; "$C_{1-3}$" means that the group may have 1 carbon atom, 2 carbon atoms or 3 carbon atoms.

When any variable (e.g., R) occurs once or more in the constitution or structure of a compound, the definition of the variable in each case is independent. Therefore, for example, if a group is substituted with 2 R, the definition of each R is independent.

When a variable is selected from a covalent bond, it means that the two groups are directly connected. For example, in A-L-Z, when L represents a covalent bond, it means that the structure is actually A-Z.

When a bond of a substituent is crosslinked to two atoms on a ring, the substituent can be bonded to any atoms on the ring. For example, structural unit

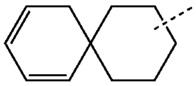 or 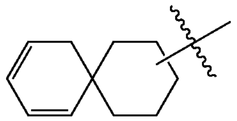

represents that substitution may occur in any one position of cyclohexyl or cyclohexadienyl.

The term "halo-" or "halogen" refers to fluorine, chlorine, bromine, and iodine.

The term "hydroxy" refers to the —OH group.

The term "amino" refers to the —$NH_2$ group.

The term "alkyl" refers to hydrocarbyl with a general formula of $C_nH_{2n+1}$. The alkyl can be linear or branched. For example, the term "$C_{1-6}$ alkyl" refers to alkyl containing 1 to 6 carbon atoms (for example, methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl, and the like). Likewise, the alkyl moieties (namely alkyl) of alkoxy, alkylamino, dialkylamino, alkylsulfonyl and alkylthio have the same definition as those described above.

The term "alkoxy" refers to —O-alkyl.

The term "alkylamino" refers to —NH-alkyl.

The term "alkynyl" refers to a linear or branched hydrocarbon chain containing 2 to 12 carbon atoms and having one or more triple bonds. Examples of alkynyl include, but are not limited to, ethynyl, propynyl, propargyl and 3-hexynyl.

The term "haloalkyl" refers to an alkyl group on which the hydrogen atoms are substituted with one or more halogen atoms. Non-limiting examples of haloalkyl include —$CH_2F$, —$CHF_2$, —$CF_3$, —$CCl_3$, —$CH_2CH_2F$, —$CH_2CHF_2$, —$CH_2CF_3$, —$CF_2CF_3$, and the like.

The term "cycloalkyl" refers to a fully saturated carbocycle which may exist in the form of a monocyclic, bridged cyclic or spiro cyclic structure. Unless otherwise specified, the carbocycle is generally a 3- to 10-membered ring. Non-limiting examples of cycloalkyl include cyclopropyl, cyclobutyl, cyclopentyl, cyclohexyl, norbornyl (bicyclo [2.2.1]heptyl), bicyclo[2.2.2]octyl, adamantyl, and the like.

The term "heterocyclyl" refers to a fully saturated or partially unsaturated (but not fully unsaturated heteroaromatic group) nonaromatic ring which may exist in the form of a monocyclic, bridged cyclic or spiro cyclic structure. Unless otherwise specified, the heterocycle is usually a 3- to 7-membered ring containing 1 to 3 heteroatoms (preferably 1 or 2 heteroatoms) independently selected from the group consisting of sulfur, oxygen, phosphorus and/or nitrogen. Non-limiting examples of heterocyclyl include oxiranyl, tetrahydrofuranyl, dihydrofuranyl, pyrrolidinyl, N-methylpyrrolidinyl, dihydropyrrolyl, piperidinyl, piperazinyl, pyrazolidinyl, 4H-pyranyl, morpholinyl, sulfomorpholinyl, tetrahydrothienyl,

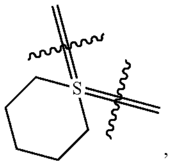 [SMILES: *=S1(=*)CCCCC1], or the like.

The term "heterocycloalkyl" refers to a fully saturated cyclic group which may exist in the form of a monocyclic, bridged cyclic or spiro cyclic structure. Unless otherwise specified, the heterocycle is usually a 3- to 7-membered ring containing 1 to 3 heteroatoms (preferably 1 or 2 heteroatoms) independently selected from the group consisting of sulfur, oxygen, phosphorus and/or nitrogen. Examples of 3-membered heterocycloalkyl include, but are not limited to, oxiranyl, thiiranyl, and aziranyl. Non-limiting examples of 4-membered heterocycloalkyl include, but are not limited to, azetidinyl, oxetanyl, and thietanyl. Examples of 5-membered heterocycloalkyl include, but are not limited to, tetrahydrofuranyl, tetrahydrothienyl, pyrrolidinyl, isoxazolidinyl, oxazolidinyl, isothiazolidinyl, thiazolidinyl, imidazolidinyl, tetrahydropyrazolyl, and

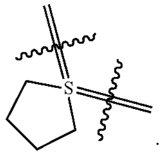 [SMILES: *=S1(=*)CCCC1].

Examples of 6-membered heterocycloalkyl include, but are not limited to, piperidinyl, tetrahydropyranyl, tetrahydrothiapyranyl, morpholinyl, piperazinyl, 1,4-oxathianyl, 1,4-dioxanyl, sulfomorpholinyl, 1,3-dithianyl, and 1,4-dithianyl. Examples of 7-membered heterocycloalkyl include, but are not limited to, azacycloheptanyl, oxacycloheptanyl, and thiocycloheptanyl. Monocyclic heterocycloalkyl having 5 or 6 ring atoms is preferred.

The term "mono heterocycloalkyl" refers to a heterocycloalkyl group that exists as a single ring.

The term "spiro heterocycloalkyl" refers to a fully saturated 5- to 20-membered polycyclic ring in which monocyclic rings share one carbon atom (referred to as the spiro atom), wherein one or more ring atoms in the polycyclic ring are selected from the group consisting of heteroatoms (preferably 1 or 2 heteroatoms) of sulfur, silicon, phosphorus, oxygen and/or nitrogen, and the remaining ring atoms are carbon atoms. It is preferably 6- to 14-membered, and is more preferably 6- to 10-membered. According to the number of spiro atoms shared among the rings, a spiro heterocyclic ring may be a monospiro heterocyclic ring, a bispiro heterocyclic ring or a polyspiro heterocyclic ring, preferably a monospiro heterocyclic ring or a bispiro heterocyclic ring, and more preferably a 4-membered/4-membered, 4-membered/5-membered, 4-membered/6-membered, 5-membered/5-membered or 5-membered/6-membered monospiro heterocyclic ring. Non-limiting examples of spiro heterocyclic rings include

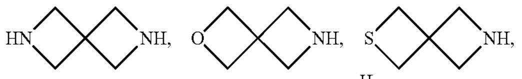

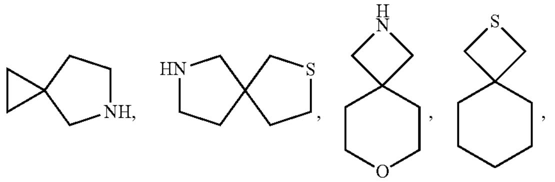

-continued

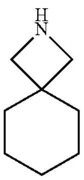,
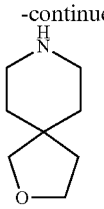
and
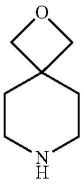.

The term "aryl" refers to an all-carbon aromatic monocyclic or fused polycyclic group having a conjugated π-electron system. For example, aryl may have 6-20 carbon atoms, 6-14 carbon atoms, or 6-12 carbon atoms. Non-limiting examples of aryl include phenyl, naphthyl, anthryl, 1,2,3,4-tetrahydronaphthalene, and the like.

The term "heteroaryl" refers to a monocyclic or fused polycyclic system which comprises at least one ring atom selected from the group consisting of N, O and S, with the remaining ring atoms being C, and which has at least one aromatic ring. Preferably, heteroaryl has a single 5- to 8-membered ring, or a plurality of fused rings comprising 6 to 14 ring atoms, particularly 6 to 10 ring atoms. Non-limiting examples of heteroaryl include pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl, and the like.

The term "treat" or "treatment" means administering a compound or formulation of the present application to ameliorate or eliminate a disease or one or more symptoms associated with the disease, including:

(i) inhibiting a disease or disease state, i.e., arresting its development; and (ii) alleviating a disease or disease state, i.e., causing its regression.

The term "prevent" or "prevention" means administering a compound or formulation of the present application to prevent a disease or one or more symptoms associated with the disease, including: preventing the occurrence of the disease or disease state in a mammal, particularly when such a mammal is predisposed to the disease state but has not yet been diagnosed with it.

The term "therapeutically effective amount" refers to an amount of a compound of the present application for (i) treating or preventing a specific disease, condition, or disorder, or (ii) alleviating, ameliorating, or eliminating one or more symptoms of a specific disease, condition, or disorder. The amount of the compound of the present application composing the "therapeutically effective amount" varies depending on the compound, the disease state and its severity, the administration regimen, and the age of the mammal to be treated, but can be determined routinely by those skilled in the art in accordance with their knowledge and the present disclosure.

The term "pharmaceutically acceptable" is used herein for those compounds, materials, compositions, and/or dosage forms which are, within the scope of sound medical judgment, suitable for use in contact with the tissues of human beings and animals without excessive toxicity, irritation, allergic response, or other problems or complications, and commensurate with a reasonable benefit/risk ratio.

A pharmaceutically acceptable salt, for example, may be a metal salt, an ammonium salt, a salt formed with an organic base, a salt formed with an inorganic acid, a salt formed with an organic acid, a salt formed with a basic or acidic amino acid, and the like.

The term "pharmaceutical composition" refers to a mixture consisting of one or more of the compounds or the salts thereof of the present application and a pharmaceutically acceptable excipient. The pharmaceutical composition is intended to facilitate the administration of the compound of the application to an organism.

The term "pharmaceutically acceptable excipient" refers to those that do not have a significant irritating effect on an organism and do not impair the biological activity and properties of the active compound. Suitable excipients are well known to those skilled in the art, such as carbohydrate, wax, water-soluble and/or water-swellable polymers, hydrophilic or hydrophobic material, gelatin, oil, solvent, water and the like.

The word "comprise" and variations thereof such as "comprises" or "comprising" will be understood in an open, non-exclusive sense, i.e., "including but not limited to".

The compounds of the present invention may exist in the form of a specific geometric isomer or stereoisomer. All such compounds are contemplated herein, including cis and trans isomers, (−)- and (+)-enantiomers, (R)- and (S)-enantiomers, diastereoisomers, (D)-isomers, (L)-isomers, and racemic mixtures and other mixtures thereof, such as an enantiomer or diastereomer enriched mixture, all of which are encompassed within the scope of the present invention. The substituents such as alkyl may have an additional asymmetric carbon atom. All these isomers and mixtures thereof are encompassed within the scope of the present invention.

Unless otherwise stated, "(D)" or "(+)" stands for dextrorotation, "(L)" or "(−)" stands for levorotation, and "(DL)" or "(±)" stands for racemization.

Unless otherwise stated, the absolute configuration of a stereogenic center is represented by a wedged solid bond () and a wedged dashed bond (), and the relative configuration of a stereogenic center is represented by a straight solid bond () and a straight dashed bond (). Optically active (R)- and (S)-isomers and D and L isomers can be prepared by chiral synthesis or chiral reagents or other conventional techniques. If one enantiomer of a certain compound of the present invention is to be obtained, the desired pure enantiomer can be prepared by asymmetric synthesis or derivatization using a chiral additive, wherein the resulting diastereoisomeric mixture is separated and the auxiliary group is cleaved. Alternatively, when the molecule contains a basic functional group (such as amino) or an acidic functional group (such as carboxyl), the compound reacts with an appropriate optically active acid or base to form a salt of the diastereoisomer, which is then subjected to diastereoisomeric resolution through conventional methods well known in the art to give the pure enantiomer. Furthermore, the enantiomer and the diastereoisomer are generally isolated by chromatography using a chiral stationary phase, optionally in combination with chemical derivatization (e.g., carbamate generated from amines).

The present application also comprises isotopically labeled compounds which are identical to those recited herein but have one or more atoms replaced by an atom having an atomic mass or mass number different from the atomic mass or mass number usually found in nature. Examples of isotopes that can be incorporated into the compounds of the present application include isotopes of hydrogen, carbon, nitrogen, oxygen, phosphorus, sulfur, fluorine, iodine and chlorine, such as 2H, $^{3}H$, $^{11}C$, $^{13}C$, $^{14}C$, $^{13}N$ $^{15}N$, $^{15}O$, $^{17}O$, $^{18}O$, $^{31}P$, $^{32}P$, $^{35}S$, $^{18}F$, $^{123}I$, $^{125}I$ and $^{36}Cl$.

Certain isotopically labeled compounds of the present application (e.g., those labeled with $^{3}H$ and $^{14}C$) can be used to analyze compounds and/or substrate tissue distribution.

Tritiated (i.e., $^3H$) and carbon-14 (i.e., $^{14}C$) isotopes are particularly preferred for their ease of preparation and detectability. Positron emitting isotopes, such as $^{15}O$, $^{13}N$, $^{11}C$, and $^{18}F$ can be used in positron emission tomography (PET) studies to determine substrate occupancy. Isotopically labeled forms of the compounds of the present application can generally be prepared by following procedures analogous to those disclosed in the schemes and/or examples below while substituting a non-isotopically labeled reagent with an isotopically-labeled reagent.

Furthermore, substitution with heavier isotopes such as deuterium (i.e., $^2H$ and D) may provide certain therapeutic advantages (e.g., increased in vivo half-life or reduced dosage) resulting from greater metabolic stability and hence may be preferred in some circumstances in which deuterium substitution may be partial or complete, wherein partial deuterium substitution refers to substitution of at least one hydrogen with at least one deuterium.

The pharmaceutical composition of the present application can be prepared by combining the compound of the present application with a suitable pharmaceutically acceptable excipient, and can be formulated, for example, into a solid, semisolid, liquid, or gaseous formulation such as tablet, pill, capsule, powder, granule, ointment, emulsion, suspension, suppository, injection, inhalant, gel, microsphere, aerosol and the like.

Typical routes of administration of the compound or the pharmaceutically acceptable salt thereof or the pharmaceutical composition thereof of the present application include, but are not limited to, oral, rectal, local, inhalation, parenteral, sublingual, intravaginal, intranasal, intraocular, intraperitoneal, intramuscular, subcutaneous and intravenous administration.

The pharmaceutical composition of the present application can be manufactured using methods well known in the art, such as conventional mixing, dissolving, granulating, dragee-making, levigating, emulsifying, lyophilizing and the like.

In some embodiments, the pharmaceutical composition is in an oral form. For oral administration, the pharmaceutical composition can be formulated by mixing the active compounds with pharmaceutically acceptable excipients well known in the art. These excipients enable the compounds of the present application to be formulated into tablets, pills, pastilles, dragees, capsules, liquids, gels, slurries, suspensions, etc. for oral administration to a patient.

A solid oral composition can be prepared by conventional mixing, filling or tableting. For example, it can be obtained by the following method: mixing the active compounds with solid excipients, optionally grinding the resulting mixture, adding additional suitable excipients if desired, and processing the mixture into granules to get the core parts of tablets or dragees. Suitable excipients include, but are not limited to: binders, diluents, disintegrants, lubricants, glidants, sweeteners or flavoring agents and the like.

The pharmaceutical composition may also be suitable for parenteral administration, such as a sterile solution, a suspension, or a lyophilized product in a suitable unit dosage form.

In all of the administration methods of the compound of general formula (I) described herein, the daily dose administered is from 0.01 to 200 mg/kg body weight, given in individual or separated doses.

The compounds of the present application can be prepared using a variety of synthetic methods well known to those skilled in the art, including the specific embodiments listed below, embodiments formed by combinations thereof with other chemical synthetic methods, and equivalents thereof known to those skilled in the art. The preferred embodiments include, but are not limited to, the examples of the present application.

The chemical reactions of the specific embodiments of the present application are conducted in a proper solvent that must be suitable for the chemical changes in the present application and the reagents and materials required. In order to obtain the compounds of the present application, it is sometimes necessary for those skilled in the art to modify or select a synthesis procedure or a reaction process based on the existing embodiments.

An important consideration in synthetic route planning in the art is the selection of suitable protecting groups for reactive functional groups (e.g., amino in the present application). For example, reference may be made to *Greene's Protective Groups in Organic Synthesis* (4th Ed.) Hoboken, New Jersey: John Wiley & Sons, Inc. All references cited in the present application are incorporated herein by reference in their entirety.

In some embodiments, the compounds of the present application can be prepared by those skilled in the art of organic synthesis according to the following scheme:

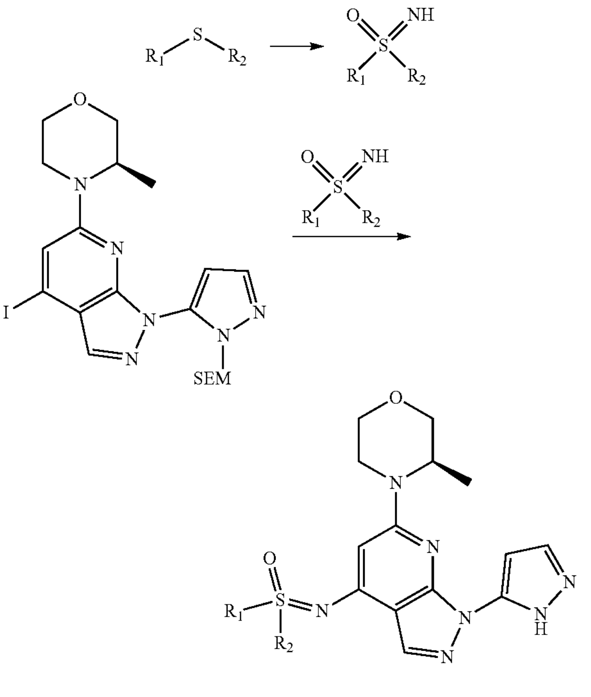

wherein $R^1$ and $R^2$ are as defined above.

The present application uses the following abbreviations: HEPES for 4-(2-hydroxyethyl)-1-piperazineethanesulfonic acid; $MgCl_2$ for magnesium chloride; DTT for dithiothreitol; EGTA for ethylene glycol bis(2-aminoethyl ether) tetraacetic acid; DMSO for dimethyl sulfoxide; EDTA for ethylenediaminetetraacetic acid; HU for hydroxyurea; and SEM for (trimethylsilyl)ethoxymethyl.

DETAILED DESCRIPTION

For clarity, the present application is further described with the following examples, which are, however, not intended to limit the scope of the present application. It will be apparent to those skilled in the art that various changes and modifications can be made to the specific examples of the present invention without departing from the spirit and scope of the present invention. All reagents used in the present application are commercially available and can be used without further purification.

Synthesis of Intermediates

Intermediate 1: Synthesis of Compound A1 and Compound A2

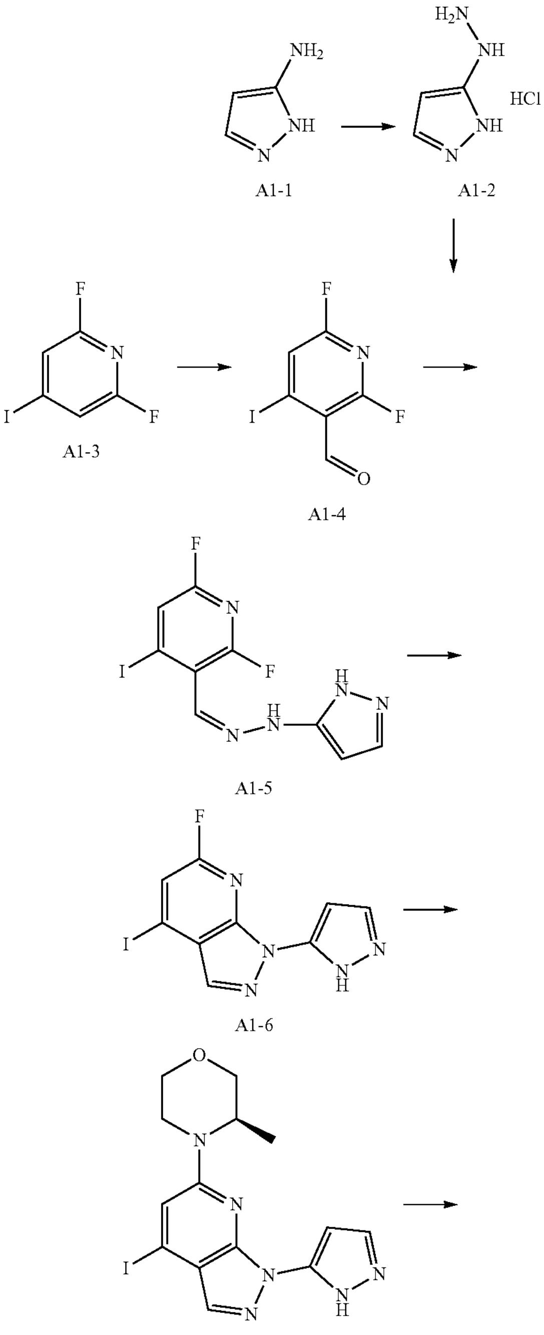

A1-1, A1-2, A1-3, A1-4, A1-5, A1-6, A1-7

-continued

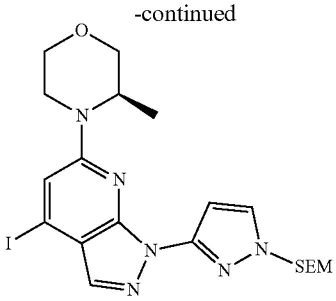

A1

+

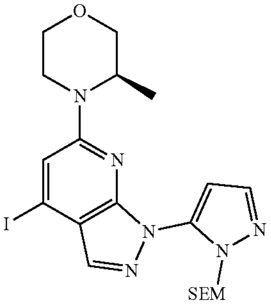

A2

Step 1: Synthesis of Compound A1-2

Compound A1-1 (20 g) was dissolved in 6 M diluted hydrochloric acid (140 mL). The mixture was cooled to 5° C., and a 1 M aqueous solution of sodium nitrite (241 mL) was added dropwise. After 1 h of reaction, a 1 M solution of stannous chloride in aqueous hydrochloric acid (480 mL) was added dropwise to the mixture. The mixture was left to react overnight at room temperature. The reaction solution was concentrated, and the resulting crude product was slurried with ethyl acetate (100 mL), then filtered, and the filter cake was dried to give compound A1-2 (62.9 g, crude). The product was directly used in the next step.

MS (ESI, $[M+H]^+$) m/z: 99.07.

$^1$H NMR (500 MHz, DMSO-$d_6$) δ 9.88 (s, 3H), 7.64 (d, J=2.4 Hz, 1H), 5.82 (d, J=2.4 Hz, 1H).

Step 2: Synthesis of Compound A1-4

Compound A1-3 (14 g), toluene (105 mL) and diethyl ether (105 mL) were mixed and cooled to −78° C., and a 2 M solution of lithium diisopropylamide in tetrahydrofuran/n-hexane (35 mL) was added dropwise. The mixture was left to react at −78° C. for 1 h. Ethyl formate (6.46 g) was added to the reaction solution, and the mixture was left to react at −78° C. for another 30 min. Formic acid (5.35 g) and ethyl acetate (100 mL) were then added, and the reaction solution was warmed to room temperature. The organic phase was washed with water and saturated brine successively and dried over anhydrous sodium sulfate. After filtration and concentration, the crude product was separated and purified by column chromatography (petroleum ether:ethyl acetate=5:1) to give compound A1-4 (11.2 g).

$^1$H NMR (500 MHz, $CDCl_3$) δ 10.11 (s, 1H), 7.54 (d, J=3.0 Hz, 1H).

Step 3: Synthesis of Compound A1-5

Compound A1-2 (15 g), compound A1-4 (6 g) and ethanol (100 mL) were mixed and left to react at room temperature for 30 min. The reaction solution was concentrated, and the residue was dissolved in ethyl acetate. The solution was washed with saturated sodium bicarbonate, water and saturated brine successively, dried over anhydrous sodium sulfate, filtered, and concentrated to give compound A1-5 (6.02 g).

MS (ESI, $[M+H]^+$) m/z: 349.87.

$^1H$ NMR (500 MHz, DMSO-$d_6$) δ 12.01 (s, 1H), 10.85 (s, 1H), 7.94 (s, 1H), 7.81 (d, J=2.7 Hz, 1H), 7.53 (d, J=1.3 Hz, 1H), 5.97 (s, 1H).

Step 4: Synthesis of Compound A1-6

Compound A1-5 (10 g) and N-methylpyrrolidone (140 mL) were mixed, microwaved to 200° C. and left to react for 20 min. Water was added to the reaction solution, and a solid precipitated. The solid was collected by filtration, washed and dried to give compound A1-6 (7.4 g).

MS (ESI, $[M+H]^+$) m/z: 329.83.

$^1H$ NMR (500 MHz, DMSO-$d_6$) δ 13.10 (s, 1H), 8.27 (s, 1H), 7.93 (d, J=2.2 Hz, 1H), 7.68 (s, 1H), 6.67 (d, J=2.3 Hz, 1H).

Step 5: Synthesis of Compound A1-7

Compound A1-6 (7 g), (R)-3-methylmorpholine (4.3 g) and dimethyl sulfoxide (30 mL) were mixed, heated to 120° C. and left to react for 4 h. Water was added to the reaction solution, and a solid precipitated. The solid was collected by filtration, washed and dried to give compound A1-7 (6.8 g).

MS (ESI, $[M+H]^+$) m/z: 411.00.

$^1H$ NMR (500 MHz, DMSO-$d_6$) δ 12.87 (s, 1H), 7.84 (d, J=11.2 Hz, 2H), 7.28 (s, 1H), 6.76 (d, J=1.8 Hz, 1H), 4.45 (d, J=4.9 Hz, 1H), 4.08-3.99 (m, 1H), 3.95 (dd, J=11.4, 3.4 Hz, 1H), 3.74 (d, J=11.4 Hz, 1H), 3.63 (dd, J=11.4, 2.9 Hz, 1H), 3.48 (td, J=11.9, 2.9 Hz, 1H), 3.17 (td, J=12.8, 3.6 Hz, 1H), 1.19 (d, J=6.7 Hz, 3H).

Step 6: Synthesis of Compound A1 and Compound A2

Compound A1-7 (4 g), diisopropylethylamine (3.78 g) and dichloromethane (60 mL) were mixed, and 2-(trimethylsilyl)ethoxymethyl chloride (3.25 g) was added dropwise. The mixture was left to react at room temperature for 30 min. Dichloromethane (20 mL) and saturated sodium bicarbonate (20 mL) were added to the reaction solution. The organic phase was separated and concentrated, and the resulting crude product was separated and purified by column chromatography (petroleum ether:ethyl acetate=1:1) to give compound A1 (2.02 g) and compound A2 (1.13 g).

Compound A1

MS (ESI, $[M+H]^+$) m/z: 541.02.

$^1H$ NMR (500 MHz, $CDCl_3$) δ 7.83 (s, 1H), 7.64 (d, J=1.8 Hz, 1H), 7.00 (s, 1H), 6.59 (d, J=1.8 Hz, 1H), 5.72-5.65 (m, 2H), 4.34-4.27 (m, 1H), 4.01 (dd, J=11.5, 3.7 Hz, 1H), 3.95 (dd, J=13.3, 2.5 Hz, 1H), 3.79 (d, J=11.4 Hz, 1H), 3.71 (dd, J=11.5, 3.1 Hz, 1H), 3.56 (td, J=12.0, 3.1 Hz, 1H), 3.47-3.38 (m, 2H), 3.25 (td, J=12.8, 3.9 Hz, 1H), 1.29 (d, J=6.8 Hz, 3H), 0.78-0.72 (m, 2H), −0.15 (s, 9H).

Compound A2

MS (ESI, $[M+H]^+$) m/z: 541.02.

$^1H$ NMR (500 MHz, DMSO-$d_6$) δ8.02 (d, J=2.4 Hz, 1H), 7.84 (s, 1H), 7.28 (s, 1H), 6.86 (d, J=2.4 Hz, 1H), 5.43 (s, 2H), 4.51-4.41 (m, 1H), 4.05-4.01 (m, 1H), 3.94 (dd, J=11.4, 3.5 Hz, 1H), 3.73 (d, J=11.4 Hz, 1H), 3.66-3.57 (m, 3H), 3.48 (td, J=11.9, 3.0 Hz, 1H), 3.17 (td, J=12.8, 3.7 Hz, 1H), 1.19 (d, J=6.7 Hz, 3H), 0.88-0.82 (m, 2H), −0.05 (s, 9H).

Intermediate 2: Synthesis of Compound B1

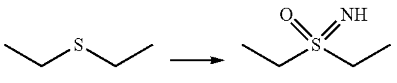

B1-1 B1

Compound B1-1 (1 g), iodobenzene diacetate (10.71 g), ammonium carbamate (3.46 g) and methanol (10 mL) were mixed and left to react at room temperature for 1 h. The reaction solution was filtered and concentrated, and the crude product was separated and purified by column chromatography (dichloromethane:methanol=50:1) to give compound B1 (750 mg).

$^1H$ NMR (500 MHz, DMSO-$d_6$): δ 3.01-2.88 (m, 4H), 1.20 (t, J=7.4 Hz, 6H).

Intermediate 3: Synthesis of Compound C1

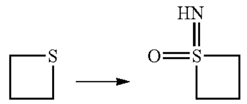

C1-1 C1

Compound C1-1 (0.8 g), iodobenzene diacetate (10.43 g), ammonium carbamate (3.37 g) and methanol (10 mL) were mixed and left to react at room temperature for 1 h. The reaction solution was filtered and concentrated, and the crude product was separated and purified by column chromatography (dichloromethane:methanol=50:1) to give compound C1 (450 mg).

$^1H$ NMR (500 MHz, DMSO-$d_6$): δ 4.01-3.80 (m, 4H), 2.13-1.96 (m, 2H).

Intermediate 4: Synthesis of Compound

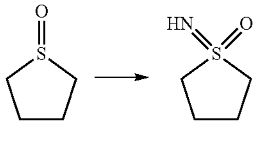

D1-1 D1

Compound D1-1 (1 g), iodobenzene diacetate (3 g), ammonium carbamate (9.28 g) and methanol (20 mL) were mixed and left to react at room temperature for 1 h. The reaction solution was filtered and concentrated, and the crude product was separated and purified by column chromatography (dichloromethane:methanol=20:1) to give compound D1 (1.12 g).

$^1H$ NMR (500 MHz, $CDCl_3$) δ 3.15-3.12 (m, 4H), 2.28-2.24 (m, 4H).

Intermediate 5: Synthesis of Compound E1

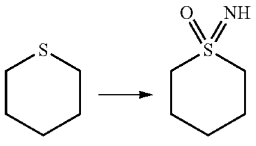

E1-1 E1

Compound E1-1 (thiocyclopentane) (0.5 g), methanol (10 mL), ammonium carbamate (0.57 g) and iodobenzene diacetate (3.31 g) were mixed and left to react at room temperature for 0.5 h. The reaction solution was filtered and concentrated, and the resulting crude product was separated and purified by column chromatography (dichloromethane:methanol=20:1) to give compound E1 (0.48 g).

$^1$H NMR (500 MHz, $CDCl_3$) δ 3.32 (s, 1H), 3.10-3.02 (m, 4H), 2.09-2.06 (m, 4H), 1.64 (qd, J=5.8, 4.9, 3.2 Hz, 2H).

Intermediate 6: Synthesis of Compound F1

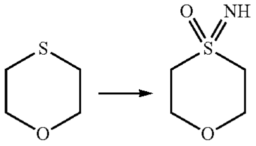

F1-1 F1

Compound F1-1 (0.5 g), methanol (10 mL), ammonium carbamate (0.56 g) and iodobenzene diacetate (3.09 g) were mixed and left to react at room temperature for 1 h. The reaction solution was filtered and concentrated, and the resulting crude product was separated and purified by column chromatography (dichloromethane:methanol=20:1) to give compound F1 (0.605 g).

$^1$H NMR (500 MHz, $CDCl_3$) δ 4.17-4.08 (m, 4H), 3.21-3.12 (m, 4H).

Intermediate 7: Synthesis of Compound G1

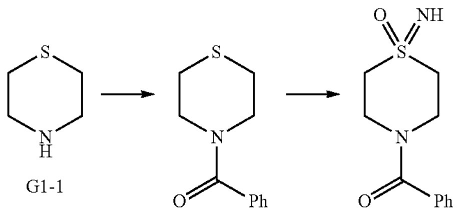

G1-1 G1-2 G1

Step 1: Synthesis of Compound G1-2

Compound G1-1 (2.064 g) was dissolved in dichloromethane (20 mL), triethylamine (3.04 g) was added, and benzoyl chloride (2.81 g) was added dropwise under ice-bath conditions. After the addition, the mixture was left to react overnight at room temperature. The reaction solution was diluted with dichloromethane, washed with a saturated solution of sodium bicarbonate, water and saturated brine successively, and dried over anhydrous sodium sulfate. After filtration and concentration, compound G1-2 (4.1 g) was obtained.

$^1$H NMR (500 MHz, DMSO-$d_6$) δ 7.45-7.43 (m, 3H), 7.38 (dd, J=6.7, 3.1 Hz, 2H), 3.86-3.54 (m, 4H), 2.72-2.54 (m, 4H).

Step 2: Synthesis of Compound G1

Compound G1-2 (1 g) was dissolved in methanol (15 mL), and ammonium carbamate (0.565 g) and iodobenzene diacetate (3.26 g) were added. The mixture was left to react at room temperature for 0.5 h. The reaction solution was filtered and concentrated, and the resulting crude product was separated and purified by column chromatography (dichloromethane:methanol=19:1) to give compound G1 (0.82 g).

$^1$H NMR (500 MHz, DMSO-$d_6$) δ 7.56-7.37 (m, 5H), 4.29-4.07 (brs, 1H), 3.86-3.54 (m, 4H), 3.22-2.90 (m, 4H).

Intermediate 8: Synthesis of Compound H1

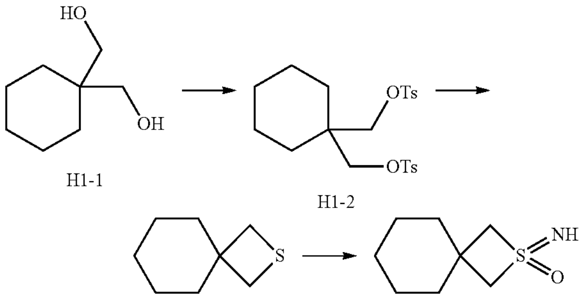

H1-1 H1-2 H1-3 H1

Step 1: Synthesis of Compound H1-2

Compound H1-1 (2 g) was dissolved in pyridine (5 mL), and a solution of p-toluenesulfonyl chloride (5.82 g) in pyridine (56 mL) was added dropwise under ice-bath conditions. The mixture was left to react overnight at room temperature. Dichloromethane was added to the reaction solution. The mixture was washed with 1 M diluted hydrochloric acid, water and saturated brine successively and dried over anhydrous sodium sulfate. After filtration and concentration, the resulting crude product was purified by silica gel column chromatography (petroleum ether:ethyl acetate=1:1) to give compound H1-2 (3.1 g).

$^1$H NMR (500 MHz, $CDCl_3$) δ 7.73 (d, J=8.3 Hz, 4H), 7.35 (d, J=8.0 Hz, 4H), 3.83 (s, 4H), 2.46 (s, 6H), 1.32 (s, 10H).

Step 2: Synthesis of Compound H1-3

Compound H1-2 (3 g) was dissolved in N,N-dimethylformamide (50 mL), and sodium sulfide nonahydrate (3.18 g) was added. The mixture was heated to 100° C. and left to react for 7 h. Water was added to the reaction solution, and the mixture was extracted with ethyl acetate. The organic phase was washed with water and saturated brine successively and dried over anhydrous sodium sulfate. After filtration and concentration, the resulting crude product was purified by silica gel column chromatography (petroleum ether:ethyl acetate=19:1) to give compound H1-3 (0.22 g).

$^1H$ NMR (500 MHz, $CDCl_3$) δ 2.90 (s, 4H), 1.68 (s, 4H), 1.40 (q, J=5.7 Hz, 4H), 1.35-1.29 (m, 2H).

Step 3: Synthesis of Compound

Compound H1-3 (200 mg) was dissolved in methanol (10 mL), and ammonium carbamate (165 mg) and iodobenzene diacetate (951 mg) were added. The mixture was left to react at room temperature for 0.5 h. The reaction solution was filtered and concentrated, and the resulting crude product was separated and purified by column chromatography (dichloromethane:methanol=19:1) to give compound H1 (0.27 g).

$^1H$ NMR (500 MHz, $CDCl_3$) δ 3.84-3.74 (m, 4H), 1.79 (dt, J=19.5, 5.5 Hz, 4H), 1.48-1.42 (m 6H).

Intermediate 9: Synthesis of Compound I1

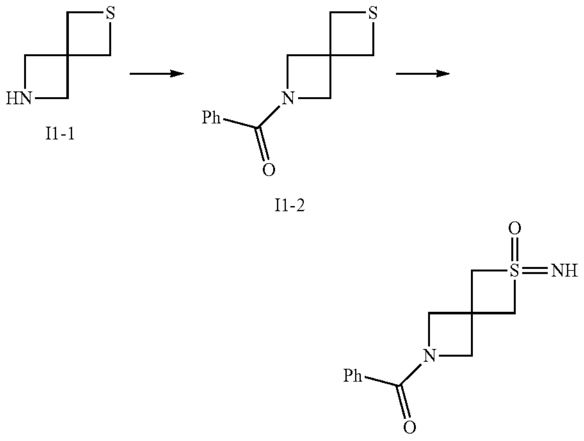

I1-1 I1-2 I1

Step 1: Synthesis of Compound I1-2

Compound I1-1 (500 mg) and triethylamine (790 mg) were dissolved in dichloromethane (20 mL), and a solution of benzoyl chloride (439 mg) in dichloromethane (2 mL) was added dropwise under ice-bath conditions. The mixture was left to react overnight at room temperature. Dichloromethane was added to the reaction solution. The mixture was washed with a saturated aqueous solution of sodium bicarbonate, water and saturated brine successively and dried over anhydrous sodium sulfate. After filtration and concentration, compound I1-2 (0.52 g) was obtained and directly used in the next step.

$^1H$ NMR (500 MHz, $CDCl_3$) δ 7.70-7.57 (m, 2H), 7.51-7.45 (m, 1H), 7.41 (dd, J=8.2, 6.6 Hz, 2H), 4.34-4.23 (m, 4H), 3.51-3.21 (m, 4H).

Step 2: Synthesis of Compound I1

Compound I1-2 was dissolved in methanol (10 mL), and ammonium carbamate (160 mg) and iodobenzene diacetate (925 mg) were added. The mixture was left to react at room temperature for 0.5 h. The reaction solution was filtered and concentrated, and the resulting crude product was separated and purified by column chromatography (dichloromethane:methanol=10:1) to give compound I1 (0.25 g).

$^1H$ NMR (500 MHz, $CDCl_3$) δ 7.67-7.57 (m, 2H), 7.55-7.46 (m, 1H), 7.43 (dd, J=8.2, 6.8 Hz, 2H), 4.48 (s, 4H), 4.30 (s, 4H), 3.20 (s, 1H).

Intermediate 10: Compound J1

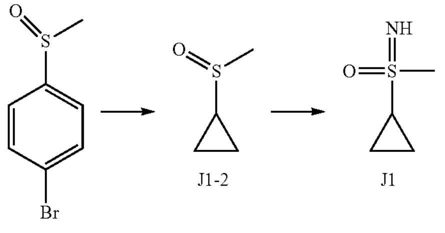

J1-1 J1-2 J1

Step 1: Synthesis of Compound J1-2

Compound J1-1 (1.5 g) was dissolved in tetrahydrofuran (30 mL). The solution was cooled to 0° C., and a 1 M solution of cyclopropylmagnesium bromide in tetrahydrofuran (10.27 mL) was added dropwise under nitrogen atmosphere. The mixture was then left to react at room temperature for 0.5 h. A saturated aqueous solution of ammonium chloride (60 mL) was added, and the mixture was extracted with dichloromethane. The organic phase was dried over anhydrous sodium sulfate. After filtration and concentration, the resulting crude product was separated and purified by column chromatography (petroleum ether:ethyl acetate=0:1) to give compound J1-2 (0.4 g).

$^1H$ NMR (500 MHz, $CDCl_3$) δ 2.65 (s, 3H), 2.16 (tt, J=8.0, 4.9 Hz, 1H), 1.21-1.12 (m, 1H), 1.04-0.91 (m, 2H), 0.88-0.75 (m, 1H).

Step 2: Synthesis of Compound J1

Compound J1-2 (0.4 g) was dissolved in methanol (10 mL), and ammonium carbamate (0.45 g) and iodobenzene diacetate (3.31 g) were added. The mixture was left to react at room temperature for 0.5 h. The reaction solution was filtered and concentrated, and the resulting crude product was separated and purified by column chromatography (dichloromethane:methanol=19:1) to give compound J1 (0.42 g).

$^1H$ NMR (500 MHz, $CDCl_3$) δ 3.04 (s, 3H), 2.81 (brs, 1H), 2.56 (tt, J=7.9, 4.7 Hz, 1H), 1.28-1.11 (m, 2H), 1.09-0.97 (m, 2H).

Intermediate 11: Synthesis of Compound K1

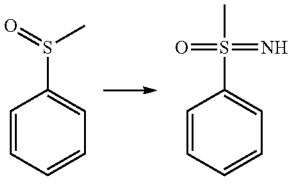

K1-1 K1

Compound K1-1 (1 g), iodobenzene acetate (6.89 g), ammonium carbamate (2.22 g) and methanol (10 mL) were mixed and left to react at room temperature for 1 h. The reaction solution was filtered and concentrated, and the resulting crude product was separated and purified by column chromatography (dichloromethane:methanol=49:1) to give compound K1 (600 mg).

$^1$H NMR (500 MHz, DMSO-$d_6$): δ 7.98-7.88 (m, 2H), 7.66 (t, J=7.3 Hz, 1H), 7.60 (t, J=7.4 Hz, 2H), 3.06 (s, 3H), 1.91 (s, 1H).

Intermediate 12: Compound L1

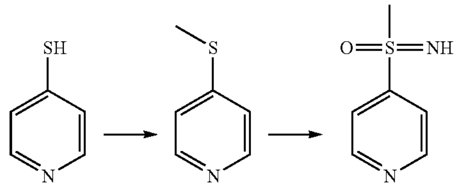

L1-1 L1-2 L1

Step 1: Synthesis of Compound L1-2

Compound L1-1 (3.66 g) and potassium carbonate (9.10 g) were dissolved in dichloromethane (15 mL). The solution was cooled to 0° C., and iodomethane (7.01 g) and triethylamine (0.459 mL) were added dropwise. The mixture was left to react at room temperature for 6 h. A saturated aqueous solution of ammonium chloride was added to the reaction solution. The aqueous phase was extracted with dichloromethane, and the organic phase was washed with water and saturated brine successively and dried over anhydrous sodium sulfate. After filtration and concentration, the resulting crude product was separated and purified by column chromatography (petroleum ether:ethyl acetate=3:1) to give compound L1-2 (3 g).

$^1$HNMR (500 MHz, DMSO-$d_6$) δ 8.37 (dd, J=4.6, 1.6 Hz, 2H), 7.25 (dd, J=4.6, 1.6 Hz, 2H), 2.51 (s, 3H).

Step 2: Synthesis of Compound L1

Compound L1-2 (1 g), iodobenzene acetate (5.15 g) and ammonium carbamate (1.87 g) were dissolved in methanol (10 mL), and the mixture was left to react at room temperature for 1 h. The reaction solution was filtered and concentrated, and the resulting crude product was separated and purified by column chromatography (dichloromethane: methanol=47:3) to give compound L1 (500 mg).

$^1$HNMR (500 MHz, DMSO-$d_6$) δ 8.86 (dd, J=4.4, 1.6 Hz, 2H), 7.87 (dd, J=4.4, 1.6 Hz, 2H), 3.15 (s, 3H).

Intermediate 13: Compound M1

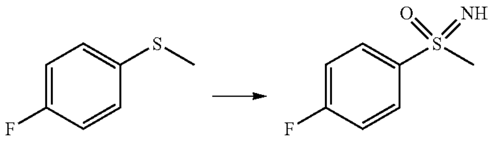

M1-1 M1

Compound M1-1 (500 mg) was dissolved in methanol (10 mL), and ammonium carbamate (412 mg) and iodobenzene diacetate (2.2 g) were added. The mixture was left to react at room temperature for 1 h. The reaction solution was filtered and concentrated, and the resulting crude product was separated and purified by column chromatography (petroleum ether:ethyl acetate=1:1) to give compound M1 (0.31 g).

$^1$H NMR (500 MHz, DMSO-$d_6$) δ 8.00-7.97 (m, 2H), 7.46-7.42 (m, 2H), 4.28 (s, 1H), 3.08 (s, 3H).

Intermediate 14: Compound N1

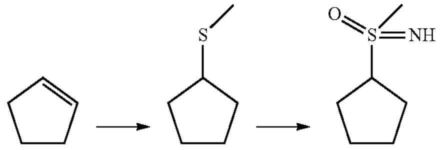

N1-1 N1-2 N1

Step 1: Synthesis of Compound N1-2

Compound N1-1 (150 mg), 1,2-dimethyldisulfone (415 mg), bis[2-(2,4-difluorophenyl)-5-trifluoromethylpyridine][2-2'-bis(4-tert-butylpyridine)]iridium bis(hexafluorophosphate)(49.4 mg) and dichloroethane (22 mL) were mixed and left to react under illumination (5 w, 450 nm) at room temperature for 16 h. The reaction solution was filtered and concentrated, and the resulting crude product was separated and purified by column chromatography (petroleum ether: ethyl acetate=3:1). This experiment was repeated twice. A total of 450 mg of starting material was used, and a total of 150 mg of compound N1-2 was obtained.

Step 2: Synthesis of Compound N1

Compound N1-2 (150 mg) was dissolved in methanol (5 mL), and ammonium carbamate (403 mg) and iodobenzene diacetate (1.24 g) were added. The mixture was left to react at room temperature for 0.5 h. The reaction solution was filtered and concentrated, and the resulting crude product was separated and purified by column chromatography (dichloromethane:methanol=10:1) to give compound N1 (100 mg).

$^1$HNMR (500 MHz, DMSO-$d_6$) (3.48 (dd, J=15.9, 8.1 Hz, 1H), 2.81 (s, 3H), 1.96-1.80 (m, 4H), 1.71-1.61 (m, 2H), 1.60-1.50 (m, 2H).

Intermediate 15: Compound O1

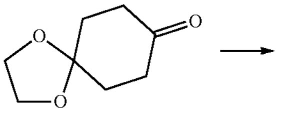

O1-1

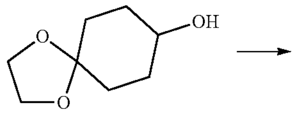

O1-2

-continued

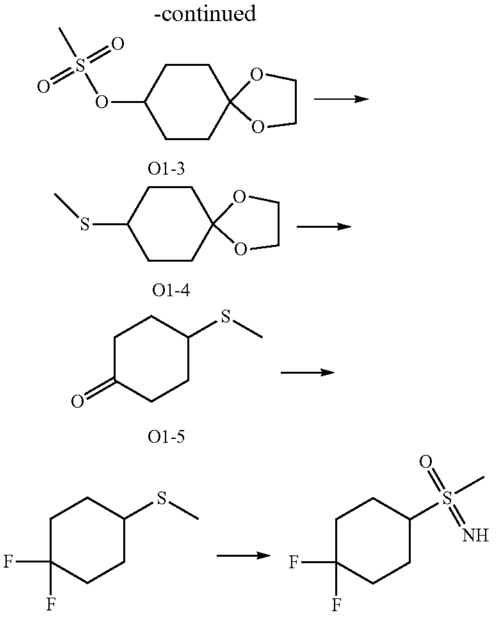

O1-3

O1-4

O1-5

O1-6 O1

Step 1: Synthesis of Compound O1-2

Compound O1-1 (30 g) was dissolved in methanol (182 mL). The solution was cooled to 5° C., and sodium borohydride (2.1 g) was added portionwise. The mixture was left to react at 5° C. for 1 h. Water (100 mL) was added to the reaction solution. The aqueous phase was extracted with dichloromethane, and the organic phase was washed with water and saturated brine successively and dried over anhydrous sodium sulfate. After filtration and concentration, the resulting crude product was separated and purified by column chromatography (petroleum ether:ethyl acetate=5:1) to give compound 01-2 (28 g).

$^1$H-NMR (500 MHz, DMSO-$d_6$): δ 4.46 (d, J=4.1 Hz, 1H), 3.83 (m, 4H), 3.55 (s, 1H), 1.72-1.60 (m, 4H), 1.54-1.38 (m, 4H).

Step 2: Synthesis of Compound O1-3

Compound O1-2 (9 g) was dissolved in dichloromethane (80 mL). The solution was cooled to 5° C., and triethylamine (17.27 g) and methanesulfonyl chloride (7.82 g) were added. The mixture was left to react at 5° C. for 30 min. Water (100 mL) was added to the reaction solution. The aqueous phase was extracted with dichloromethane, and the organic phase was washed with water and saturated brine successively and dried over anhydrous sodium sulfate. After filtration and concentration, the resulting crude product was separated and purified by column chromatography (petroleum ether:ethyl acetate=10:1) to give compound 01-3 (12 g).

$^1$H-NMR (500 MHz, DMSO-$d_6$): δ 4.76 (m, 1H), 3.94-3.71 (m, 4H), 3.18 (s, 3H), 1.89 (m, 2H), 1.84-1.74 (m, 2H), 1.69 (m, 2H), 1.60 (m, 2H).

Step 3: Synthesis of Compound O1-4

Compound O1-3 (12.2 g) was dissolved in N,N-dimethylformamide (100 mL). The solution was cooled to 5° C., and sodium thiomethoxide (4.16 g) was added portionwise. The mixture was slowly warmed to room temperature and left to react overnight. Water (200 mL) was added, and the mixture was extracted with ethyl acetate. The organic phase was washed with water and saturated sodium chloride successively, dried over anhydrous sodium sulfate, and concentrated. The crude product was then separated and purified by column chromatography (petroleum ether:ethyl acetate=5:1) to give compound O1-4 (9 g).

MS (ESI, $[M+H]^+$) m/z: 189.22.

Step 4: Synthesis of Compound O1-5

Compound O1-4 (9 g) was dissolved in ethyl acetate (85 mL), and 3N hydrochloric acid (9 mL) was added dropwise. The mixture was left to react at room temperature for 30 min. Water (50 mL) was added, and the mixture was extracted with ethyl acetate. The organic phase was washed with water and saturated sodium chloride successively, dried over anhydrous sodium sulfate, and concentrated to give compound O1-5 (5.6 g).

$^1$H NMR (500 MHz, DMSO-$d_6$) δ 3.07 (m, 1H), 2.38 (m, 2H), 2.30 (m, 2H), 2.21-2.14 (m, 2H), 2.10 (s, 3H), 1.73 (m, 2H).

Step 5: Synthesis of Compound O1-6

Compound O1-5 (5 g) was dissolved in dichloromethane (50 mL). The solution was cooled to 0° C., and diethylaminosulfur trifluoride (11.18 g) was added dropwise to the reaction solution. The mixture was left to react at 0° C. for 3 h. A saturated aqueous solution of sodium bicarbonate (50 mL) was added, and the mixture was extracted with dichloromethane. The organic phase was washed with water and saturated sodium chloride successively, dried over anhydrous sodium sulfate, and concentrated. The crude product was then separated and purified by column chromatography (petroleum ether:ethyl acetate=5:1) to give compound 01-6 (3.5 g).

$^1$H NMR (500 MHz, DMSO-$d_6$) δ 3.13 (t, J=10.1 Hz, 1H), 2.06 (s, 3H), 1.93-1.79 (m, 3H), 1.60 (dd, J=20.3, 10.4 Hz, 3H), 1.13 (m, 2H).

Step 6: Synthesis of Compound O1

Compound O1-6 (250 mg) was dissolved in methanol (5 mL), and ammonium carbamate (470 mg) and iodobenzene diacetate (1.45 g) were added. The mixture was left to react at room temperature for 1 h. The reaction solution was filtered and concentrated, and the resulting crude product was separated and purified by column chromatography (dichloromethane:methanol=15:1) to give compound O1 (200 mg).

MS (ESI, $[M+H]^+$) m/z: 198.02.

$^1$HNMR (500 MHz, DMSO-$d_6$) δ 3.11 (dd, J=21.0, 9.2 Hz, 1H), 2.86 (s, 3H), 2.20-2.11 (m, 4H), 1.95 (d, J=15.0 Hz, 1H), 1.84 (d, J=21.8 Hz, 1H), 1.74-1.55 (m, 3H).

Intermediate 16: Synthesis of Compound P1

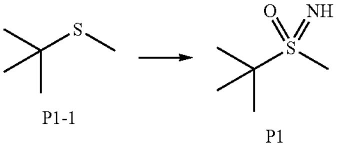

P1-1 P1

Compound P1-1 (0.5 g), methanol (10 mL), ammonium carbamate (0.56 g) and iodobenzene diacetate (3.09 g) were mixed and left to react at room temperature for 5 h. The reaction solution was filtered and concentrated, and the resulting crude product was separated and purified by column chromatography (dichloromethane:methanol=16:1) to give compound P1 (0.416 g).

$^1H$ NMR (500 MHz, DMSO-$d_6$) δ 2.77 (s, 3H), 1.90 (s, 1H), 1.30 (s, 9H).

Intermediate 17: Synthesis of Compound Q1

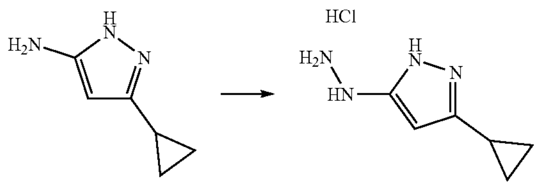

Q1-1 Q1

Compound Q1-1 (54 g) was dissolved in an aqueous solution of hydrochloric acid (6 M, 160 mL). The mixture was cooled to 5° C., and an aqueous solution of sodium nitrite (1 M, 45 mL) was added dropwise. After 1 h of reaction, a solution of stannous chloride in aqueous hydrochloric acid (1 M, 74 mL) was added dropwise to the mixture. The mixture was left to react overnight at room temperature. The reaction solution was concentrated, and the resulting crude product was slurried with ethyl acetate (100 mL), then filtered, and the filter cake was dried to give the hydrochloride of compound Q1 (40 g, crude). The product was directly used in the next step.

MS (ESI, $[M+H]^+$) m/z: 139.10.

Example 1: Synthesis of Compound 1

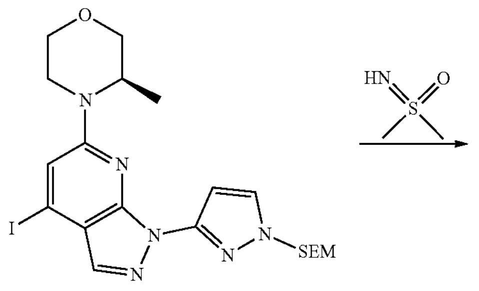

A1

-continued

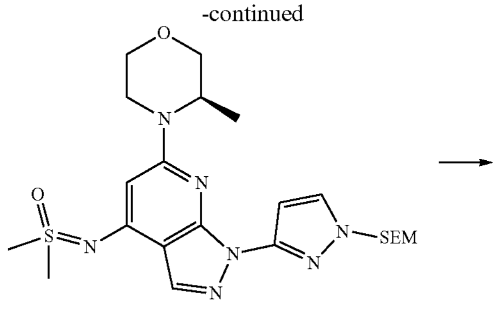

1-1

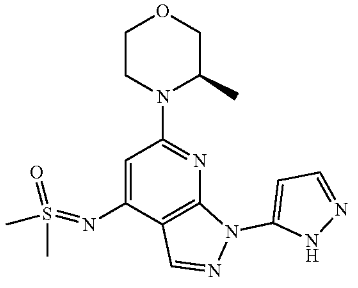

1

Step 1: Synthesis of Compound 1-1

Compound A1 (100 mg), dimethylsulfoximine (20.68 mg), tris(dibenzylideneacetone)dipalladium (8.47 mg), 4,5-bisdiphenylphosphino-9,9-dimethylxanthene (10.71 mg), cesium carbonate (121 mg) and 1,4-dioxane (5 mL) were mixed and left to react at 80° C. for 1 h under nitrogen atmosphere. The reaction solution was filtered, and the filtrate was concentrated. The crude product was then separated and purified by column chromatography (dichloromethane:methanol=9:1) to give compound 1-1 (71 mg).

$^1H$ NMR (500 MHz, $CDCl_3$): δ 8.07 (s, 1H), 7.63 (d, J=2.0 Hz, 1H), 6.60 (d, J=2.0 Hz, 1H), 6.26 (s, 1H), 5.76-5.70 (m, 2H), 4.32-4.30 (m, 1H), 4.00-3.91 (m, 2H), 3.78-3.70 (m, 2H), 3.59-3.54 (m, 1H), 3.46-3.42 (m, 2H), 3.28 (d, J=1.5 Hz, 6H), 3.25-3.19 (m, 1H), 1.26 (d, J=7.0 Hz, 3H), 0.79-0.75 (m, 2H), −0.14 (s, 9H).

Step 2: Synthesis of Compound 1

Compound 1-1 (350 mg) was dissolved in dichloromethane (4 mL). The solution was cooled to 0° C., and triethylsilane (805 mg) and trifluoroacetic acid (1 mL) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was purified by column chromatography (dichloromethane:methanol=9:1) to give compound 1 (212 mg).

MS (ESI, $[M+H]^+$) m/z: 376.30.

$^1H$ NMR (500 MHz, DMSO-$d_6$): δ 12.73 (s, 1H), 7.89 (s, 1H), 7.80 (s, 1H), 6.78 (s, 1H), 6.18 (s, 1H), 4.33 (d, J=5.5 Hz, 1H), 3.97-3.91 (m, 2H), 3.75 (d, J=11.5 Hz, 1H), 3.64 (dd, J=11.3, 2.8 Hz, 1H), 3.49 (td, J=11.8, 2.8 Hz, 1H), 3.41 (s, 6H), 3.13 (td, J=12.5, 3.5 Hz, 1H), 1.18 (d, J=7.0 Hz, 3H).

Example 2: Synthesis of Compound 2

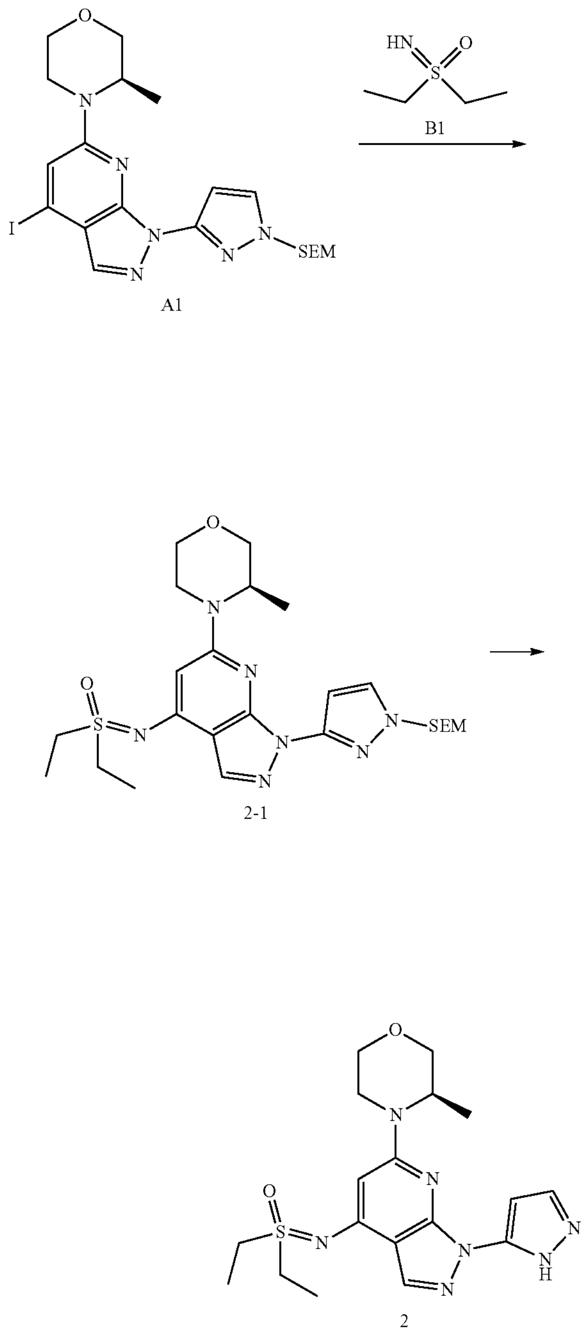

Compound 2 (90 mg) was synthesized in a similar manner to that described in Example 1 using compound B1 in place of the dimethylsulfoximine of step 1 in Example 1.

MS (ESI, $[M+H]^+$) m/z: 404.27.

$^1$H NMR (500 MHz, DMSO-$d_6$): δ 12.73 (s, 1H), 7.92 (s, 1H), 7.81 (s, 1H), 6.79 (s, 1H), 6.22 (s, 1H), 4.29 (d, J=4.8 Hz, 1H), 3.97-3.89 (m, 2H), 3.74 (d, J=11.3 Hz, 1H), 3.64 (d, J=11.3 Hz, 1H), 3.48 (dd, J=14.7, 7.5 Hz, 5H), 3.11 (t, J=12.6 Hz, 1H), 1.32 (td, J=7.3, 2.8 Hz, 6H), 1.16 (d, J=6.6 Hz, 3H).

Example 3: Synthesis of Compound 3

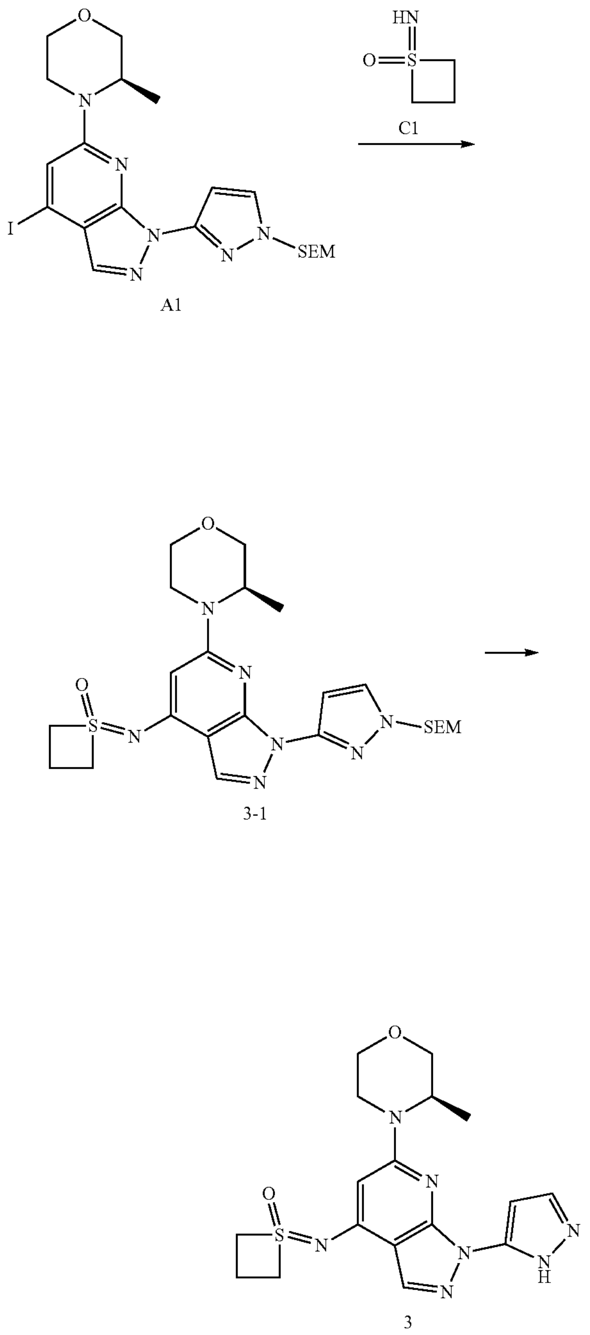

Compound 3 (80 mg) was synthesized in a similar manner to that described in Example 1 using compound C1 in place of the dimethylsulfoximine of step 1 in Example 1.

MS (ESI, [M+H]) m/z: 388.12.

$^1$H NMR (500 MHz, DMSO-$d_6$): δ 12.75 (s, 1H), 7.91 (s, 1H), 7.82 (s, 1H), 6.79 (s, 1H), 6.02 (s, 1H), 4.54-4.39 (m, 2H), 4.39-4.27 (m, 3H), 3.99-3.83 (m, 2H), 3.74 (d, J=11.3 Hz, 1H), 3.64 (dd, J=11.3, 2.4 Hz, 1H), 3.49 (td, J=11.7, 2.4 Hz, 1H), 3.12 (td, J=12.5, 2.8 Hz, 1H), 2.45-2.33 (m, 1H), 2.28 (dd, J=18.9, 9.2 Hz, 1H), 1.17 (d, J=6.6 Hz, 3H).

Example 4: Synthesis of Compound 4

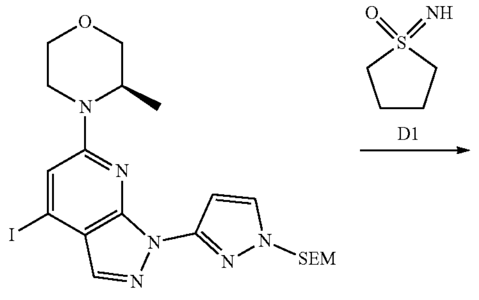

A1

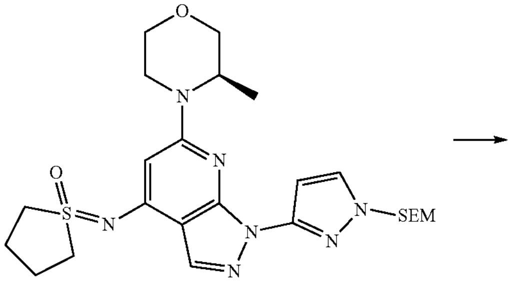

4-1

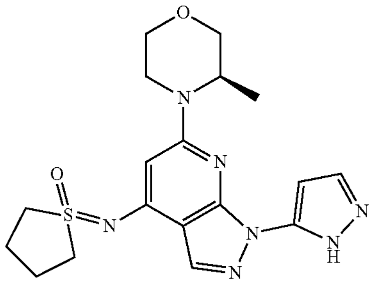

4

Compound 4 (46 mg) was synthesized in a similar manner to that described in Example 1 using compound D1 in place of the dimethylsulfoximine of step 1 in Example 1.

MS (ESI, $[M+H]^+$) m/z: 402.15.

$^1$H NMR (500 MHz, $CDCl_3$) δ 8.03 (s, 1H), 7.64 (s, 1H), 6.87 (s, 1H), 6.17 (s, 1H), 4.34-4.33 (m, 1H), 4.03-4.00 (m, 1H), 3.93-3.91 (m, 1H), 3.81-3.73 (m, 2H), 3.60-3.58 (m, 1H), 3.52-3.48 (m, 2H), 3.31-3.25 (m, 3H), 2.36-2.31 (m, 4H), 1.27 (d, J=7.0 Hz, 3H).

Example 5: Synthesis of Compound 5

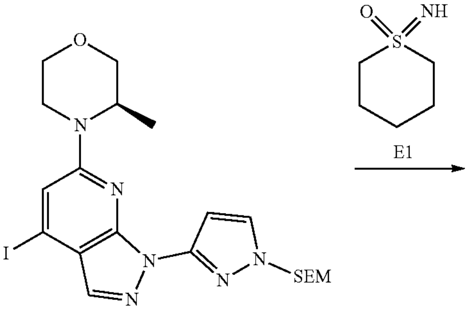

A1

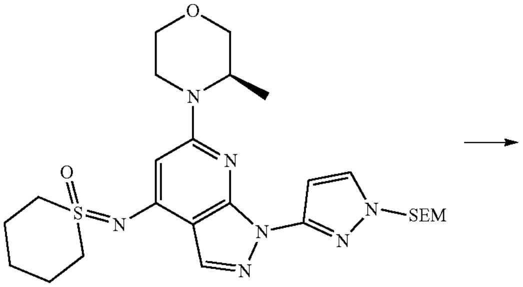

5-1

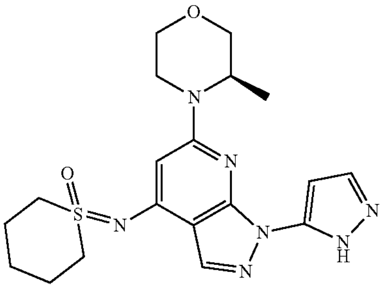

5

Compound 5 (94 mg) was synthesized in a similar manner to that described in Example 1 using compound E1 in place of the dimethylsulfoximine of step 1 in Example 1.

MS (ESI, $[M+H]^+$) m/z: 416.17.

$^1$H NMR (500 MHz, $CDCl_3$) δ 11.84 (s, 1H), 8.09 (s, 1H), 7.66 (d, J=2.2 Hz, 1H), 6.82 (s, 1H), 6.31 (s, 1H), 4.42-4.31 (m, 1H), 4.04 (dd, J=11.4, 3.7 Hz, 1H), 4.00-3.91 (m, 1H), 3.87-3.75 (m, 2H), 3.63 (td, J=11.8, 3.1 Hz, 1H), 3.56-3.44 (m, 2H), 3.32 (td, J=12.7, 3.9 Hz, 1H), 3.21-3.16 (m, 2H), 2.14-2.10 (m, 4H), 1.84-1.79 (m, 1H), 1.66-1.59 (m, 1H), 1.32 (d, J=6.8 Hz, 3H).

Example 6: Synthesis of Compound 6
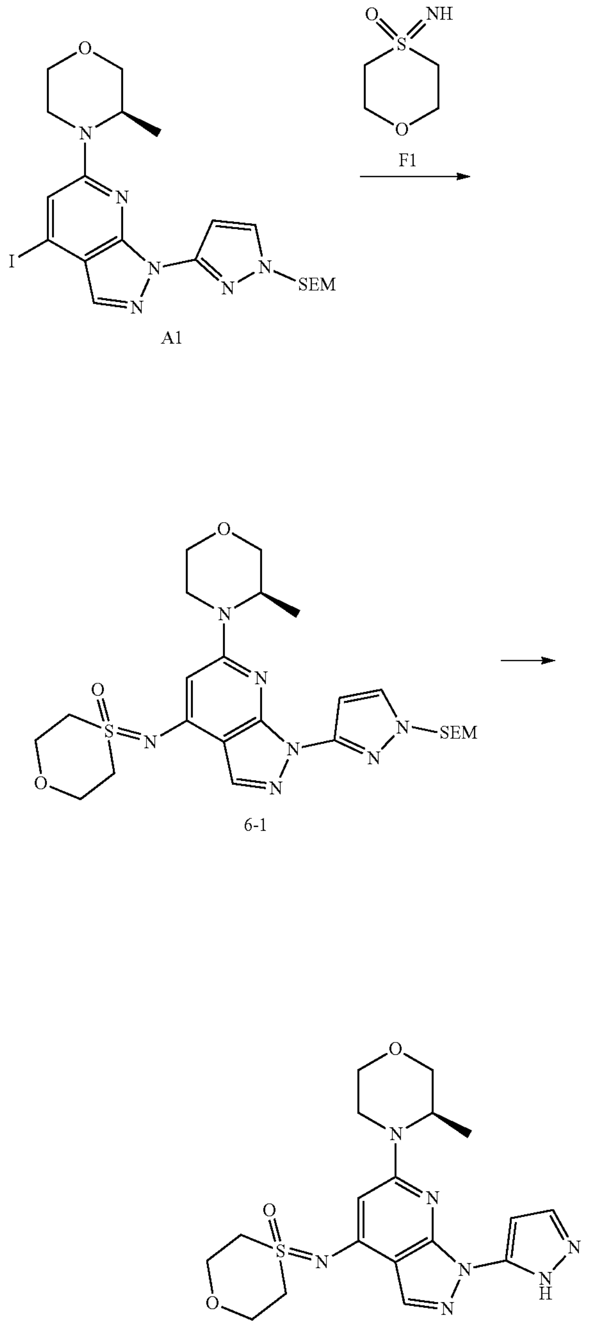
A1
6-1
6
Compound 6 (58 mg) was synthesized in a similar manner to that described in Example 1 using compound F1 in place of the dimethylsulfoximine of step 1 in Example 1.
MS (ESI, $[M+H]^+$) m/z: 418.26.
$^1$H NMR (500 MHz, $CDCl_3$) δ 8.01 (s, 1H), 7.68 (s, 1H), 6.90 (s, 1H), 6.25 (s, 1H), 4.37-4.36 (m, 1H), 4.22-4.19 (m, 2H), 4.05-4.03 (m, 3H), 3.96-3.94 (m, 1H), 3.82-3.80 (m, 1H), 3.76-3.74 (m, 1H), 3.62-3.58 (m, 1H), 3.50-3.47 (m, 2H), 3.33-3.30 (m, 3H), 1.29 (d, J=6.5 Hz, 3H).
Example 7: Synthesis of Compound 7-1
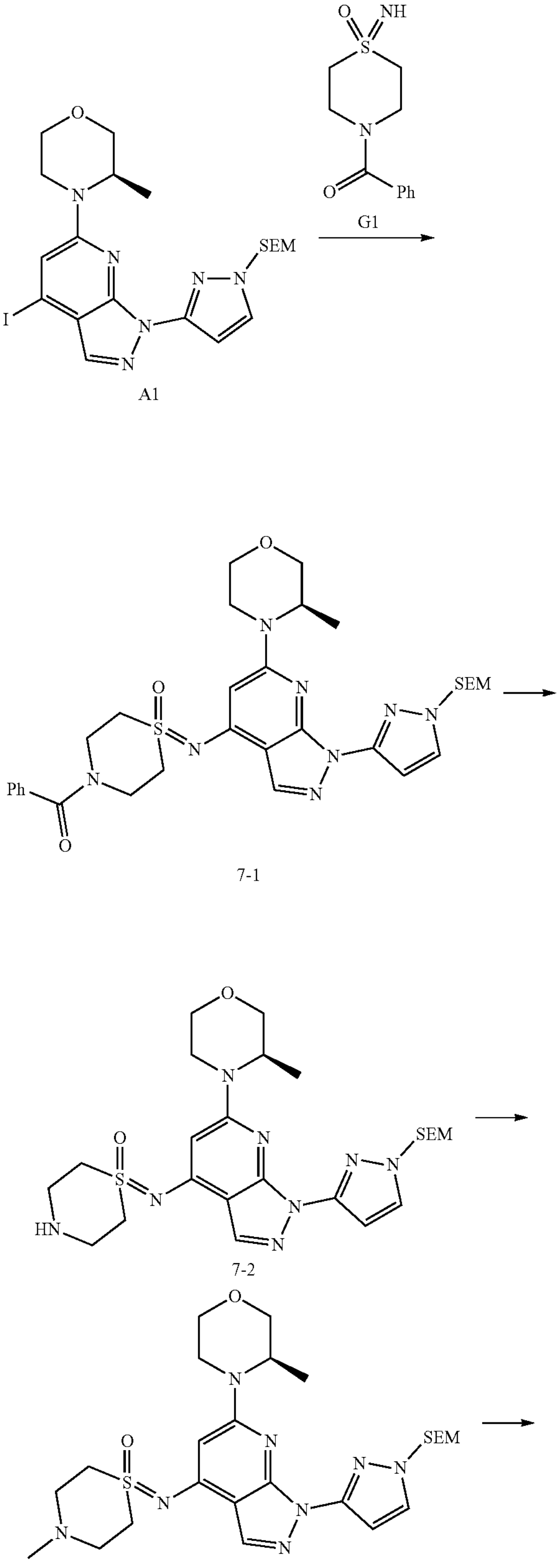
A1
7-1
7-2
7-3

-continued

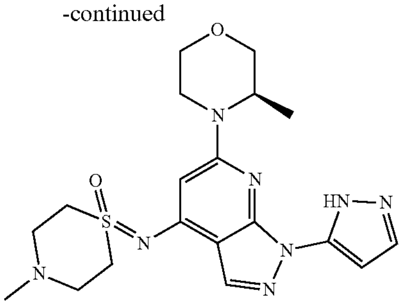

7

Step 1: Synthesis of Compound 7-1

Compound A1, compound G1 (183 mg), tris(dibenzylideneacetone)dipalladium (27.1 mg), 4,5-bisdiphenylphosphino-9,9-dimethylxanthene (34.3 mg), cesium carbonate (386 mg) and dioxane (10 mL) were mixed and then left to react at 80° C. for 1 h under nitrogen atmosphere. The reaction solution was filtered, and the filtrate was concentrated. The crude product was then separated and purified by column chromatography (dichloromethane:methanol=19:1) to give compound 7-1 (0.37 g).

$^1$H NMR (500 MHz, $CDCl_3$) δ 8.11 (s, 1H), 7.63 (d, J=1.9 Hz, 1H), 7.51-7.43 (m, 5H), 6.60 (d, J=1.9 Hz, 1H), 6.27 (s, 1H), 5.82-5.65 (m, 2H), 4.33-4.29 (m, 1H), 3.99 (dd, J=11.4, 3.7 Hz, 1H), 3.91 (dd, J=13.3, 2.9 Hz, 1H), 3.88-3.82 (m, 2H), 3.78-3.69 (m, 2H), 3.56 (td, J=11.9, 3.2 Hz, 2H), 3.48-3.44 (m, 3H), 3.22 (td, J=12.7, 3.9 Hz, 3H), 1.57 (s, 2H), 1.26 (d, J=6.7 Hz, 3H), 0.77 (dd, J=9.5, 7.2 Hz, 2H), 0.14 (s, 9H).

Step 2: Synthesis of Compound 7-2

Compound 7-1 (200 mg) was dissolved in tetrahydrofuran (6 mL), and a 2.5 M solution of lithium aluminum hydride in tetrahydrofuran (0.18 mL) was added dropwise under nitrogen atmosphere. The mixture was left to react at room temperature for 1 h. The reaction mixture was diluted with ethyl acetate, washed with water and saturated brine successively and dried over anhydrous sodium sulfate. After filtration and concentration, the resulting crude product was separated and purified by column chromatography (dichloromethane:methanol=10:1) to give compound 7-2 (0.1 g).

$^1$H NMR (500 MHz, $CDCl_3$) δ 8.12 (s, 1H), 7.63 (d, J=1.9 Hz, 1H), 6.61 (d, J=1.8 Hz, 1H), 6.29 (s, 1H), 5.85-5.65 (m, 2H), 4.32 (dd, J=7.2, 2.9 Hz, 1H), 3.99 (dd, J=11.4, 3.8 Hz, 1H), 3.93 (dd, J=13.2, 2.9 Hz, 1H), 3.77 (d, J=11.3 Hz, 1H), 3.72 (dd, J=11.3, 3.1 Hz, 1H), 3.57 (td, J=11.9, 3.1 Hz, 1H), 3.52-3.42 (m, 4H), 3.40-3.36 (m, 2H), 3.34-3.28 (m, 2H), 3.25-3.19 (m, 3H), 1.76-1.67 (m, 1H), 1.26 (d, J=6.6 Hz, 3H), 0.81-0.72 (m, 2H), 0.14 (s, 9H).

Step 3: Synthesis of Compound 7-3

Compound 7-2 (70 mg) was dissolved in methanol (2 mL), and acetic acid (16.09 mg), a 37% aqueous solution of formaldehyde (104 mg) and sodium cyanoborohydride (16.09 mg) were sequentially added. The mixture was left to react at room temperature for 1 h. Triethylamine was added to adjust the pH to about 8. After concentration, the resulting crude product was separated and purified by column chromatography (dichloromethane:methanol=19:1) to give compound 7-3 (0.096 g).

$^1$H NMR (500 MHz, $CDCl_3$) δ 8.12 (s, 1H), 7.63 (d, J=1.8 Hz, 1H), 6.61 (d, J=1.8 Hz, 1H), 6.27 (s, 1H), 5.92-5.63 (m, 2H), 4.32 (dd, J=7.2, 2.8 Hz, 1H), 3.99 (dd, J=11.4, 3.7 Hz, 1H), 3.97-3.88 (m, 1H), 3.77 (d, J=11.3 Hz, 1H), 3.72 (dd, J=11.3, 3.1 Hz, 1H), 3.57 (td, J=11.9, 3.1 Hz, 1H), 3.50-3.43 (m, 4H), 3.34 (ddd, J=13.6, 9.7, 3.3 Hz, 2H), 3.22 (td, J=12.7, 3.9 Hz, 1H), 3.08-2.95 (m, 2H), 2.95-2.84 (m, 2H), 2.43 (s, 3H), 1.26 (d, J=6.7 Hz, 3H), 0.82-0.71 (m, 2H), 0.14 (s, 9H).

Step 4: Synthesis of Compound 7

Compound 7-3 (70 mg) was dissolved in dichloromethane (5 mL), and triethylsilane (145 mg) and trifluoroacetic acid (2.277 g) were sequentially added. The mixture was left to react at room temperature for 0.5 h. The reaction solution was diluted with dichloromethane and made neutral by adding a saturated solution of sodium bicarbonate under ice-bath conditions. The organic phase was washed with water and saturated brine successively and dried over anhydrous sodium sulfate. After filtration and concentration, the resulting crude product was separated and purified by column chromatography (dichloromethane:methanol=10:1) to give compound 7 (0.048 g).

MS (ESI, [M+H]$^+$) m/z: 431.27.

$^1$H NMR (500 MHz, $CDCl_3$) δ 11.56 (brs, 1H), 8.10 (s, 1H), 7.63 (d, J=2.1 Hz, 1H), 6.84-6.76 (m, 1H), 6.30 (s, 1H), 4.41-4.33 (m, 1H), 4.05 (dd, J=11.4, 3.7 Hz, 1H), 3.95 (dd, J=13.1, 2.9 Hz, 1H), 3.85-3.74 (m, 2H), 3.63 (td, J=11.8, 3.1 Hz, 1H), 3.51-3.46 (m, 2H), 3.37-3.30 (m, 3H), 3.08-2.97 (m, 2H), 2.93-2.88 (m, 2H), 2.43 (s, 3H), 1.32 (d, J=6.7 Hz, 3H).

Example 8: Synthesis of Compound 8

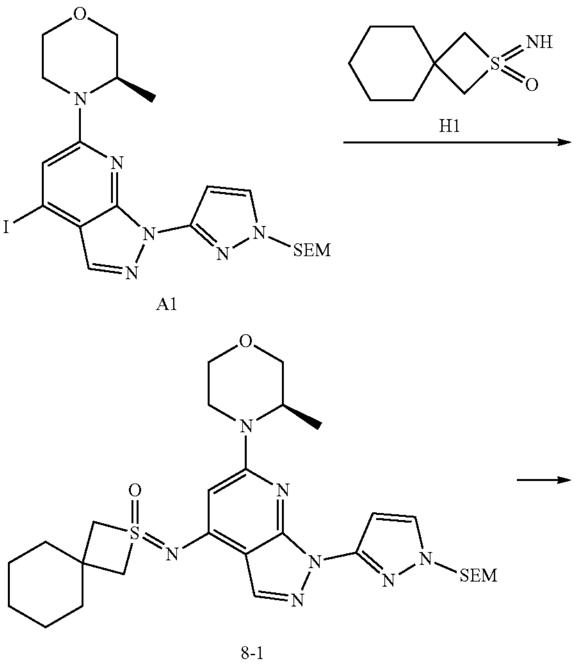

-continued

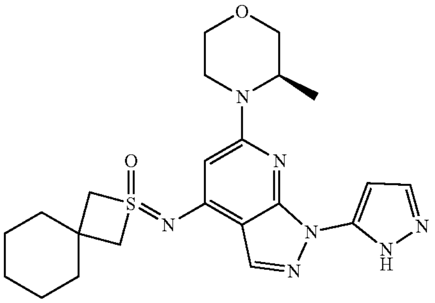

8

Compound 8 (68 mg) was synthesized in a similar manner to that described in Example 1 using compound H1 in place of the dimethylsulfoximine of step 1 in Example 1.

MS (ESI, $[M+H]^+$) m/z: 456.15.

$^1$H NMR (500 MHz, $CDCl_3$) δ 11.37 (brs, 1H), 8.03 (s, 1H), 7.62 (d, J=2.1 Hz, 1H), 6.87-6.70 (m, 1H), 6.14 (s, 1H), 4.42-4.28 (m, 1H), 4.07-3.98 (m, 3H), 3.97-3.89 (m, 3H), 3.86-3.75 (m, 2H), 3.64 (td, J=11.8, 3.1 Hz, 1H), 3.33 (td, J=12.6, 3.9 Hz, 1H), 1.91-1.80 (m, 4H), 1.51-1.46 (m, 6H), 1.32 (d, J=6.8 Hz, 3H).

Example 9: Synthesis of Compound 9

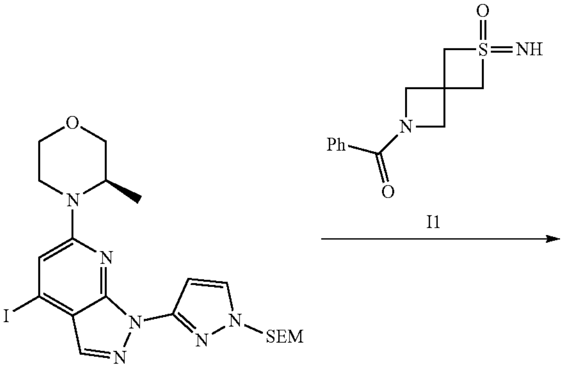

I1

A1

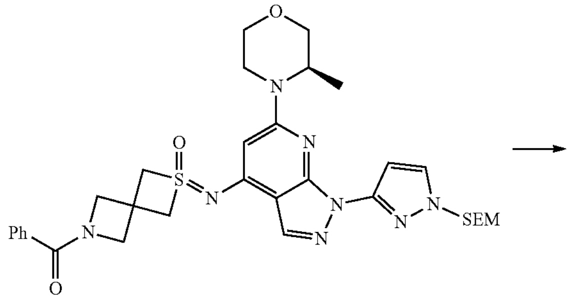

9-1

-continued

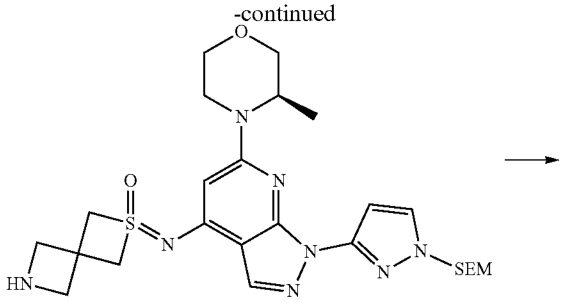

9-2

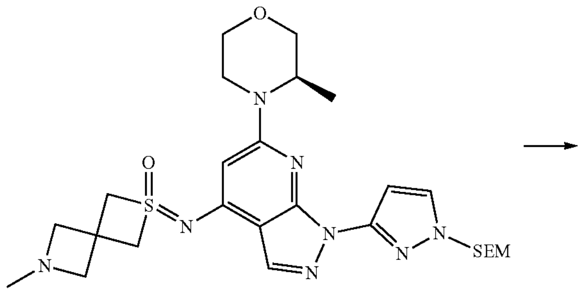

9-3

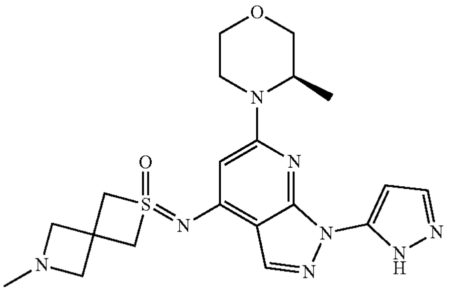

9

Step 1: Synthesis of Compound 9-1

Compound A1, compound I1 (168 mg), tris(dibenzylideneacetone)dipalladium (28 mg), 4,5-bisdiphenylphosphino-9,9-dimethylxanthene (35.3 mg), cesium carbonate (597 mg) and dioxane (10 mL) were mixed and left to react at 80° C. for 1 h under nitrogen atmosphere. The reaction solution was filtered, and the filtrate was concentrated. The resulting crude product was then separated and purified by column chromatography (dichloromethane:methanol=19:1) to give compound 9-1 (0.39 g).

$^1$H NMR (500 MHz, $CDCl_3$) δ 7.99 (s, 1H), 7.67-7.57 (m, 3H), 7.55-7.46 (m, 1H), 7.44 (dd, J=8.2, 6.8 Hz, 2H), 6.60 (d, J=1.9 Hz, 1H), 6.10 (s, 1H), 5.79-5.66 (m, 2H), 4.60-4.39 (m, 8H), 4.30 (d, J=7.5 Hz, 1H), 3.99 (dd, J=11.4, 3.7 Hz, 1H), 3.93-3.85 (m, 1H), 3.80-3.68 (m, 2H), 3.56 (td, J=11.8, 3.1 Hz, 1H), 3.49-3.42 (m, 2H), 3.22 (td, J=12.7, 3.9 Hz, 1H), 1.26 (d, J=6.7 Hz, 3H), 0.77 (dd, J=9.5, 7.2 Hz, 2H), 0.14 (s, 9H).

Step 2: Synthesis of Compound 9-2

Compound 9-1 (330 mg) was dissolved in tetrahydrofuran (11 mL). A 2.5 M solution of lithium aluminum hydride in tetrahydrofuran (0.30 mL) was added dropwise under nitrogen atmosphere. The mixture was left to react at room temperature for 1 h. Ethyl acetate was added to the reaction solution. The mixture was washed with water and saturated brine successively and dried over anhydrous sodium sulfate. After filtration and concentration, the resulting crude product was separated and purified by column chromatography (dichloromethane:methanol=9:1) to give compound 9-2 (0.16 g).

$^1$H NMR (500 MHz, $CDCl_3$) δ 8.01 (s, 1H), 7.63 (d, J=1.9 Hz, 7.55-7.6 (d, J=1.9 Hz, 1H), 6.11 (s, 1H), 5.76-5.70 (m, 2H), 4.46-4.37 (m, 4H), 4.33-4.30 (m, 1H), 3.99 (dd, J=11.4, 3.7 Hz, 1H), 3.93-3.85 (m, 5H), 3.77 (d, J=11.3 Hz, 1H), 3.72 (dd, J=11.3, 3.1 Hz, 1H), 3.57 (td, J=11.8, 3.1 Hz, 1H), 3.49-3.41 (m, 2H), 3.22 (td, J=12.7, 3.8 Hz, 1H), 1.26 (d, J=6.6 Hz, 3H), 0.81-0.72 (m, 2H), 0.14 (s, 9H).

Step 3: Synthesis of Compound 9-3

Compound 9-2 (120 mg) was dissolved in methanol (10 mL), and acetic acid (25.8 mg), a 37% aqueous solution of formaldehyde (174 mg) and sodium cyanoborohydride (27 mg) were sequentially added. The mixture was left to react at room temperature for 1 h. The reaction mixture was made alkaline by adding triethylamine, and ethyl acetate was added. The mixture was washed with water and saturated brine successively. After filtration, the filtrate was concentrated to give compound 9-3. The product was directly used in the next step.

Step 4: Synthesis of Compound 9

Compound 9-3 (0.11 g) was dissolved in dichloromethane (5 mL), and triethylsilane (0.22 g) and trifluoroacetic acid (3.5 g) were added. The mixture was left to react at room temperature for 0.5 h. Dichloromethane was added to the reaction solution, and the mixture was made neutral by adding a saturated aqueous solution of sodium bicarbonate under ice-bath conditions. The organic phase was washed with water and saturated brine successively and dried over anhydrous sodium sulfate. After filtration and concentration, the resulting crude product was separated and purified by column chromatography (dichloromethane:methanol=10:1) to give compound 9 (0.065 g).

MS (ESI) m/z: 443.20 [M+H]$^+$.

$^1$H NMR (500 MHz, $CDCl_3$) δ 7.99 (s, 1H), 7.63 (d, J=2.1 Hz, 1H), 6.81 (s, 1H), 6.13 (s, 1H), 4.47-4.25 (m, 5H), 4.04 (dd, J=11.4, 3.8 Hz, 1H), 3.94 (dd, J=13.0, 3.0 Hz, 1H), 3.86-3.73 (m, 2H), 3.63 (td, J=11.8, 3.1 Hz, 1H), 3.43 (s, 4H), 3.32 (td, J=12.6, 3.9 Hz, 1H), 2.33 (s, 3H), 1.31 (d, J=6.8 Hz, 3H).

Example 10: Synthesis of Compound 10-A and Compound 10-B

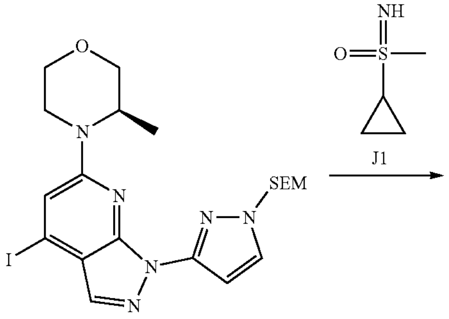

A1 J1

-continued

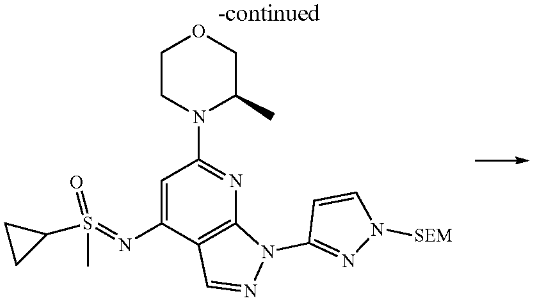

10-1

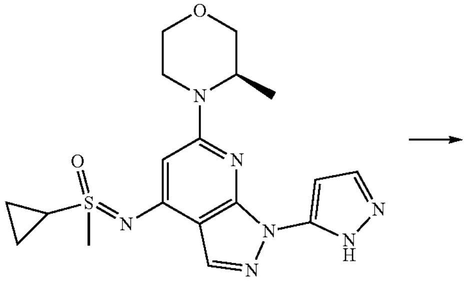

10-2

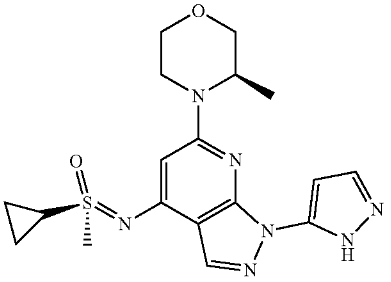

10-A or 10-B

+

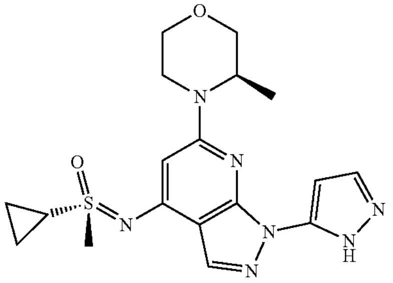

10-B or 10-A (1) Compound 10-2 (110 mg) was synthesized in a similar manner to that described in Example 1 using compound J1 in place of the dimethylsulfoximine of step 1 in Example 1. The above compound 10-2 was prepared and separated by chiral HPLC (mobile phase: n-hexane:ethanol=70:30; flow rate: 40 mL/min; column temperature: 22° C.; column: CHIRALART Amylose-SB 30x250) to give compound 10-A (42 mg) and compound 10-B (39 mg) sequentially.

Compound 10-A: $R_t$=15.9 min.

HRMS: (ESI, [M+H]$^+$) m/z: 402.1712.

$^1$H NMR (500 MHz, $CDCl_3$) δ 11.67 (brs, 1H), 8.06 (s, 1H), 7.64 (d, J=2.1 Hz, 1H), 6.79 (s, 1H), 6.29 (s, 1H), 4.43-4.23 (m, 1H), 4.05 (dd, J=11.4, 3.7 Hz, 1H), 3.94 (dd, J=12.9, 2.9 Hz, 1H), 3.86-3.75 (m, 2H), 3.64 (td, J=11.8, 3.1 Hz, 1H), 3.32 (td, J=12.6, 3.9 Hz, 1H), 3.23 (s, 3H), 2.70-2.65 (m, 1H), 1.51-1.46 (m, 1H), 1.31 (d, J=6.7 Hz, 4H), 1.23-1.18 (m, 1H), 1.18-1.09 (m, 1H).

Compound 10-B: $R_t$=26.3 min.

HRMS: (ESI, [M+H]$^+$) m/z: 402.1706.

$^1H$ NMR (500 MHz, $CDCl_3$) δ 7.99 (s, 1H), 7.71-7.39 (m, 1H), 6.94-6.61 (m, 1H), 6.22 (s, 1H), 4.38-4.16 (m, 1H), 3.97 (dd, J=11.3, 3.7 Hz, 1H), 3.91 (dd, J=13.2, 2.9 Hz, 1H), 3.79-3.67 (m, 2H), 3.56 (td, J=11.9, 3.1 Hz, 1H), 3.24 (td, J=12.7, 3.8 Hz, 1H), 3.17 (s, 3H), 2.62-2.59 (m, 1H), 1.44-1.39 (m, 1H), 1.24 (d, J=6.7 Hz, 4H), 1.14-1.10 (m, 1H), 1.07-1.05 (m, 1H).

or (2) Compound 10-2 (110 mg) was synthesized in a similar manner to that described in Example 1 using compound J1 in place of the dimethylsulfoximine of step 1 in Example 1. The above compound 10-2 was prepared and separated by SFC (mobile phase: carbon dioxide:ethanol=65:35; flow rate: 60 mL/min; column temperature: 35° C.; column: CHIRALART Cellulose-SB 30×250) to give compound 10-A (42 mg) and compound 10-B (39 mg) sequentially.

Compound 10-A: $R_t$=2.4 min.

HRMS: (ESI, $[M+H]^+$) m/z: 402.1712.

$^1H$ NMR (500 MHz, $CDCl_3$) δ 11.67 (brs, 1H), 8.06 (s, 1H), 7.64 (d, J=2.1 Hz, 1H), 6.79 (s, 1H), 6.29 (s, 1H), 4.39-4.34 (m, 1H), 4.05 (dd, J=11.4, 3.7 Hz, 1H), 3.94 (dd, J=12.9, 2.9 Hz, 1H), 3.86-3.75 (m, 2H), 3.64 (td, J=11.8, 3.1 Hz, 1H), 3.32 (td, J=12.6, 3.9 Hz, 1H), 3.23 (s, 3H), 2.70-2.65 (m, 1H), 1.51-1.46 (m, 1H), 1.33-1.30 (m, 4H), 1.23-1.18 (m, 1H), 1.18-1.09 (m, 1H).

Compound 10-B: $R_t$=3.5 min.

HRMS: (ESI, $[M+H]^+$) m/z: 402.1706.

$^1H$ NMR (500 MHz, DMSO-$d_6$) δ 12.74 (s, 1H), 7.90 (s, 1H), 7.81 (s, 1H), 6.79 (s, 1H), 6.20 (s, 1H), 4.26-4.24 (m, 1H), 3.98-3.92 (m, 2H), 3.75 (d, J=11.2 Hz, 1H), 3.64 (dd, J=11.3, 3.0 Hz, 1H), 3.48 (td, J=11.8, 3.1 Hz, 1H), 3.39 (s, 3H), 3.11 (td, J=12.8, 3.9 Hz, 1H), 3.00-2.95 (m, 1H), 1.36-1.31 (m, 1H), 1.22-1.11 (m, 6H).

Example 11: Synthesis of Compound 11-A and Compound 11-B

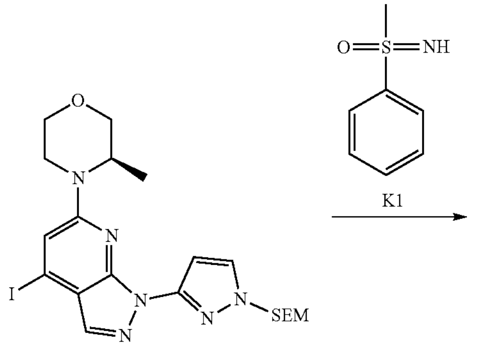
A1
K1

-continued

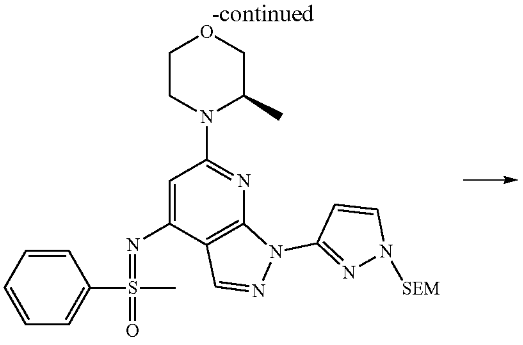
11-1

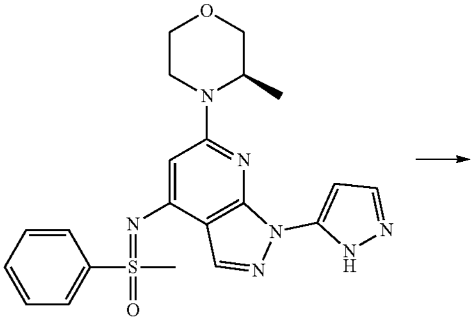
11-2

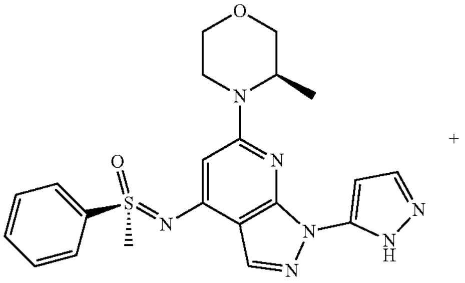
11-A or 11-B

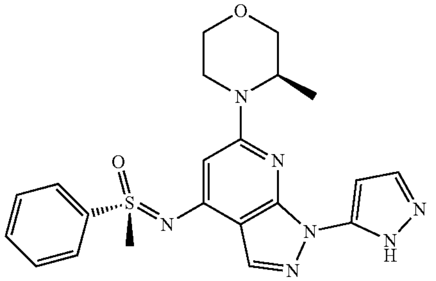
11-B or 11-A

Compound 11-2 (130 mg) was synthesized in a similar manner to that described in Example 1 using compound K1 in place of the dimethylsulfoximine of step 1 in Example 1. The above compound 11-2 was prepared and separated by chiral HPLC (mobile phase: (n-hexane:dichloromethane=7:3):isopropanol=3:1; flow rate: 40 mL/min; column temperature: 25° C.; column: CHIRALART Amylose-SB 30×250) to give compound 11-A (40 mg) and compound 11-B (45 mg) sequentially.

Compound 11-A: $R_t$=13.1 min.

MS (ESI, $[M+H]^+$) m/z: 438.20.

$^1H$ NMR (500 MHz, DMSO-$d_6$): δ 8.03 (d, J=7.6 Hz, 2H), 8.00 (s, 1H), 7.76 (d, J=1.9 Hz, 1H), 7.72 (t, J=7.3 Hz, 1H), 7.65 (t, J=7.6 Hz, 2H), 6.73 (s, 1H), 6.02 (s, 1H), 4.06 (d,

J=5.0 Hz, 1H), 3.90 (dd, J=11.2, 3.0 Hz, 1H), 3.80 (d, J=12.4 Hz, 1H), 3.69 (d, J=11.3 Hz, 1H), 3.59 (s, 3H), 3.54 (dd, J=11.3, 2.6 Hz, 1H), 3.42 (td, J=11.7, 2.6 Hz, 1H), 2.97 (td, J=12.8, 3.6 Hz, 1H), 1.10 (d, J=6.6 Hz, 3H).

Compound 11-B: $R_t$=20.8 min.

MS (ESI, $[M+H]^+$) m/z: 438.20.

$^1H$ NMR (500 MHz, DMSO-$d_6$): δ 8.12-7.89 (m, 3H), 7.76 (d, J=1.8 Hz, 1H), 7.71 (t, J=7.3 Hz, 1H), 7.65 (t, J=7.6 Hz, 2H), 6.72 (d, J=2.0 Hz, 1H), 5.90 (s, 1H), 3.97-3.85 (m, 2H), 3.82 (d, J=12.6 Hz, 1H), 3.66 (d, J=11.3 Hz, 1H), 3.61 (s, 3H), 3.57 (dd, J=11.4, 2.4 Hz, 1H), 3.38 (td, J=11.8, 2.4 Hz, 1H), 2.95 (td, J=12.9, 3.6 Hz, 1H), 0.79 (d, J=6.6 Hz, 3H).

Example 12: Synthesis of Compound 12-A and Compound 12-B

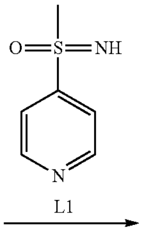

L1

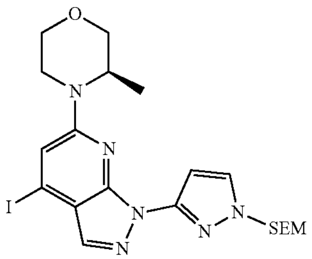

A1

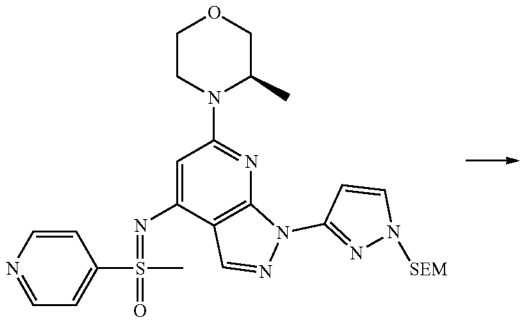

12-1

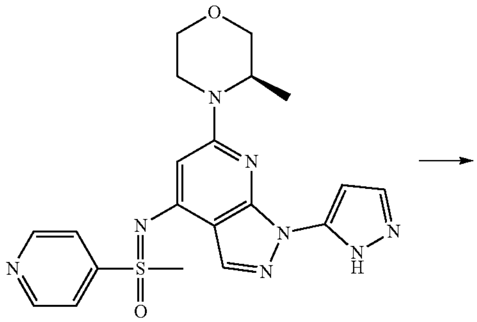

12-2

-continued

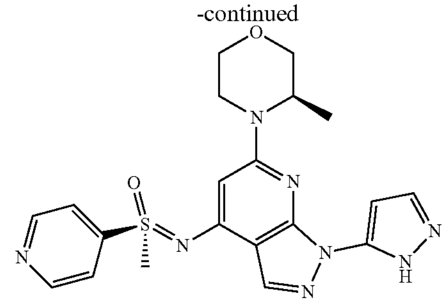

12-A or 12-B

+

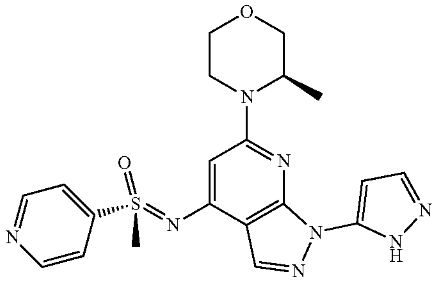

12-B or 12-A

Compound 12-2 (130 mg) was synthesized in a similar manner to that described in Example 1 using compound L1 in place of the dimethylsulfoximine of step 1 in Example 1. The above compound 12-2 was prepared and separated by chiral HPLC (mobile phase: n-hexane:ethanol=9:11; flow rate: 40 mL/min; column temperature: 25° C.; column: CHIRALART Cellulose-SB 30×250 mm) to give compound 12-A (52 mg) and compound 12-B (50 mg) sequentially.

Compound 12-A: $R_t$=14.1 min.

MS (ESI, $[M+H]^+$) m/z: 439.15.

$^1H$ NMR (500 MHz, DMSO-$d_6$) δ 12.74 (s, 1H), 8.91 (d, J=4.5 Hz, 2H), 8.00 (d, J=6.1 Hz, 3H), 7.79 (s, 1H), 6.73 (s, 1H), 6.02 (s, 1H), 4.09 (d, J=5.0 Hz, 1H), 3.91 (dd, J=11.3, 3.1 Hz, 1H), 3.81 (d, J=13.0 Hz, 1H), 3.70 (d, J=8.9 Hz, 4H), 3.55 (d, J=14.2 Hz, 1H), 3.43 (td, J=11.8, 2.9 Hz, 1H), 2.98 (td, J=12.7, 3.4 Hz, 1H), 1.10 (d, J=6.7 Hz, 3H).

Compound 12-B: $R_t$=18.8 min.

MS (ESI, $[M+H]^+$) m/z: 439.16.

$^1H$ NMR (500 MHz, DMSO-$d_6$): δ 12.69 (s, 1H), 8.90 (dd, J=4.5, 1.6 Hz, 2H), 8.09-7.86 (m, 3H), 7.78 (s, 1H), 6.72 (s, 1H), 5.89 (s, 1H), 3.98-3.82 (m, 3H), 3.70 (d, J=9.0 Hz, 3H), 3.67 (d, J=11.4 Hz, 1H), 3.58 (dd, J=11.4, 2.9 Hz, 1H), 3.40 (dd, J=17.8, 8.8 Hz, 1H), 2.96 (td, J=12.9, 3.7 Hz, 1H), 0.81 (d, J=6.7 Hz, 3H).

Example 13: Synthesis of Compound 13

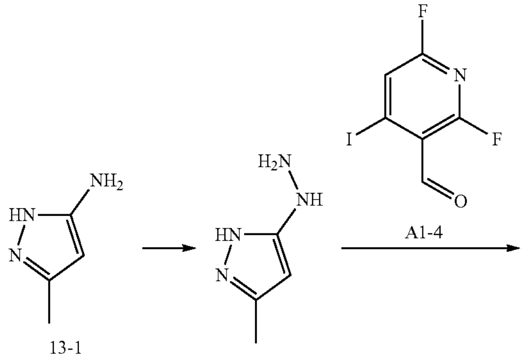

13-1

13-2

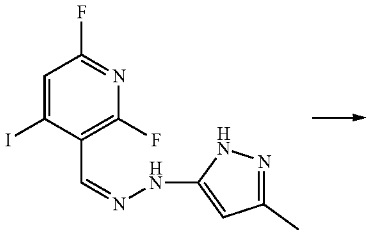

13-3

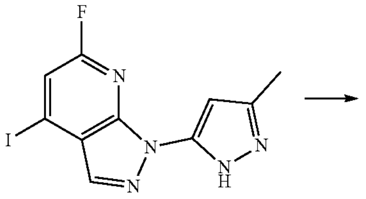

13-4

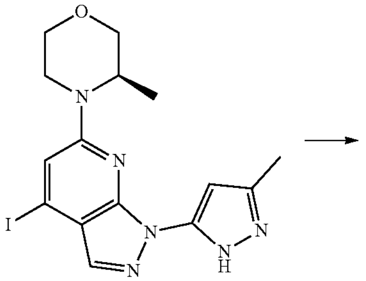

13-5

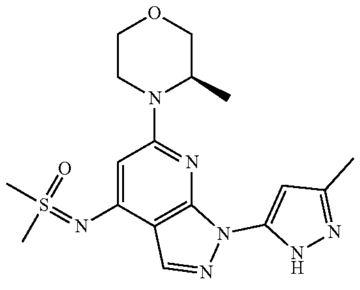

13

Step 1: Synthesis of Compound 13-2

Compound 13-1 (3 g) was dissolved in a 6 M solution of hydrochloric acid (20 mL). The solution was cooled to below 5° C., and a 1 M aqueous solution of sodium nitrite (31 mL) was added dropwise. The mixture was left to react at 5° C. for 1 h. A 1 M solution of stannous chloride in aqueous hydrochloric acid (62 mL) was added dropwise to the mixture, and the mixture was left to react overnight at room temperature. The reaction solution was concentrated, and the resulting crude product was slurried with ethyl acetate (30 mL), then filtered, and the filter cake was dried to give compound 13-2 (9.1 g, crude). The product was directly used in the next step.

$^1$H NMR (500 MHz, DMSO-$d_6$) δ 9.87 (s, 2H), 7.47-7.12 (m, 1H), 5.61 (s, 1H), 2.19 (s, 3H).

Step 2: Synthesis of Compound 13-3

Compound A1-4 (3.7 g), compound 13-2 (6.13 g) and ethanol (80 mL) were mixed and left to react at room temperature for 0.5 h. After concentration, the residue was dissolved in ethyl acetate (200 mL). The solution was washed with a saturated solution of sodium bicarbonate, water and saturated brine successively and dried over anhydrous sodium sulfate. After filtration and concentration, the resulting crude product was separated and purified by column chromatography (petroleum ether:ethyl acetate=1:1) to give compound 13-3 (2.1 g).

$^1$H NMR (500 MHz, DMSO-$d_6$) δ 11.66 (s, 1H), 10.73 (s, 1H), 7.91 (s, 1H), 7.80 (d, J=2.5 Hz, 1H), 5.76 (s, 1H), 2.17 (s, 3H).

Step 3: Synthesis of Compound 13-4

Compound 13-3 (1 g) and N-methylpyrrolidone (15 mL) were mixed, microwaved to 200° C. and left to react for 20 min. Water (100 mL) was added to the reaction solution, and a solid precipitated. The solid was collected by filtration, washed and dried to give compound 13-4 (202 mg).

$^1$H NMR (500 MHz, DMSO-$d_6$) δ 12.76 (s, 1H), 8.24 (s, 1H), 7.67 (s, 1H), 6.43 (s, 1H), 2.33 (s, 3H).

Step 4: Synthesis of Compound 13-5

Compound 13-4 (200 mg), (R)-3-methylmorpholine (118 mg) and dimethyl sulfoxide (7 mL) were mixed, heated to 120° C. and left to react for 6 h. Water was added to the reaction solution, and a solid precipitated. The solid was collected by filtration, washed and dried to give compound 13-5 (160 mg).

$^1$H NMR (500 MHz, DMSO-$d_6$) δ 12.53 (s, 1H), 7.80 (s, 1H), 7.26 (s, 1H), 6.49 (s, 1H), 4.49-4.39 (m, 1H), 4.04 (d, J=13.0 Hz, 1H), 3.95 (dd, J=11.3, 3.0 Hz, 1H), 3.74 (d, J=11.4 Hz, 1H), 3.63 (dd, J=11.4, 2.6 Hz, 1H), 3.48 (td, J=11.9, 2.7 Hz, 1H), 3.16 (td, J=13.0, 3.6 Hz, 1H), 2.30 (s, 3H), 1.19 (d, J=6.7 Hz, 3H).

Step 5: Synthesis of Compound 13

Compound 13-5 (140 mg), dimethylsulfoximine (40 mg), tris(dibenzylideneacetone)dipalladium (15 mg), 4,5-bisdiphenylphosphino-9,9-dimethylxanthene (19 mg), cesium carbonate (215 mg) and dioxane (10 mL) were mixed, heated to 100° C. and left to react for 8 h. The reaction solution was filtered and concentrated, and the resulting crude product was separated and purified by column chromatography (dichloromethane:methanol=10:1) to give compound 13 (37 mg).

MS (ESI, [M+H]$^+$) m/z: 390.14.

$^1H$ NMR (500 MHz, DMSO-$d_6$) δ 12.39 (s, 1H), 7.85 (s, 1H), 6.52 (s, 1H), 6.17 (s, 1H), 4.30 (d, J=5.1 Hz, 1H), 4.03-3.86 (m, 2H), 3.75 (d, J=11.2 Hz, 1H), 3.64 (dd, J=11.3, 2.5 Hz, 1H), 3.49 (td, J=11.8, 2.5 Hz, 1H), 3.40 (d, J=1.4 Hz, 6H), 3.18-3.05 (m, 1H), 2.29 (s, 3H), 1.17 (d, J=6.6 Hz, 3H).

Example 14: Synthesis of Compounds 14-A and 14-B

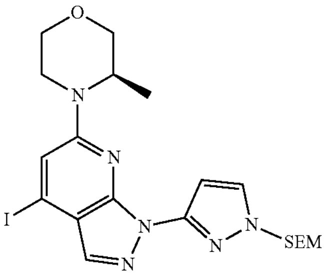

A1

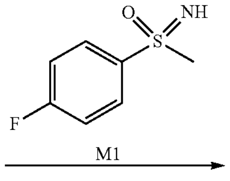

M1

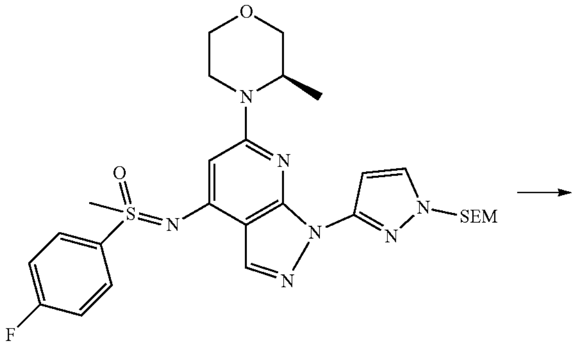

14-1

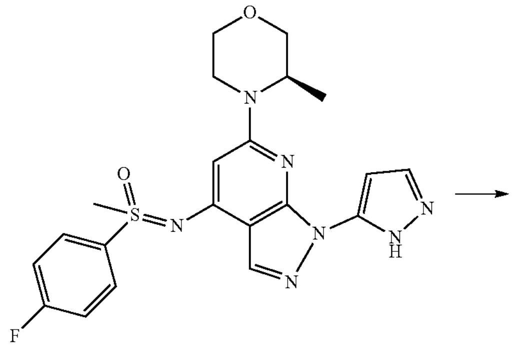

14-2

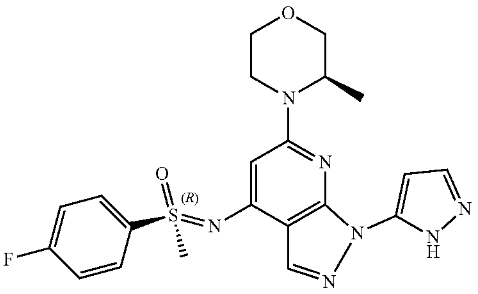

14-A or 14-B

-continued

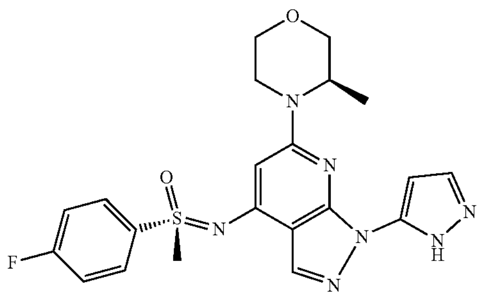

14-B or 14-A

Compound 14-2 (180 mg) was synthesized in a similar manner to that described in Example 1 using compound M1 in place of the dimethylsulfoximine of step 1 in Example 1. The above compound 14-2 was prepared and separated by chiral HPLC (mobile phase: n-hexane:ethanol=60:40; flow rate: 1 mL/min; column temperature: 25° C.; column: CHIRALART Cellulose-SB) to give compound 14-A (67 mg) and compound 14-B (70 mg) sequentially.

Compound 14-A: $R_t$=16.5 min.

$^1H$ NMR (500 MHz, $CDCl_3$) δ 8.12 (s, 1H), 8.07-7.89 (m, 2H), 7.61 (d, J=2.1 Hz, 1H), 7.23 (t, J=8.5 Hz, 2H), 6.77 (s, 1H), 6.13 (s, 1H), 4.24-4.16 (m, 1H), 4.00 (dd, J=11.4, 3.8 Hz, 1H), 3.87-3.84 (m, 1H), 3.79-3.77 (m, 1H), 3.72-3.69 (m, 1H), 3.58 (td, J=11.8, 3.1 Hz, 1H), 3.37 (s, 3H), 3.20 (td, J=12.6, 3.8 Hz, 1H), 1.26 (d, J=6.7 Hz, 3H).

HRMS: (ESI) calculated for $C_{21}H_{22}FN_7O_2S([M+H]^+)$ m/z: 456.1618, found: 456.1613.

Compound 14-B: $R_t$=24.5 min.

$^1H$ NMR (500 MHz, $CDCl_3$) δ 11.48 (brs, 1H), 8.12 (s, 1H), 8.03-7.90 (m, 2H), 7.60 (d, J=2.1 Hz, 1H), 7.22 (t, J=8.4 Hz, 2H), 6.76 (s, 1H), 6.04 (s, 1H), 4.13-4.04 (m, 1H), 3.99 (dd, J=11.4, 3.8 Hz, 1H), 3.88 (dd, J=13.1, 2.9 Hz, 1H), 3.79-3.69 (m, 2H), 3.56 (td, J=11.9, 3.1 Hz, 1H), 3.39 (s, 3H), 3.19 (td, J=12.7, 3.9 Hz, 1H), 1.01 (d, J=6.7 Hz, 3H).

HRMS: (ESI) calculated for $C_{21}H_{22}FN_7O_2S([M+H]^+)$ m/z: 456.1618, found: 456.1612.

Example 15: Synthesis of Compounds 15-A and 15-B

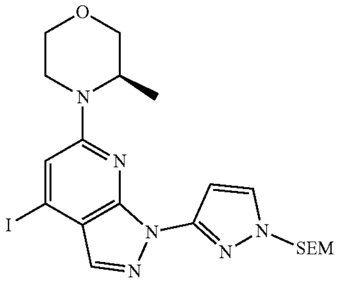

A1

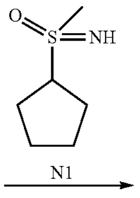

N1

-continued

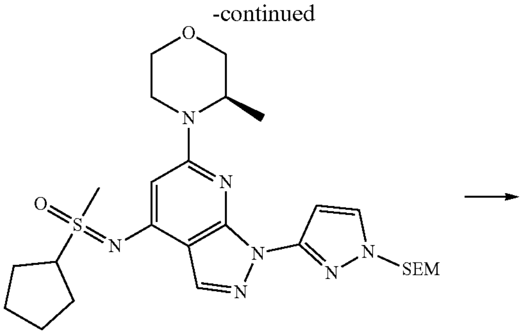

15-1

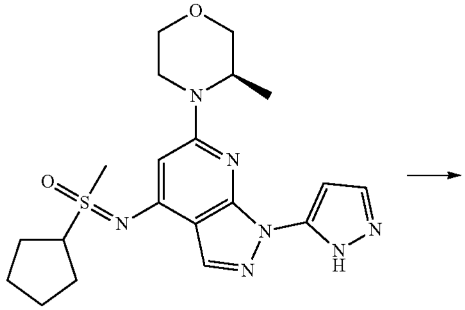

15-2

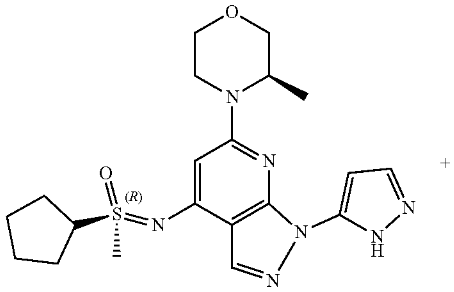

15-A or 15-B

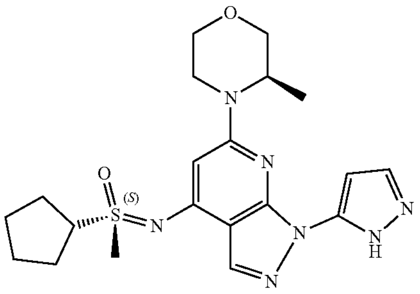

15-B or 15-A

Compound 15-2 (90 mg) was synthesized in a similar manner to that described in Example 1 using compound N1 in place of the dimethylsulfoximine of step 1 in Example 1. The above compound 15-2 was prepared and separated by chiral HPLC (mobile phase: n-hexane:ethanol=3:2; flow rate: 40 mL/min; column temperature: 25° C.; column: CHIRALART Cellulose-SB) to give compound 15-A (35 mg) and compound 15-B (32 mg) sequentially.

Compound 15-A: $R_t$=10.6 min.

MS (ESI, $[M+H]^+$) m/z: 430.19.

$^1$H-NMR (500 MHz, DMSO-$d_6$) δ 12.68 (s, 1H), 7.89 (s, 1H), 7.74 (s, 1H), 6.78 (s, 1H), 6.20 (s, 1H), 4.29 (d, J=5.0 Hz, 1H), 4.03-3.89 (m, 3H), 3.74 (d, J=11.2 Hz, 1H), 3.64 (dd, J=11.3, 2.8 Hz, 1H), 3.48 (td, J=11.8, 2.9 Hz, 1H), 3.27 (s, 3H), 3.18-3.05 (m, 1H), 2.16-2.00 (m, 4H), 1.81-1.69 (m, 2H), 1.68-1.56 (m, 2H), 1.17 (d, J=6.7 Hz, 3H).

Compound 15-B: $R_t$=17.5 min.

MS (ESI, $[M+H]^+$) m/z: 430.19.

$^1$H-NMR (500 MHz, DMSO-$d_6$): δ 12.68 (s, 1H), 7.89 (s, 1H), 7.80 (s, 1H), 6.79 (s, 1H), 6.18 (s, 1H), 4.32 (s, 1H), 3.96 (dd, J=15.5, 7.3 Hz, 2H), 3.90 (d, J=12.4 Hz, 1H), 3.75 (d, J=11.2 Hz, 1H), 3.64 (dd, J=11.2, 2.3 Hz, 1H), 3.49 (td, J=11.7, 2.3 Hz, 1H), 3.27 (s, 3H), 3.11 (td, J=12.6, 3.0 Hz, 1H), 2.17-1.98 (m, 4H), 1.82-1.71 (m, 2H), 1.70-1.60 (m, 2H), 1.17 (d, J=6.6 Hz, 3H).

Example 16: Synthesis of Compounds 16-A and 16-B

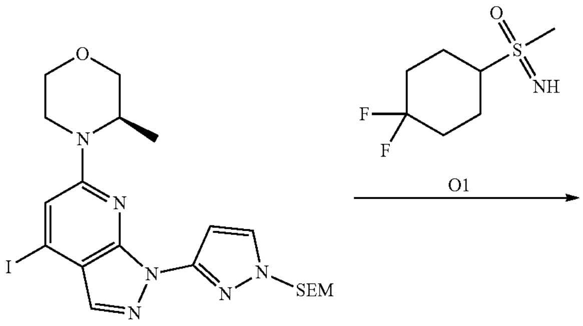

A1

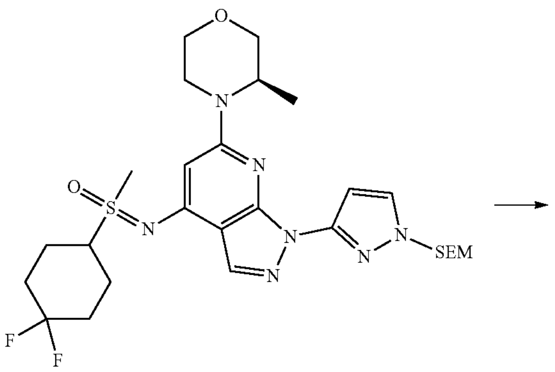

16-1

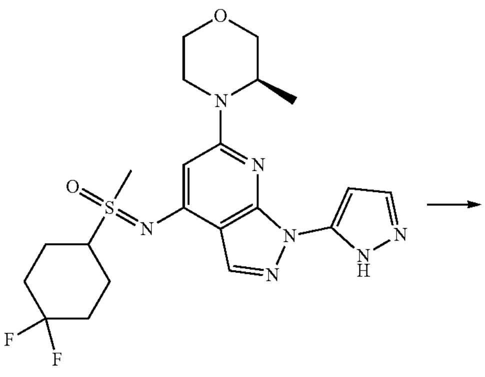

16-2

-continued

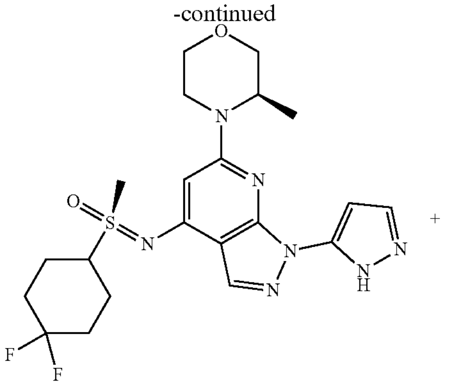

16-A or 16-B

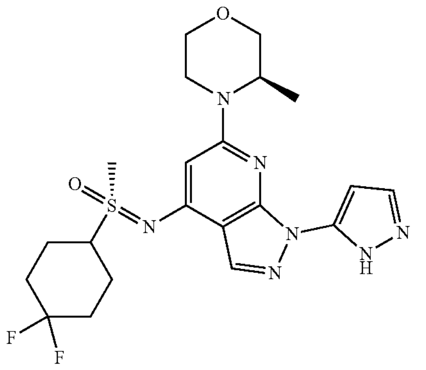

16-B or 16-A

Compound 16-2 (85 mg) was synthesized in a similar manner to that described in Example 1 using compound 01 in place of the dimethylsulfoximine of step 1 in Example 1. The above compound 16-2 was prepared and separated by chiral HPLC (mobile phase: n-hexane:ethanol=3:2; flow rate: 40 mL/min; column temperature: 25° C.; column: CHIRALART Cellulose-SB) to give compound 16-A (30 mg) and compound 16-B (28 mg) sequentially.

Compound 16-A: $R_t$=13.04 min.

MS (ESI, $[M+H]^+$) m/z: 480.24.

$^1$H NMR (500 MHz, DMSO-$d_6$) δ 12.73 (s, 1H), 7.91 (s, 1H), 7.77 (s, 1H), 6.75 (s, 1H), 6.22 (s, 1H), 4.31 (d, J=5.0 Hz, 1H), 4.04-3.85 (m, 2H), 3.68 (m, 3H), 3.49 (dd, J=23.4, 2.7 Hz, 1H), 3.31 (s, 3H), 3.11 (m, 1H), 2.34 (t, J=13.1 Hz, 2H), 2.21 (s, 2H), 2.13-1.68 (m, 4H), 1.17 (d, J=6.6 Hz, 3H).

Compound 16-B: $R_t$=18.03 min.

MS (ESI, $[M+H]^+$) m/z: 480.24.

$^1$H-NMR (500 MHz, DMSO-$d_6$): δ 12.73 (s, 1H), 7.90 (s, 1H), 7.81 (s, 1H), 6.79 (s, 1H), 6.24 (s, 1H), 4.30 (d, J=4.7 Hz, 1H), 4.03-3.86 (m, 2H), 3.78-3.60 (m, 3H), 3.49 (m, 1H), 3.32-3.30 (m, 3H), 3.19-3.06 (m, 1H), 2.34 (t, J=14.9 Hz, 2H), 2.21 (dd, J=10.8, 4.7 Hz, 2H), 2.08-1.77 (m, 4H), 1.17 (d, J=6.6 Hz, 3H).

Example 17: Synthesis of Compound 17

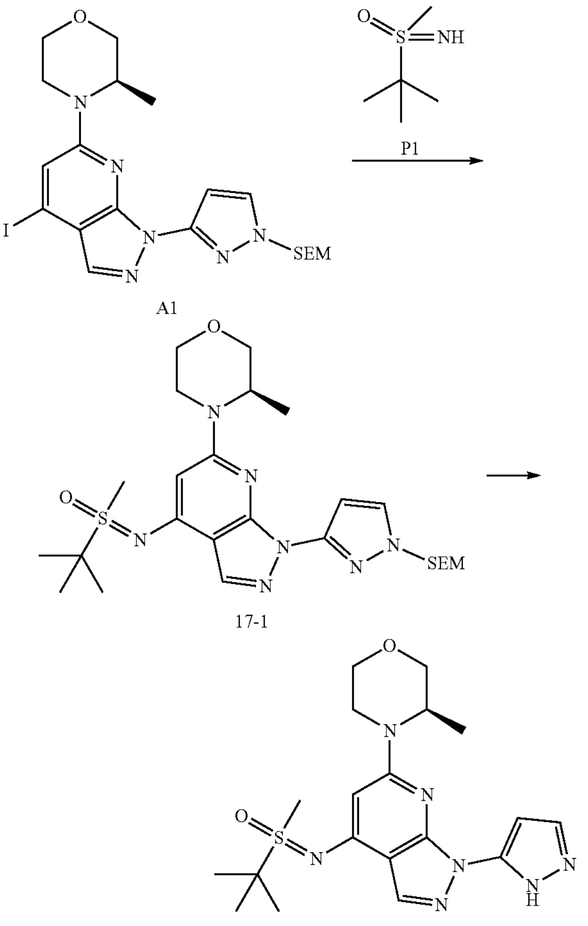

A1

17-1

17

Step 1: Synthesis of Compound 17-1

Compound A1 (170 mg), compound P1 (75 mg), tris (dibenzylideneacetone)dipalladium (25.4 mg), 4,5-bisdiphenylphosphino-9,9-dimethylxanthene (32.1 mg), cesium carbonate (362 mg) and 1,4-dioxane (6 mL) were mixed and left to react at 80° C. for 1 h under nitrogen atmosphere. The reaction solution was filtered, and the filtrate was concentrated. The crude product was then separated and purified by column chromatography (dichloromethane:methanol=10:1) to give compound 17-1 (200 mg).

MS (ESI, $[M+H]^+$) m/z: 548.31.

Step 2: Synthesis of Compound 17

Compound 17-1 (200 mg) was dissolved in tetrahydrofuran (2 mL), and tetrabutylammonium fluoride (1 g, 1.912 mL) was added to the reaction solution. The mixture was left to react at 80° C. for 16 h under nitrogen atmosphere. The reaction solution was concentrated, and the crude product was separated and purified by column chromatography (dichloromethane:methanol=13:1) to give compound 17 (50 mg).

MS (ESI, $[M+H]^+$) m/z: 418.33.

$^1$H NMR (500 MHz, DMSO-$d_6$) δ 12.72 (s, 1H), 7.94 (s, 1H), 7.80 (s, 1H), 6.79 (s, 1H), 6.26 (d, J=10.6 Hz, 1H), 4.30 (d, J=26.9 Hz, 1H), 3.93 (dd, J=29.2, 11.9 Hz, 2H), 3.75 (d, J=11.1 Hz, 1H), 3.65 (d, J=10.9 Hz, 1H), 3.49 (t, J=11.7 Hz, 1H), 3.21 (d, J=4.4 Hz, 3H), 3.12 (t, J=12.4 Hz, 1H), 1.50 (s, 9H), 1.23-1.05 (m, 3H).

Example 18: Synthesis of Compound 18

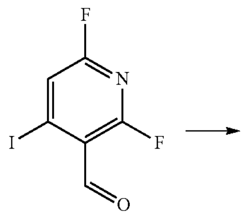

A1-4

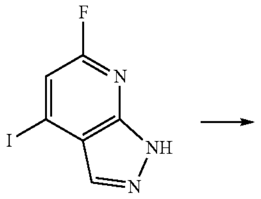

18-1

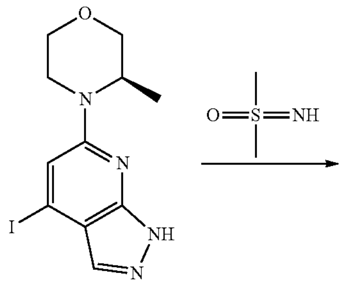

18-2

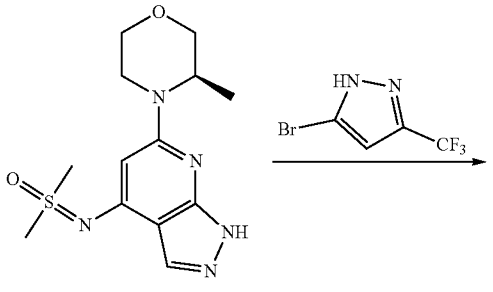

18-3

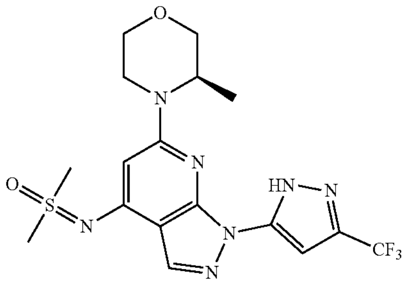

18

Step 1: Synthesis of Compound 18-1

Compound A1-4 (3 g) was dissolved in tetrahydrofuran (30 mL), and a solution of hydrazine in tetrahydrofuran (1 M, 11.15 mL) was added. The reaction was stirred at 60° C. for 1 h. The reaction solution was concentrated, and the resulting crude product was separated and purified by column chromatography (petroleum ether:ethyl acetate=4:1) to give compound 18-1 (0.95 g).

MS: (ESI, $[M-H]^-$) m/z: 261.83

$^1$H NMR (500 MHz, DMSO-$d_6$) δ 14.05 (s, 1H), 8.03-7.99 (m, 1H), 7.53 (s, 1H).

Step 2: Synthesis of Compound 18-2

Compound 18-1 (900 mg) was dissolved in dimethyl sulfoxide (10 mL), and (R)-3-methylmorpholine (1384 mg, 13.69 mmol) was added. The mixture was heated to 120° C. and left to react for 16 h. The residue was dissolved in ethyl acetate (20 mL), and the solution was washed with water and saturated brine successively, dried over anhydrous sodium sulfate, filtered, and concentrated. The resulting crude product was separated and purified by column chromatography (petroleum ether:ethyl acetate=1:1) to give compound 18-2 (0.72 g).

MS: (ESI, $[M+H]^+$) m/z: 344.90

$^1$H NMR (500 MHz, DMSO-$d_6$) δ 13.14 (s, 1H), 7.60 (s, 1H), 7.16 (s, 1H), 4.44-4.35 (m, 1H), 3.96-3.91 (m, 2H), 3.71 (d, J=11.5 Hz, 1H), 3.62 (dd, J=11.4, 3.1 Hz, 1H), 3.49-3.43 (m, 1H), 3.13 (td, J=12.8, 3.8 Hz, 1H), 1.16 (d, J=6.7 Hz, 3H).

Step 3: Synthesis of Compound 18-3

Compound 18-2 (700 mg) was dissolved in dioxane (10 mL), and dimethylsulfoximine (227 mg), tris(dibenzylideneacetone)dipalladium (186 mg), 4,5-bisdiphenylphosphino-9,9-dimethylxanthene (235 mg) and cesium carbonate (1988 mg) were added. Under nitrogen atmosphere, the reaction solution was microwaved (400 W) to 110° C. and left to react for 1 h. After filtration under vacuum, the filtrate was concentrated. The crude product was then separated and purified by column chromatography (dichloromethane: methanol=20:1) to give compound 18-3 (0.34 g).

MS: (ESI, $[M+H]^+$) m/z: 310.02

Step 4: Synthesis of Compound 18

Compound 18-3 (330 mg), N-methylpyrrolidone (9 mL), 3-bromo-5-(trifluoromethyl)-1H-pyrazole (459 mg), cesium carbonate (1043 mg), (1R,2R)—N1,N2-dimethylcyclohexane-1,2-diamine (303 mg) and copper(I) iodide (305 mg) were mixed, and the reaction was heated in a 120° C. oil bath for 16 h. After filtration under vacuum, the filtrate was concentrated. The crude product was then separated and purified by column chromatography (dichloromethane: methanol=10:1) to give the target compound (0.24 g, crude). The crude target compound was purified by HPLC (mobile phase: 0.1% aqueous acetic acid:acetonitrile=65:35; flow rate: 40 mL/min; column temperature: 25° C.; column: YMC-Triart Prep C18-S) to give compound 18 (0.022 g).

$^1$H NMR (500 MHz, $CDCl_3$) δ 8.05 (s, 1H), 6.81 (s, 1H), 6.31 (s, 1H), 4.32 (d, J=8.2 Hz, 1H), 4.07 (dd, J=11.4, 3.8 Hz, 1H), 3.93-3.74 (m, 3H), 3.64 (td, J=11.9, 3.2 Hz, 1H), 3.41-3.24 (m, 7H), 1.33 (d, J=6.7 Hz, 3H).

HRMS: (ESI, $[M+H]^+$) m/z: 444.1426.

Example 19: Synthesis of Compounds 19-A and 19-B

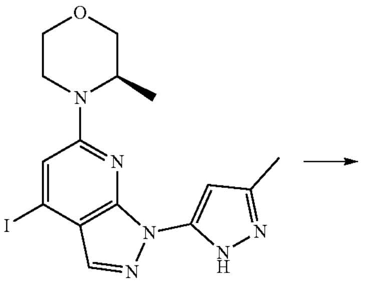

13-5

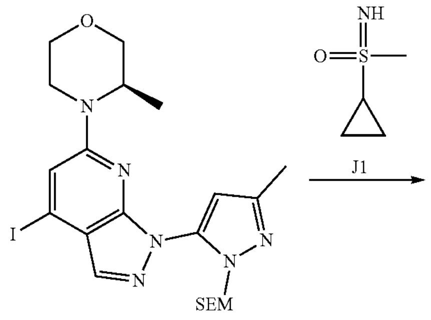

19-1

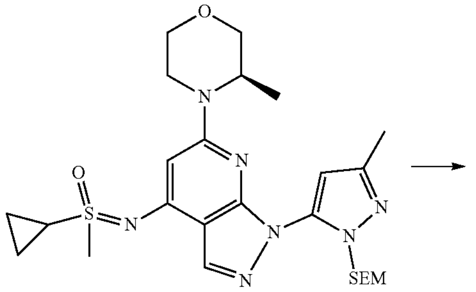

19-2

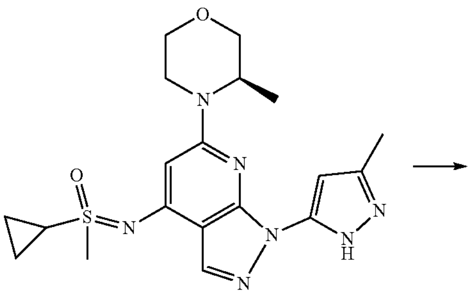

19

-continued

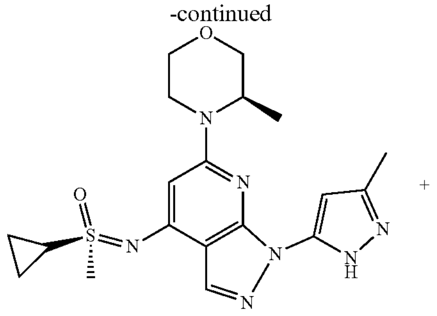

19-A or 19-B

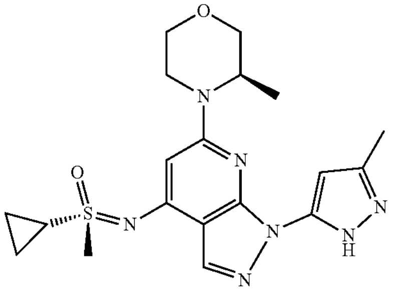

19-B or 19-A

Step 1: Synthesis of Compound 19-1

Compound 13-5 (550 mg), diisopropylethylamine (260 mg) and dichloromethane (20 mL) were mixed, and 2-(trimethylsilyl)ethoxymethyl chloride (268 mg) was added dropwise. The mixture was left to react at room temperature for 1 h. Dichloromethane (20 mL) and saturated sodium bicarbonate (20 mL) were added to the reaction solution. The organic phase was separated and concentrated, and the resulting crude product was purified by column chromatography (petroleum ether:ethyl acetate=1:1) to give compound 19-1 (503 mg).

MS (ESI, $[M+H]^+$) m/z: 555.07.

$^1H$ NMR (500 MHz, DMSO-$d_6$) δ 7.96 (s, 1H), 7.31 (s, 1H), 6.41 (s, 1H), 5.45 (q, J=11.3 Hz, 2H), 4.38 (dd, J=6.5, 2.1 Hz, 1H), 3.99 (d, J=11.7 Hz, 1H), 3.92 (dd, J=11.4, 3.5 Hz, 1H), 3.71 (d, J=11.4 Hz, 1H), 3.57 (dd, J=11.5, 2.9 Hz, 1H), 3.42 (td, J=11.9, 3.0 Hz, 1H), 3.21-3.07 (m, 3H), 2.24 (s, 3H), 1.16 (d, J=6.7 Hz, 3H), 0.57 (t, J=8.2 Hz, 2H), −0.24 (s, 9H).

Step 2: Synthesis of Compound 19-2

Compound 19-1 (400 mg), compound J1 (129 mg), tris(dibenzylideneacetone)dipalladium (66.1 mg), 4,5-bisdiphenylphosphino-9,9-dimethylxanthene (83 mg), cesium carbonate (588 mg) and 1,4-dioxane (20 mL) were mixed and left to react at 80° C. for 1 h under nitrogen atmosphere. The reaction solution was filtered, and the filtrate was concentrated. The crude product was then separated and purified by column chromatography (petroleum ether:ethyl acetate=1:1) to give compound 19-2 (310 mg).

MS (ESI, $[M+H]^+$) m/z: 546.21.

$^1H$ NMR (500 MHz, DMSO-$d_6$) δ 8.01 (d, J=3.7 Hz, 1H), 6.36 (s, 1H), 6.20 (s, 1H), 5.54-5.44 (m, 2H), 4.25-4.15 (m, 1H), 3.96-3.80 (m, 2H), 3.72 (d, J=11.4 Hz, 1H), 3.63-3.56 (m, 1H), 3.48-3.40 (m, 1H), 3.38 (d, J=5.5 Hz, 3H), 3.27-

3.17 (m, 2H), 3.10-2.94 (m, 2H), 2.23 (s, 3H), 1.37-1.26 (m, 1H), 1.24-1.18 (m, 1H), 1.17-1.08 (m, 5H), 0.65-0.57 (m, 2H), −0.20 (s, 9H).

Step 3: Synthesis of Compound 19-A and Compound 19-B

Compound 19-2 (300 mg) was dissolved in dichloromethane (4 mL). The solution was cooled to 0° C., and triethylsilane (1.41 g) and trifluoroacetic acid (12 mL) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=9:1) to give compound 19 (201 mg). The above compound 19 was prepared and separated by chiral HPLC (mobile phase: n-hexane: ethanol=70:30; flow rate: 40 mL/min; column temperature: 25° C.; column: CHIRALART Cellulose-SB 30×250) to give compound 19-A (52 mg) and compound 19-B (57 mg) sequentially.

Compound 19-A: $R_t$=13.5 min.

HRMS: (ESI, $[M+H]^+$) m/z: 416.1865.

$^1H$ NMR (500 MHz, DMSO-$d_6$) δ 12.40 (s, 1H), 7.88 (s, 1H), 6.51 (s, 1H), 6.18 (s, 1H), 4.38-4.19 (m, 1H), 3.96 (d, J=9.5 Hz, 1H), 3.90 (d, J=12.7 Hz, 1H), 3.75 (d, J=11.2 Hz, 1H), 3.64 (d, J=10.9 Hz, 1H), 3.49 (t, J=10.6 Hz, 1H), 3.37 (s, 3H), 3.11 (t, J=11.2 Hz, 1H), 3.04-2.95 (m, 1H), 2.29 (s, 3H), 1.32-1.27 (m, 1H), 1.22-1.11 (m, 6H).

Compound 19-B: $R_t$=18.0 min.

HRMS: (ESI, $[M+H]^+$) m/z: 416.1865.

$^1H$ NMR (500 MHz, DMSO-$d_6$) δ 12.39 (s, 1H), 7.87 (s, 1H), 6.51 (s, 1H), 6.18 (s, 1H), 4.23 (d, J=4.9 Hz, 1H), 3.95 (dd, J=16.5, 8.3 Hz, 2H), 3.74 (d, J=11.3 Hz, 1H), 3.64 (dd, J=11.3, 2.8 Hz, 1H), 3.48 (td, J=11.8, 3.0 Hz, 1H), 3.38 (s, 3H), 3.10 (td, J=12.8, 3.5 Hz, 1H), 3.00-2.93 (m, 1H), 2.29 (s, 3H), 1.36-1.28 (m, 1H), 1.23-1.07 (m, 6H).

Example 20: Synthesis of Compound 20

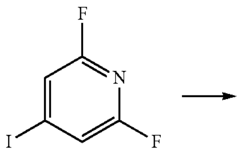

A1-3

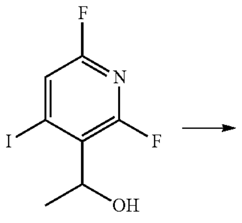

20-1

-continued

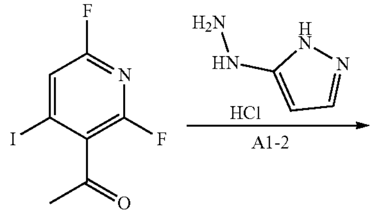

20-2

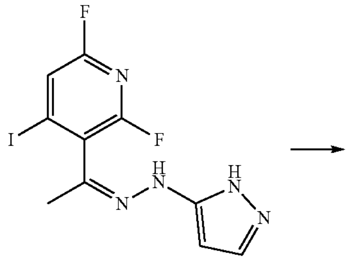

20-3

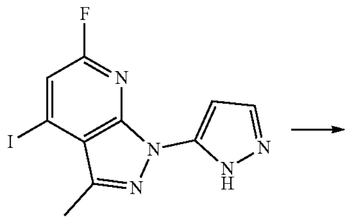

20-4

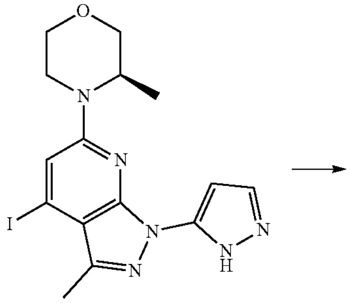

20-5

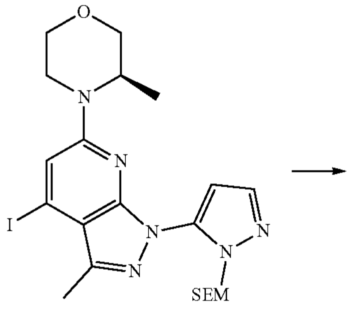

20-6

-continued

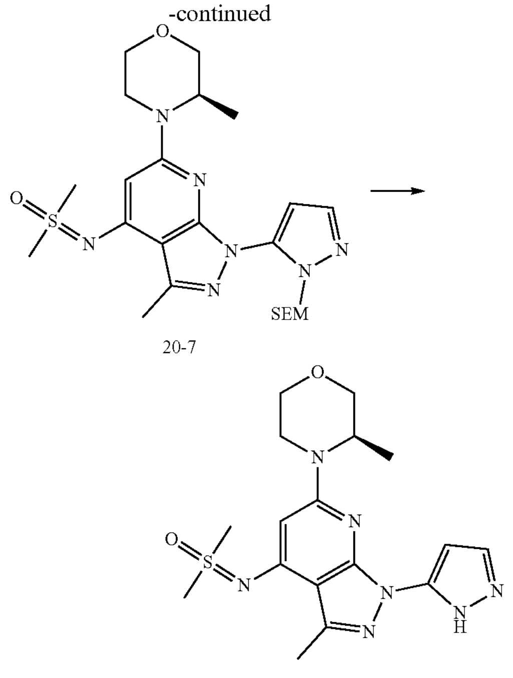

20-7

20

Step 1: Synthesis of Compound 20-1

Compound A1-3 (6 g) was dissolved in tetrahydrofuran (60 mL). The solution was cooled to −78° C., and a 2 M solution of lithium diisopropylamide in tetrahydrofuran/n-hexane (3 g, 14.00 mL) was added dropwise. The mixture was left to react at −78° C. for 1 h. Acetaldehyde (1.32 g) was added to the reaction solution, and the mixture was left to react at −78° C. for another 30 min. Formic acid (2.29 g) and ethyl acetate (100 mL) were then added, and the reaction solution was warmed to room temperature. The organic phase was washed with water and saturated brine successively and dried over anhydrous sodium sulfate. After filtration and concentration, the crude product was separated and purified by column chromatography (petroleum ether: ethyl acetate=5:1) to give compound 20-1 (5 g).

Step 2: Synthesis of Compound 20-2

Compound 20-1 (5 g), manganese dioxide (15.25 g) and toluene (80 mL) were mixed and left to react at 60° C. for 5 h. The reaction solution was filtered and washed, and the mother liquor was collected and concentrated to give compound 20-2 (4 g).

MS: (ESI, $[M+H]^+$) m/z: 284.12.

Step 3: Synthesis of Compound 20-3

Compound A1-2 (500 mg), compound 20-2 (500 mg) and ethanol (30 mL) were mixed and left to react at room temperature for 1 h. The reaction solution was concentrated, and the residue was dissolved in ethyl acetate. The solution was washed with saturated sodium bicarbonate, water and saturated brine successively, dried over anhydrous sodium sulfate, filtered, and concentrated to give compound 20-3 (400 mg).

MS: (ESI, $[M+H]^+$) m/z: 363.91.

$^1H$ NMR (500 MHz, DMSO-$d_6$) δ 11.94 (s, 1H), 9.50 (s, 1H), 7.81 (s, 1H), 7.47 (s, 1H), 5.85 (s, 1H), 2.11 (s, 3H).

Step 4: Synthesis of Compound 20-4

Compound 20-3 (400 mg) and N-methylpyrrolidone (8 mL) were mixed, microwaved to 200° C. and left to react for 20 min. Water was added to the reaction solution, and a solid precipitated. The solid was collected by filtration, washed and dried to give compound 20-4 (320 mg).

MS (ESI, $[M+H]^+$) m/z: 343.85.

$^1H$ NMR (500 MHz, DMSO-$d_6$) δ 13.03 (s, 1H), 7.90 (s, 1H), 7.65 (s, 1H), 6.62 (s, 1H), 2.69 (s, 3H).

Step 5: Synthesis of Compound 20-5

Compound 20-4 (320 mg), (R)-3-methylmorpholine (250 mg) and dimethyl sulfoxide (5 mL) were mixed, heated to 120° C. and left to react for 1 h. Water was added to the reaction solution, and a solid precipitated. The solid was collected by filtration, washed and dried to give compound 20-5 (260 mg).

MS (ESI, $[M+H]^+$) m/z: 425.13.

Step 6: Synthesis of Compound 20-6

Compound 20-5 (260 mg), diisopropylethylamine (250 mg) and dichloromethane (5 mL) were mixed, and 2-(trimethylsilyl)ethoxymethyl chloride (211 mg) was added dropwise. The mixture was left to react at room temperature for 30 min. Dichloromethane (20 mL) and saturated sodium bicarbonate (20 mL) were added to the reaction solution. The organic phase was separated and concentrated, and the resulting crude product was separated and purified by column chromatography (petroleum ether:ethyl acetate=3:1) to give compound 20-6 (180 mg).

MS (ESI, $[M+H]^+$) m/z: 555.30.

Step 7: Synthesis of Compound 20-7

Compound 20-6 (180 mg), dimethylsulfoximine (59.52 mg), tris(dibenzylideneacetone)dipalladium (13.04 mg), 4,5-bisdiphenylphosphino-9,9-dimethylxanthene (16.48 mg), cesium carbonate (186 mg) and 1,4-dioxane (3 mL) were mixed and left to react at 80° C. for 1 h under nitrogen atmosphere. The reaction solution was filtered, and the filtrate was concentrated. The crude product was then separated and purified by column chromatography (dichloromethane:methanol=14:1) to give compound 20-7 (140 mg).

MS (ESI, $[M+H]^+$) m/z: 520.27.

Step 8: Synthesis of Compound 20

Compound 20-7 (140 mg) was dissolved in dichloromethane (2 mL). The solution was cooled to 0° C., and triethylsilane (379 mg) and trifluoroacetic acid (15.9 g) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=9:1) to give compound 20 (80 mg).

MS (ESI, $[M+H]^+$) m/z: 390.27.

$^1$H NMR (500 MHz, DMSO-$d_6$) δ 12.63 (s, 1H), 7.76 (s, 1H), 6.75 (s, 1H), 6.11 (s, 1H), 4.30 (s, 1H), 3.95 (dd, J=11.1, 2.8 Hz, 1H), 3.88 (d, J=12.4 Hz, 1H), 3.74 (d, J=11.3 Hz, 1H), 3.64 (dd, J=11.3, 2.5 Hz, 1H), 3.49 (td, J=11.8, 2.7 Hz, 1H), 3.40 (s, 6H), 3.32 (s, 3H), 3.11 (td, J=12.4, 3.0 Hz, 1H), 1.16 (d, J=6.6 Hz, 3H).
Example 21: Synthesis of Compound 21
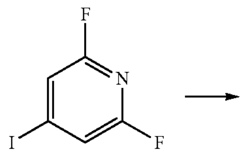
A1-3
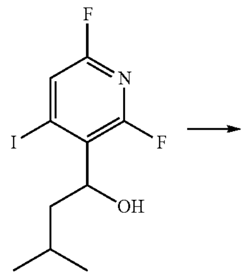
21-1
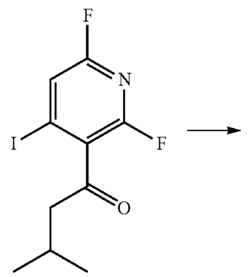
21-2
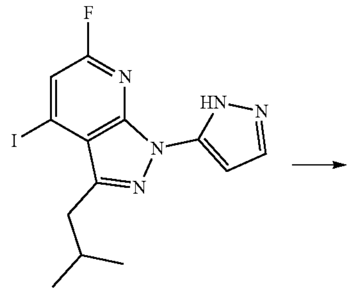
21-3
-continued
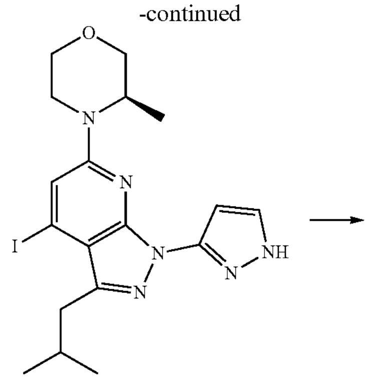
21-4
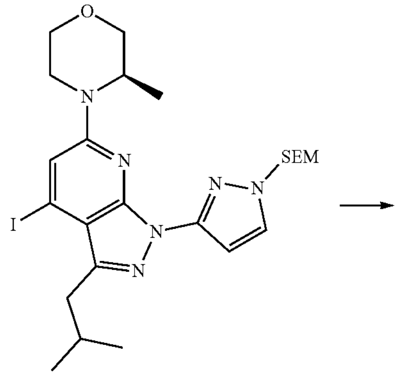
21-5
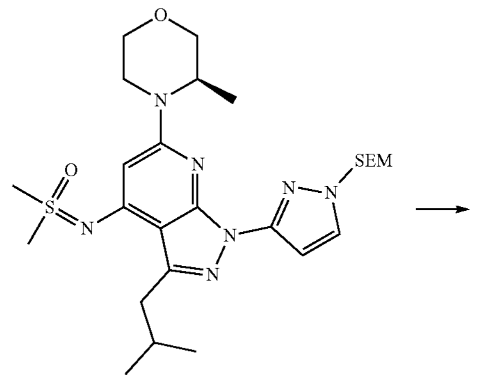
21-6
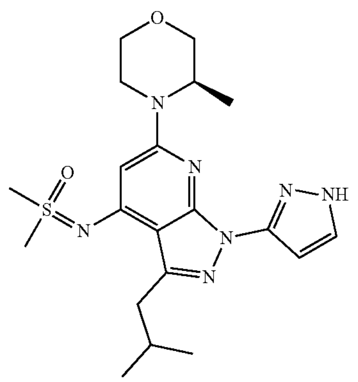
21

Step 1: Synthesis of Compound 21-1

Compound A1-3 (2 g) and tetrahydrofuran (20 mL) were mixed and cooled to −78° C., and a solution of lithium diisopropylamide in tetrahydrofuran (2 M, 6.21 mL) was added dropwise under nitrogen atmosphere. The mixture was left to react at −78° C. for 1 h. 3-Methylbutanal (1.430 g) was added to the reaction solution, and the reaction solution was stirred at −78° C. for another 1 h and then warmed to room temperature. A saturated aqueous solution of ammonium chloride was added. The organic phase was washed with water and saturated brine successively and dried over anhydrous sodium sulfate. After filtration and concentration, the crude product was separated and purified by column chromatography (petroleum ether:ethyl acetate=19:1) to give compound 21-1 (2.0 g).

$^{1}$H NMR (500 MHz, $CDCl_3$) δ 7.32 (d, J=3.1 Hz, 1H), 5.08-5.04 (m, 1H), 2.19-2.16 (m, 1H), 1.96-1.76 (m, 2H), 1.56-1.50 (m, 1H), 1.03-1.00 (m, 6H).

Step 2: Synthesis of Compound 21-2

Compound 21-1 (2 g), manganese dioxide (5.32 g) and toluene (20 mL) were mixed, heated to 90° C. and left to react for 16 h. TLC monitoring showed there remained some of the starting material. After filtration under vacuum, the filtrate was concentrated, and additional manganese dioxide (10.63 g) was then added. The mixture was heated to 90° C. and left to react for 2 h. The reaction mixture was filtered through diatomite under vacuum, and the filtrate was concentrated to give compound 21-2 (1.6 g).

$^{1}$H NMR (500 MHz, $CDCl_3$) δ 7.39 (d, J=2.8 Hz, 1H), 2.75 (dd, J=6.7, 1.7 Hz, 2H), 2.34-2.26 (m, 1H), 1.03 (d, J=6.6 Hz, 6H).

Step 3: Synthesis of Compound 21-3

Compound 21-2 (1.5 g), 5-hydrazino-1H-pyrazole hydrochloride (3.10 g) and ethanol (20 mL) were mixed, heated to 80° C. and stirred overnight. After the solvent was evaporated by concentration, N-methylpyrrolidone (20 mL) and 5-hydrazino-1H-pyrazole hydrochloride (3.10 g) were sequentially added. The mixture was heated to 130° C. and stirred for 2 h. The reaction mixture was cooled to room temperature. Water (50 mL) was added, and a solid precipitated. The solid was collected by filtration and dried to give compound 21-3 (1.5 g).

MS: (ESI, $[M+H]^+$) m/z: 385.99.

$^{1}$H NMR (500 MHz, $CDCl_3$) δ 7.72 (d, J=2.4 Hz, 1H), 7.37 (d, J=1.5 Hz, 1H), 6.89 (d, J=2.4 Hz, 1H), 3.04 (d, J=7.2 Hz, 2H), 2.33-2.25 (m, 1H), 1.06 (d, J=6.7 Hz, 6H).

Step 4: Synthesis of Compound 21-4

Compound 21-3 (1 g), (R)-3-methylmorpholine (1.313 g) and dimethyl sulfoxide (10 mL) were mixed, heated to 120° C. and left to react for 1 h. The reaction mixture was cooled to room temperature and then added dropwise to water (50 mL). After filtration under vacuum and drying, compound 21-4 (1.5 g) was obtained.

MS: (ESI, $[M+H]^+$) m/z: 467.07.

$^{1}$H NMR (500 MHz, $CDCl_3$d) δ 7.62 (d, J=2.2 Hz, 1H), 7.05 (s, 1H), 6.87-6.82 (m, 1H), 4.36-4.34 (m, 1H), 4.06 (dd, J=11.5, 3.8 Hz, 1H), 3.96 (dd, J=13.0, 3.0 Hz, 1H), 3.84 (d, J=11.3 Hz, 1H), 3.77 (dd, J=11.5, 3.2 Hz, 1H), 3.62 (td, J=11.8, 3.1 Hz, 1H), 3.34 (td, J=12.7, 3.9 Hz, 1H), 2.92 (d, J=7.2 Hz, 2H), 2.29-2.23 (m, 1H), 1.34 (d, J=6.8 Hz, 3H), 1.03 (dd, J=6.6, 1.3 Hz, 6H).

Step 5: Synthesis of Compound 21-5

Compound 21-4 (1.2 g), diisopropylethylamine (0.672 mL) and dichloromethane (20 mL) were mixed, and 2-(trimethylsilyl)ethoxymethyl chloride (0.515 g) was added. The mixture was stirred overnight at room temperature. The residue was dissolved in ethyl acetate (50 mL). The organic phase was washed with a saturated aqueous solution of sodium bicarbonate and water successively, separated, and concentrated. The resulting crude product was separated and purified by column chromatography (petroleum ether:ethyl acetate=4:1) to give compound 21-5 (0.57 g).

MS: (ESI, $[M+H]^+$) m/z: 597.16.

$^{1}$H NMR (500 MHz, $CDCl_3$) δ 7.63 (d, J=1.9 Hz, 1H), 7.02 (s, 1H), 6.54 (d, J=1.9 Hz, 1H), 5.80-5.63 (m, 2H), 4.39-4.20 (m, 1H), 4.00 (dd, J=11.5, 3.8 Hz, 1H), 3.92 (dd, J=13.2, 2.9 Hz, 1H), 3.78 (d, J=11.4 Hz, 1H), 3.70 (dd, J=11.4, 3.2 Hz, 1H), 3.55 (td, J=11.8, 3.1 Hz, 1H), 3.45-3.33 (m, 2H), 3.23 (td, J=12.7, 3.9 Hz, 1H), 2.89 (dd, J=7.2, 3.5 Hz, 2H), 2.27-2.22 (m, 1H), 1.28 (d, J=6.7 Hz, 3H), 1.04 (dd, J=6.6, 1.8 Hz, 6H), 0.79-0.70 (m, 2H), −0.16 (s, 9H).

Step 6: Synthesis of Compound 21-6

Compound 21-5 (0.16 g), dimethylsulfoximine (0.027 g), tris(dibenzylideneacetone)dipalladium (0.012 g), 4,5-bisdiphenylphosphino-9,9-dimethylxanthene (0.016 g), cesium carbonate (0.175 g) and dioxane (5 mL) were mixed and, under nitrogen atmosphere, heated to 80° C. and left to react for 1 h. After filtration under vacuum, the filtrate was concentrated. The resulting crude product was then separated and purified by column chromatography (petroleum ether:ethyl acetate=1:1) to give compound 21-6 (0.17 g).

MS: (ESI, $[M+H]^+$) m/z: 562.26

$^{1}$H NMR (500 MHz, $CDCl_3$) δ 7.62 (d, J=1.9 Hz, 1H), 6.54 (d, J=1.9 Hz, 1H), 6.24 (s, 1H), 5.74 (q, J=11.0 Hz, 2H), 4.32-4.29 (m, 1H), 3.98 (dd, J=11.3, 3.7 Hz, 1H), 3.91 (dd, J=13.2, 2.9 Hz, 1H), 3.77 (d, J=11.3 Hz, 1H), 3.71 (dd, J=11.4, 3.1 Hz, 1H), 3.56 (td, J=11.8, 3.1 Hz, 1H), 3.44-3.36 (m, 2H), 3.27 (d, J=1.4 Hz, 6H), 3.20 (td, J=12.7, 3.8 Hz, 1H), 2.80 (dd, J=7.1, 3.3 Hz, 2H), 2.18 (hept, J=6.8 Hz, 1H), 1.25 (d, J=6.5 Hz, 3H), 0.98 (dd, J=6.6, 1.5 Hz, 6H), 0.78-0.70 (m, 2H), −0.15 (s, 9H).

Step 7: Synthesis of Compound 21

Compound 21-6 was dissolved in dichloromethane (10 mL), and triethylsilane (207 mg) and trifluoroacetic acid (2.115 mL) were added. The mixture was left to react at room temperature for half an hour. The pH was adjusted to 8 with a saturated solution of sodium bicarbonate. The organic phase was washed with a saturated solution of sodium bicarbonate and saturated brine successively and dried over anhydrous sodium sulfate. After filtration under vacuum and concentration, the resulting crude product was separated and purified by column chromatography (dichloromethane:methanol=20:1) to give compound 21 (0.067 g).

HRMS: (ESI, $[M+H]^+$) m/z: 432.2175.

$^{1}$H NMR (500 MHz, Chloroform-d) δ 7.58 (d, J=2.1 Hz, 1H), 6.72 (d, J=2.1 Hz, 1H), 6.27 (s, 1H), 4.36-4.34 (m, 1H), 4.05 (dd, J=11.3, 3.7 Hz, 1H), 3.92 (dd, J=13.0, 3.0 Hz, 1H), 3.88-3.73 (m, 2H), 3.64 (td, J=11.8, 3.1 Hz, 1H), 3.35-3.28

(m, 7H), 2.82 (d, J=7.1 Hz, 2H), 2.22-2.17 (m, 1H), 1.31 (d, J=6.7 Hz, 3H), 0.97 (d, J=6.6 Hz, 6H).
Example 22: Synthesis of Compound 22
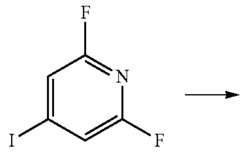
A1-3
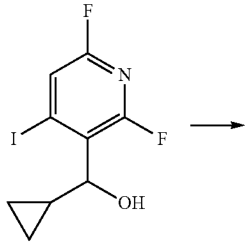
22-1
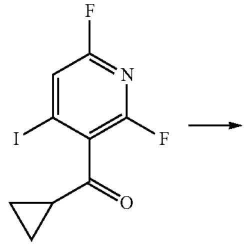
22-2
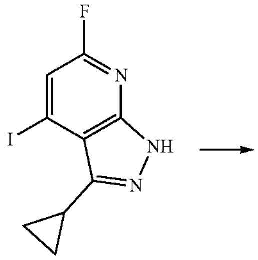
22-3
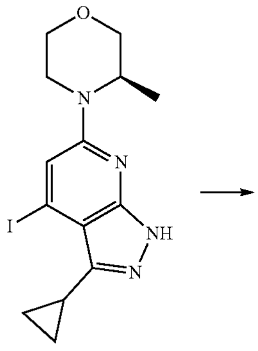
22-4
-continued
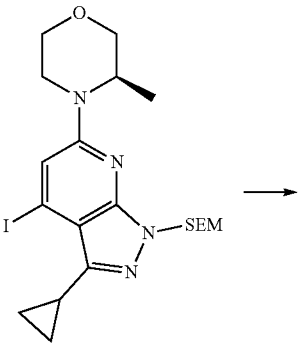
22-5
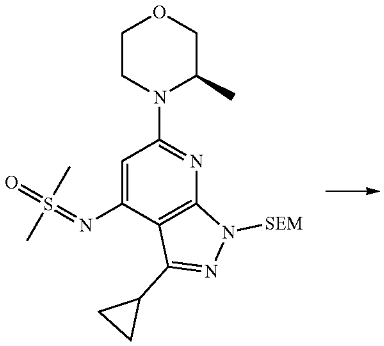
22-6
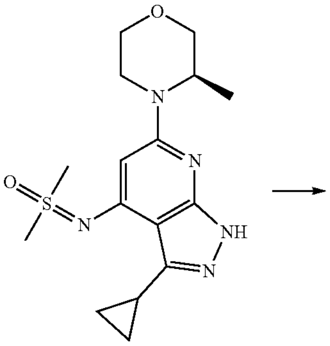
22-7
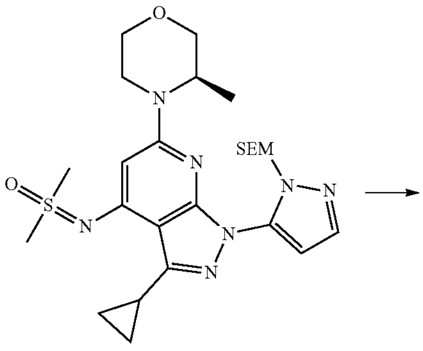
22-8

-continued

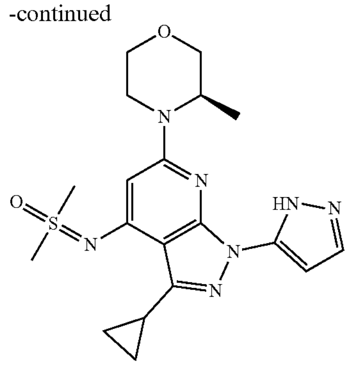

22

Step 1: Synthesis of Compound 22-1

Compound A1-3 (6 g) and tetrahydrofuran (60 mL) were mixed and cooled to −78° C., and lithium diisopropylamide (2 M, 18.6 mL) was added dropwise under nitrogen atmosphere. The mixture was left to react at −78° C. for 1 h. Cyclopropylformaldehyde (3.5 g) was added to the reaction solution. The reaction solution was stirred at −78° C. for another 1 h and then warmed to room temperature. A saturated aqueous solution of ammonium chloride was added. The organic phase was washed with water and saturated brine successively and dried over anhydrous sodium sulfate. After filtration and concentration, the crude product was separated and purified by column chromatography (petroleum ether:ethyl acetate=5:1) to give compound 22-1 (6 g).

$^1$H NMR (500 MHz, $CDCl_3$) δ 7.33 (d, J=3.1 Hz, 1H), 4.36-4.23 (m, 1H), 2.39 (dd, J=6.7, 2.5 Hz, 1H), 1.59-1.54 (m, 1H), 0.80-0.64 (m, 1H), 0.62-0.43 (m, 3H).

Step 2: Synthesis of Compound 22-2

Compound 22-1 (6 g), manganese dioxide (33.5 g) and toluene (60 mL) were mixed, heated to 90° C. and left to react for 3 h. After filtration under vacuum, the filtrate was concentrated to give compound 22-2 (5.8 g).

$^1$H NMR (500 MHz, $CDCl_3$) δ 7.40 (d, J=2.8 Hz, 1H), 2.39-2.15 (m, 1H), 1.45-1.38 (m, 2H), 1.22-1.08 (m, 2H).

Step 3: Synthesis of Compound 22-3

Compound 22-2 (5.7 g) and tetrahydrofuran (60 mL) were mixed, and a solution of hydrazine in tetrahydrofuran (1 M, 0.743 mL) was added. After 1 h of reaction, an additional solution of hydrazine in tetrahydrofuran (1 M, 0.338 mL) was added, and the mixture was left to react overnight at room temperature. The reaction solution was concentrated and then separated and purified by column chromatography (petroleum ether:ethyl acetate=4:1) to give compound 22-3 (2.4 g).

MS: (ESI, $[M+H]^+$) m/z: 303.82.

$^1$H NMR (500 MHz, DMSO-$d_6$) δ 13.48 (s, 1H), 7.51 (s, 1H), 2.61-2.55 (m, 1H), 1.03-0.98 (m, 4H).

Step 4: Synthesis of Compound 22-4

Compound 22-3 (2.4 g), (R)-3-methylmorpholine (4.00 g) and dimethyl sulfoxide (50 mL) were mixed, heated to 120° C. and left to react. The reaction mixture was cooled to room temperature, diluted with ethyl acetate, washed with water and saturated brine successively, and dried over anhydrous sodium sulfate. After filtration under vacuum, the filtrate was concentrated to give compound 22-4 (2.9 g).

MS: (ESI, $[M+H]^+$) m/z: 385.01.

$^1$H NMR (500 MHz, $CDCl_3$) δ 10.10 (brs, 1H), 6.99 (s, 1H), 4.40-4.26 (m, 1H), 4.03 (dd, J=11.5, 3.9 Hz, 1H), 3.90 (dd, J=13.2, 3.0 Hz, 1H), 3.82-3.74 (m, 2H), 3.61 (td, J=11.9, 3.1 Hz, 1H), 3.30 (td, J=12.7, 3.9 Hz, 1H), 2.53-2.44 (m, 1H), 1.29 (d, J=6.8 Hz, 3H), 1.05-1.03 (m, 2H), 1.03-1.00 (m, 2H).

Step 5: Synthesis of Compound 22-5

Compound 22-4 (2.9 g) and N,N-dimethylformamide (50 mL) were mixed, and 60% sodium hydride (0.362 g) was added under ice-bath conditions. After 0.5 h of reaction, 2-(trimethylsilyl)ethoxymethyl chloride (2.008 mL) was added dropwise. The mixture was left to react at room temperature for 1 h. A saturated aqueous solution of ammonium chloride was added, and the mixture was stirred for 5 min and extracted with ethyl acetate. The organic phase was washed with water and saturated brine successively, dried over anhydrous sodium sulfate and filtered under vacuum, and the filtrate was concentrated. The resulting crude product was then separated and purified by silica gel column chromatography (petroleum ether:ethyl acetate=10:1) to give compound 22-5 (3.2 g).

MS: (ESI, $[M+H]^+$) m/z: 515.14.

$^1$H NMR (500 MHz, $CDCl_3$) δ 6.97 (s, 1H), 5.56 (s, 2H), 4.35 (dd, J=6.9, 2.9 Hz, 1H), 4.07-3.97 (m, 2H), 3.86-3.71 (m, 2H), 3.71-3.49 (m, 3H), 3.26 (td, J=12.7, 3.8 Hz, 1H), 2.49-2.46 (m, 1H), 1.28 (d, J=6.8 Hz, 3H), 1.07-1.05 (m, 2H), 1.01-0.99 (m, 2H), 0.93-0.89 (m, 2H), −0.06 (s, 9H).

Step 6: Synthesis of Compound 22-6

Compound 22-5 (0.259 g), tris(dibenzylideneacetone)dipalladium (0.116 g), 4,5-bisdiphenylphosphino-9,9-dimethylxanthene (0.146 g), cesium carbonate (1.647 g) and dioxane (20 mL) were mixed and, under nitrogen atmosphere, heated to 80° C. and left to react for 2 h. The reaction mixture was naturally cooled to room temperature and filtered under vacuum, and the filtrate was condensed. The resulting crude product was then separated and purified by silica gel column chromatography (petroleum ether:ethyl acetate=1:1) to give compound 22-6 (1.2 g).

MS: (ESI, $[M+H]^+$) m/z: 480.29.

$^1$H NMR (500 MHz, $CDCl_3$) δ 6.22 (s, 1H), 5.55 (s, 2H), 4.44-4.25 (m, 1H), 3.98 (td, J=14.0, 12.9, 3.3 Hz, 2H), 3.77 (t, J=2.5 Hz, 2H), 3.60 (tdd, J=9.5, 4.8, 3.0 Hz, 3H), 3.26 (s, 7H), 2.43 (tt, J=8.3, 5.1 Hz, 1H), 1.25 (d, J=6.7 Hz, 3H), 1.05 (dt, J=5.9, 2.9 Hz, 2H), 1.02-0.82 (m, 4H), −0.07 (s, 9H).

Step 7: Synthesis of Compound 22-7

Compound 22-6 (1.2 g) was dissolved in dichloromethane (60 mL), and triethylsilane (4.00 mL) and trifluoroacetic acid (29.7 mL) were added. The mixture was left to react at room temperature for half an hour. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=20:1) to give compound 22-7 (0.82 g).

$^1$H NMR (500 MHz, $CDCl_3$) δ 9.91 (brs, 1H), 6.23 (s, 1H), 4.33-4.29 (m, 1H), 4.00 (dd, J=11.4, 3.7 Hz, 1H), 3.87 (dd, J=13.1, 2.9 Hz, 1H), 3.78 (d, J=2.1 Hz, 2H), 3.62 (td, J=11.8, 3.1 Hz, 1H), 3.29-3.24 (m, 7H), 2.48-2.43 (m, 1H), 1.26 (d, J=6.7 Hz, 3H), 1.08-0.97 (m, 2H), 0.92-0.89 (m, 2H).

Step 8: Synthesis of Compound 22-8

Compound 22-7 (400 mg), 3-iodo-1-((2-(trimethylsilyl)ethoxy)methyl)-1H-pyrazole (742 mg), cesium carbonate (1119 mg), (1R,2R)—N1,N2-dimethylcyclohexane-1,2-diamine (326 mg), copper(I) iodide (327 mg) and N-methylpyrrolidone (20 mL) were mixed and, under nitrogen atmosphere, microwaved (400 W) to 140° C. and left to react for 1 h. The reaction mixture was cooled to room temperature, then diluted with ammonium hydroxide (10 mL) and ethyl acetate, washed with water and a saturated aqueous solution of sodium chloride, and dried over anhydrous sodium sulfate. After filtration under vacuum, the filtrate was condensed. The resulting crude product was then separated and purified by silica gel column chromatography (petroleum ether:ethyl acetate=1:4) to give compound 22-8 (0.442 g).

MS: (ESI, [M+H]$^+$) m/z: 546.27.

$^1$H NMR (500 MHz, $CDCl_3$) δ 7.58 (d, J=2.4 Hz, 1H), 7.06 (d, J=2.4 Hz, 1H), 6.27 (s, 1H), 5.46 (s, 2H), 4.36-4.33 (m, 1H), 4.03 (dd, J=11.4, 3.7 Hz, 1H), 3.97 (dd, J=13.2, 2.9 Hz, 1H), 3.87-3.76 (m, 2H), 3.69-3.54 (m, 3H), 3.32-3.26 (m, 7H), 2.52-2.47 (m, 1H), 1.29 (d, J=6.8 Hz, 3H), 1.20 (dd, J=7.6, 5.2 Hz, 2H), 0.95-0.88 (m, 4H), −0.02 (s, 9H).

Step 9: Synthesis of Compound 22

Compound 22-8 (0.2 g) was dissolved in dichloromethane (10 mL), and triethylsilane (0.585 mL) and trifluoroacetic acid (4.36 mL) were added. The reaction was stirred at room temperature for half an hour. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=20:1) to give compound 22 (0.037 g).

HRMS: (ESI, [M+H]$^+$) m/z: 416.1866.

$^1$H NMR (500 MHz, $CDCl_3$) δ 7.56 (d, J=2.1 Hz, 1H), 6.69 (s, 1H), 6.28 (s, 1H), 4.37-4.32 (m, 1H), 4.05 (dd, J=11.4, 3.7 Hz, 1H), 3.91 (dd, J=13.0, 2.9 Hz, 1H), 3.88-3.71 (m, 2H), 3.64 (td, J=11.8, 3.1 Hz, 1H), 3.34-3.29 (m, 7H), 2.51-2.47 (m, 1H), 1.30 (d, J=6.7 Hz, 3H), 1.16-1.14 (m, 2H), 0.95-0.93 (m, 2H).

Example 23: Synthesis of Compound 23

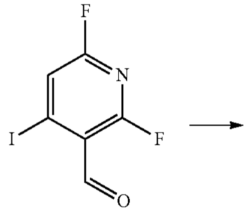

A1-4

-continued

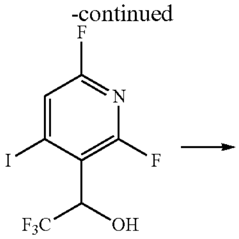

23-1

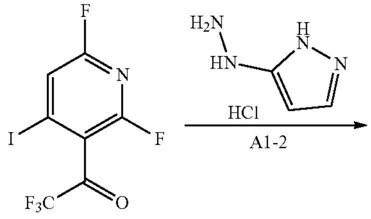

23-2

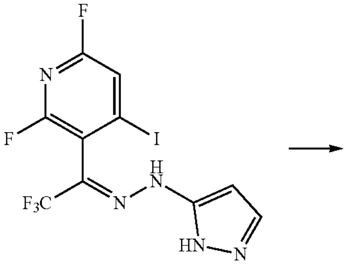

23-3

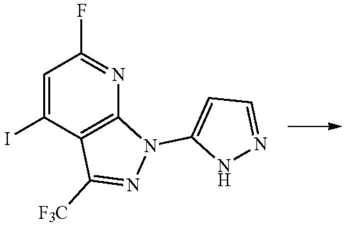

23-4

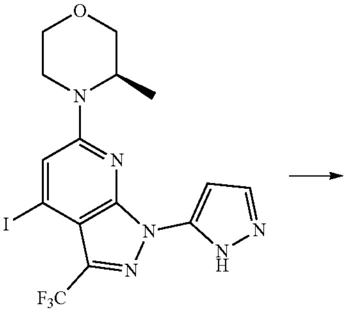

23-5

-continued

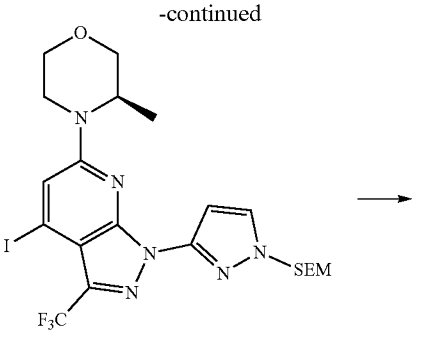

23-6

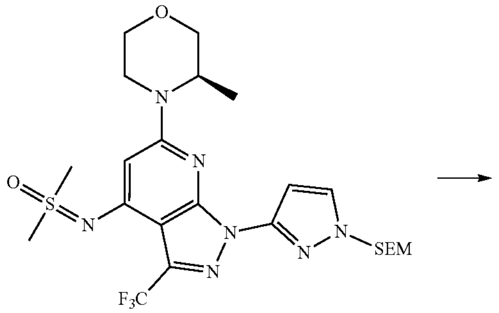

23-7

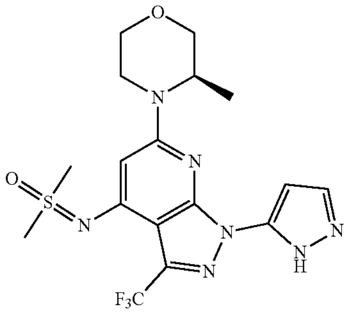

23

Step 1: Synthesis of Compound 23-1

Compound A1-4 (2.5 g) was dissolved in tetrahydrofuran (30 mL), and trifluoromethyl trimethylsilane (3.75 g) was added dropwise under nitrogen atmosphere. The mixture was left to react at room temperature for 10 min. Tetrabutylammonium fluoride (0.1 mL) was added. The mixture was left to react at room temperature for 30 min, and an aqueous solution of hydrochloric acid (6N, 1.1 mL) was added. The mixture was stirred at room temperature for 5 h, diluted with ethyl acetate, washed with water and saturated brine successively, and dried over anhydrous sodium sulfate. After filtration and concentration, the resulting crude product was separated and purified by column chromatography (petroleum ether:ethyl acetate=5:1) to give compound 23-1 (1.9 g).

Step 2: Synthesis of Compound 23-2

Compound 23-1 (1.9 g), manganese dioxide (4 g) and toluene (30 mL) were mixed and left to react at 70° C. for 5 h. The reaction solution was filtered and washed, and the mother liquor was collected and concentrated to give compound 23-2 (1.3 g).

MS: (ESI, $[M+H]^+$) m/z: 338.42.

Step 3: Synthesis of Compound 23-3

Compound A1-2 (3 g), compound 23-2 (1.1 g) and ethanol (15 mL) were mixed and left to react at room temperature for 1 h. The reaction solution was concentrated, and the residue was dissolved in ethyl acetate. The solution was washed with saturated sodium bicarbonate, water and saturated brine successively, dried over anhydrous sodium sulfate, filtered, and concentrated to give compound 23-3 (550 mg).

MS: (ESI, $[M+H]^+$) m/z: 418.03.

$^1H$ NMR (500 MHz, DMSO-$d_6$) δ 12.25 (s, 1H), 10.76 (s, 1H), 8.00 (s, 1H), 7.60 (d, J=12.3 Hz, 1H), 5.99 (d, J=15.8 Hz, 1H).

Step 4: Synthesis of Compound 23-4

Compound 23-3 (500 mg) and N-methylpyrrolidone (5 mL) were mixed, microwaved to 200° C. and left to react for 20 min. Water was added to the reaction solution, and a solid precipitated. The solid was collected by filtration, washed and dried to give compound 23-4 (200 mg).

MS (ESI, $[M+H]^+$) m/z: 398.00.

$^1H$ NMR (500 MHz, DMSO-$d_6$) δ 13.32 (s, 1H), 8.01 (d, J=8.4 Hz, 2H), 6.74 (s, 1H).

Step 5: Synthesis of Compound 23-5

Compound 23-4 (170 mg), (R)-3-methylmorpholine (100 mg) and dimethyl sulfoxide (3 mL) were mixed, heated to 120° C. and left to react for 1 h. Water was added to the reaction solution, and a solid precipitated. The solid was collected by filtration, washed and dried to give compound 23-5 (150 mg).

MS (ESI, $[M+H]^+$) m/z: 479.10.

$^1H$ NMR (500 MHz, DMSO-$d_6$) δ 13.15 (s, 1H), 7.92 (s, 1H), 7.55 (s, 1H), 6.80 (s, 1H), 4.47 (d, J=5.3 Hz, 1H), 4.06 (d, J=12.4 Hz, 1H), 3.95 (dd, J=11.4, 3.2 Hz, 1H), 3.74 (d, J=11.5 Hz, 1H), 3.62 (dd, J=11.5, 2.8 Hz, 1H), 3.47 (td, J=11.9, 2.8 Hz, 1H), 3.19 (td, J=12.8, 3.6 Hz, 1H), 1.20 (d, J=6.6 Hz, 3H).

Step 6: Synthesis of Compound 23-6

Compound 23-5 (150 mg), diisopropylethylamine (105 mg) and dichloromethane (10 mL) were mixed, and 2-(trimethylsilyl)ethoxymethyl chloride (89 mg) was added dropwise. The mixture was left to react at room temperature for 30 min. Dichloromethane (30 mL) and saturated sodium bicarbonate (30 mL) were added to the reaction solution. The organic phase was separated and concentrated, and the resulting crude product was separated and purified by column chromatography (petroleum ether:ethyl acetate=3:1) to give compound 23-6 (110 mg).

MS (ESI, $[M+H]^+$) m/z: 609.30.

Step 7: Synthesis of Compound 23-7

Compound 23-6 (110 mg), dimethylsulfoximine (33.7 mg), tris(dibenzylideneacetone)dipalladium (8.28 mg), 4,5-bisdiphenylphosphino-9,9-dimethylxanthene (10.46 mg), cesium carbonate (118 mg) and 1,4-dioxane (5 mL) were mixed and left to react at 80° C. for 1 h under nitrogen atmosphere. The reaction solution was filtered, and the filtrate was concentrated. The crude product was then separated and purified by column chromatography (dichloromethane:methanol=15:1) to give compound 23-7 (90 mg).

MS (ESI, $[M+H]^+$) m/z: 574.17.

Step 8: Synthesis of Compound 23

Compound 23-7 (90 mg) was dissolved in dichloromethane (4 mL). The solution was cooled to 0° C., and triethylsilane (182 mg) and trifluoroacetic acid (2.8 g) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=9:1) to give compound 23 (40 mg).

MS (ESI, $[M+H]^+$) m/z: 444.16.

$^1$H NMR (500 MHz, DMSO-$d_6$) δ 12.97 (s, 1H), 7.88 (s, 1H), 6.81 (s, 1H), 6.28 (s, 1H), 4.32 (d, J=5.0 Hz, 1H), 4.03-3.88 (m, 2H), 3.75 (d, J=11.3 Hz, 1H), 3.64 (dd, J=11.3, 2.6 Hz, 1H), 3.48 (td, J=11.7, 2.6 Hz, 1H), 3.39 (s, 6H), 3.14 (td, J=12.7, 3.6 Hz, 1H), 1.19 (d, J=6.7 Hz, 3H).

Example 24: Synthesis of Compound 24

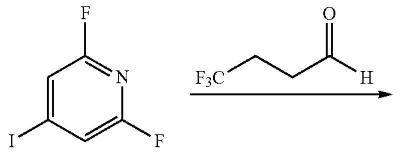

A1-3

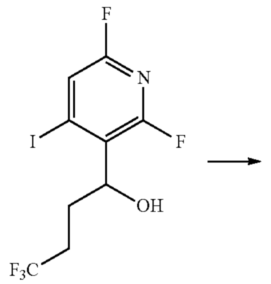

24-1

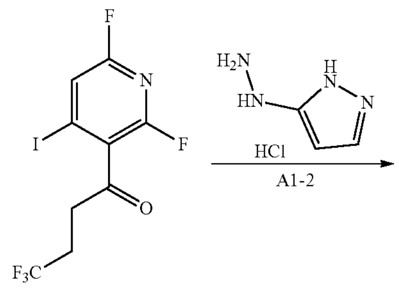

24-2

-continued

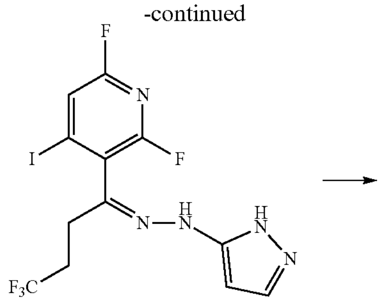

24-3

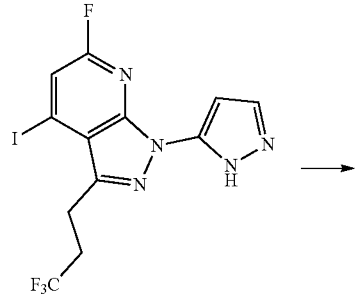

24-4

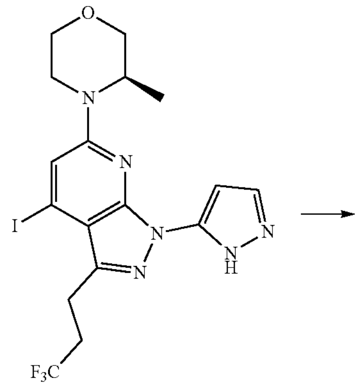

24-5

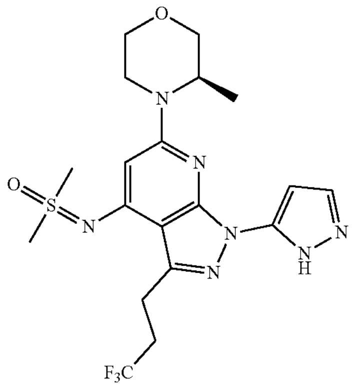

24

Step 1: Synthesis of Compound 24-1

Compound A1-3 (1.3 g) and tetrahydrofuran (30 mL) were mixed and cooled to −78° C., and a solution of lithium diisopropylamide in tetrahydrofuran/n-hexane (2 M, 3.5 mL) was added dropwise. The mixture was left to react at −78° C. for 1 h. A1-2 (1 g) was added to the reaction solution, and the mixture was left to react at −78° C. for another 30 min. Formic acid (0.5 g) and ethyl acetate (100 mL) were then added, and the reaction solution was warmed to room temperature. The organic phase was washed with water and saturated brine successively and dried over anhydrous sodium sulfate. After filtration and concentration, the crude product was separated and purified by column chromatography (petroleum ether:ethyl acetate=5:1) to give compound 24-1 (1.3 g).

$^1$H NMR (500 MHz, DMSO-$d_6$) δ 7.76 (s, 1H), 5.88 (d, J=4.6 Hz, 1H), 4.95 (dt, J=9.3, 4.7 Hz, 1H), 2.49-2.37 (m, 1H), 2.37-2.23 (m, 1H), 2.05 (m, 1H), 1.85 (m, 1H).

Step 2: Synthesis of Compound 24-2

Compound 11-1 (1.3 g), manganese dioxide (4 g) and toluene (30 mL) were mixed and left to react at 70° C. for 5 h. The reaction solution was filtered and washed, and the mother liquor was collected and concentrated to give compound 24-2 (1 g).

$^1$H NMR (500 MHz, DMSO-$d_6$)(7.93 (d, J=2.1 Hz, 1H), 3.21 (t, J=7.0 Hz, 2H), 2.79-2.59 (m, 2H).

Step 3: Synthesis of Compound 24-3

Compound A1-2 (1 g), compound 24-2 (1 g) and ethanol (20 mL) were mixed and left to react at room temperature for 1 h. The reaction solution was concentrated, and the residue was dissolved in ethyl acetate. The solution was washed with saturated sodium bicarbonate, water and saturated brine successively, dried over anhydrous sodium sulfate, filtered, and concentrated to give compound 24-3 (600 mg).

MS: (ESI, [M+H]$^+$) m/z: 446.31.

Step 4: Synthesis of Compound 24-4

Compound 24-3 (600 mg) and N-methylpyrrolidone (5 mL) were mixed, microwaved to 200° C. and left to react for 20 min. Water was added to the reaction solution, and a solid precipitated. The solid was collected by filtration, washed and dried to give compound 24-4 (250 mg).

MS (ESI, [M+H]$^+$) m/z: 426.01.

Step 5: Synthesis of Compound 24-5

Compound 24-4 (250 mg), (R)-3-methylmorpholine (200 mg) and dimethyl sulfoxide (3 mL) were mixed, heated to 120° C. and left to react for 1 h. Water was added to the reaction solution, and a solid precipitated. The solid was collected by filtration, washed and dried to give compound 24-5 (170 mg).

MS (ESI, [M+H]$^+$) m/z: 507.04.

$^1$H NMR (500 MHz, DMSO-$d_6$) δ 13.09 (s, 1H), 7.92 (s, 1H), 7.70 (s, 1H), 6.64 (s, 1H), 3.50-3.41 (m, 2H), 3.31 (t, J=7.1 Hz, 4H), 2.95-2.79 (m, 2H), 2.18 (t, J=8.1 Hz, 3H), 1.98-1.84 (m, 3H).

Step 6: Synthesis of Compound 24

Compound 24-5 (100 mg), dimethylsulfoximine (37 mg), tris(dibenzylideneacetone)dipalladium (9 mg), 4,5-bisdiphenylphosphino-9,9-dimethylxanthene (11 mg), cesium carbonate (193 mg) and 1,4-dioxane (5 mL) were mixed and left to react at 80° C. for 1 h under nitrogen atmosphere. The reaction solution was filtered, and the filtrate was concentrated. The crude product was then separated and purified by column chromatography (dichloromethane:methanol=15:1) to give compound 24 (50 mg).

MS (ESI, [M+H]$^+$) m/z: 472.21.

$^1$H NMR (500 MHz, DMSO-$d_6$)(δ 12.68 (s, 1H), 7.78 (s, 1H), 6.76 (s, 1H), 6.13 (s, 1H), 4.30 (d, J=5.4 Hz, 1H), 3.96 (dd, J=11.1, 2.6 Hz, 1H), 3.88 (d, J=12.6 Hz, 1H), 3.75 (d, J=11.3 Hz, 1H), 3.64 (dd, J=11.3, 2.5 Hz, 1H), 3.53-3.45 (m, 1H), 3.41 (s, 6H), 3.21-3.05 (m, 3H), 2.73 (dq, J=22.3, 11.3 Hz, 2H), 1.17 (d, J=6.6 Hz, 3H).

Example 25: Synthesis of Compound 25

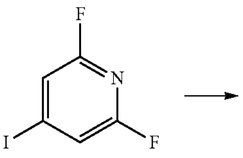

A1-3

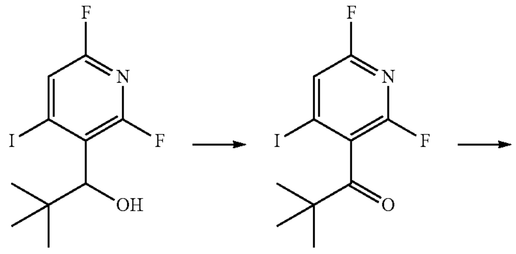

25-1 25-2

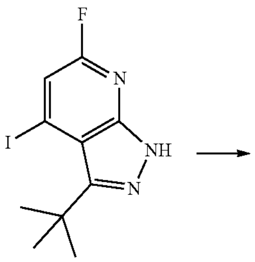

25-3

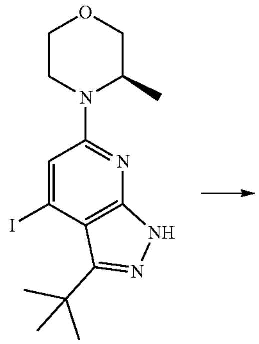

25-4

-continued

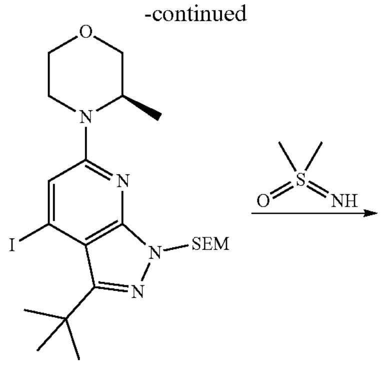

25-5

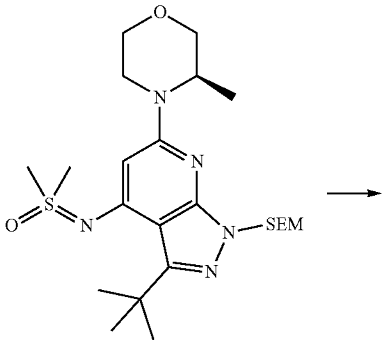

25-6

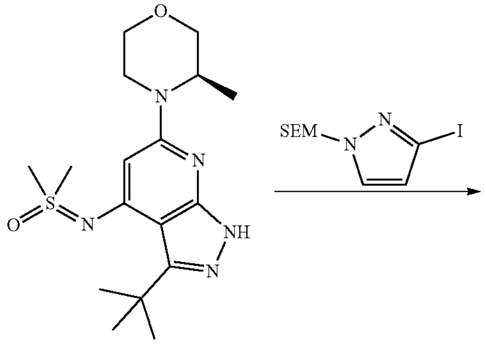

25-7

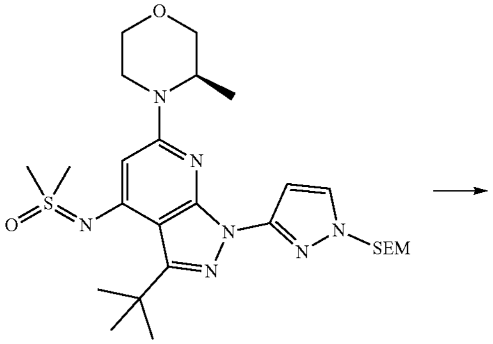

25-8

-continued

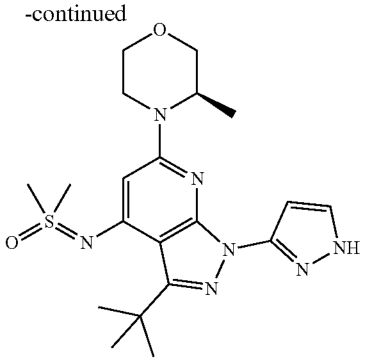

25

Step 1: Synthesis of Compound 25-1

Compound A1-3 (10 g) and tetrahydrofuran (100 mL) were mixed and cooled to −78° C., and a solution of lithium diisopropylamide in tetrahydrofuran/n-hexane (2 M, 29 mL) was added dropwise. The mixture was left to react at −78° C. for 1 h. Pivalaldehyde (7.15 g) was added to the reaction solution, and the mixture was left to react at −78° C. for another 30 min. Formic acid (3.82 g) and ethyl acetate (100 mL) were then added, and the reaction solution was warmed to room temperature. The organic phase was washed with water and saturated brine successively and dried over anhydrous sodium sulfate. After filtration and concentration, the crude product was separated and purified by column chromatography (petroleum ether:ethyl acetate=5:1) to give compound 25-1 (9.7 g).

Step 2: Synthesis of Compound 25-2

Compound 25-1 (9.5 g) and toluene (180 mL) were mixed, heated to 70° C. and left to react overnight. The reaction solution was filtered and concentrated to give compound 25-2 (9.3 g).

Step 3: Synthesis of Compound 25-3

Compound 25-2 (9 g) and tetrahydrofuran (90 mL) were mixed and cooled to 0° C., and a solution of hydrazine in tetrahydrofuran (1 M, 30 mL) was added dropwise. The mixture was left to react overnight at room temperature. The reaction solution was concentrated, and the crude product was separated and purified by column chromatography (petroleum ether:ethyl acetate=2:1) to give compound 25-3 (2.9 g).

MS (ESI, $[M-H]^-$) m/z: 317.83.

$^1H$ NMR (500 MHz, DMSO-$d_6$) δ 13.59 (s, 1H), 7.65 (s, 1H), 1.61 (s, 9H).

Step 4: Synthesis of Compound 25-4

Compound 25-3 (2.8 g), (R)-3-methylmorpholine (4.44 g) and dimethyl sulfoxide (15 mL) were mixed, heated to 120° C. and left to react overnight. Ethyl acetate (100 mL) was added to the reaction solution. The organic phase was washed with water and saturated brine successively and dried over anhydrous sodium sulfate. After filtration and concentration, the crude product was separated and purified by column chromatography (petroleum ether:ethyl acetate=2:1) to give compound 25-4 (3.2 g).

MS (ESI, $[M+H]^+$) m/z: 401.10.

$^1H$ NMR (500 MHz, DMSO-$d_6$) δ 12.68 (s, 1H), 7.28 (s, 1H), 4.43-4.31 (m, 1H), 3.97-3.84 (m, 2H), 3.71 (d, J=11.3 Hz, 1H), 3.62 (dd, J=11.4, 2.8 Hz, 1H), 3.46 (td, J=11.8, 2.9 Hz, 1H), 3.11 (td, J=12.7, 3.7 Hz, 1H), 1.56 (s, 9H), 1.15 (d, J=6.7 Hz, 3H).

Step 5: Synthesis of Compound 25-5

Compound 25-4 (3 g) and N,N-dimethylformamide (15 mL) were mixed and cooled to 0° C., and 60% sodium hydride (360 mg) was added portionwise. The mixture was left to react at 0° C. for 0.5 h. 2-(Trimethylsilyl)ethoxymethyl chloride (1.87 g) was added to the reaction solution, and the mixture was left to react at 0° C. for 0.5 h. Ethyl acetate (150 mL) and saturated ammonium chloride (50 mL) were added to the reaction solution. The organic phase was separated, washed with water and saturated brine successively and concentrated. The resulting crude product was separated and purified by column chromatography (petroleum ether:ethyl acetate=1:1) to give compound 25-5 (3.64 g).

MS (ESI, $[M+H]^+$) m/z: 531.12.

$^1H$ NMR (500 MHz, DMSO-$d_6$) δ 7.34 (s, 1H), 5.50 (s, 2H), 4.47-4.38 (m, 1H), 4.01-3.90 (m, 2H), 3.72 (d, J=11.3 Hz, 1H), 3.62-3.55 (m, 3H), 3.45 (td, J=11.8, 2.9 Hz, 1H), 3.12 (td, J=12.8, 3.7 Hz, 1H), 1.57 (s, 9H), 1.16 (d, J=6.7 Hz, 3H), 0.83-0.75 (m, 2H), −0.12 (s, 9H).

Step 6: Synthesis of Compound 25-6

Compound 25-5 (1.5 g), dimethylsulfoximine (290 mg), tris(dibenzylideneacetone)dipalladium (129 mg), 4,5-bisdiphenylphosphino-9,9-dimethylxanthene (164 mg), cesium carbonate (1.84 g) and 1,4-dioxane (20 mL) were mixed and left to react at 80° C. for 1 h under nitrogen atmosphere. The reaction solution was filtered, and the filtrate was concentrated. The crude product was then separated and purified by column chromatography (petroleum ether:ethyl acetate=1:1) to give compound 25-6 (1.02 g).

MS (ESI, $[M+H]^+$) m/z: 496.30.

$^1H$ NMR (500 MHz, DMSO-$d_6$) δ 6.13 (s, 1H), 5.44 (s, 2H), 4.33-4.24 (m, 1H), 3.94 (dd, J=11.2, 3.3 Hz, 1H), 3.89-3.83 (m, 1H), 3.73 (d, J=11.2 Hz, 1H), 3.62 (dd, J=11.4, 2.7 Hz, 1H), 3.60-3.54 (m, 2H), 3.47 (td, J=11.8, 3.0 Hz, 1H), 3.38 (s, 6H), 3.07 (td, J=12.7, 3.7 Hz, 1H), 1.43 (s, 9H), 1.14 (d, J=6.7 Hz, 3H), 0.87-0.75 (m, 2H), −0.10 (s, 9H).

Step 7: Synthesis of Compound 25-7

Compound 25-6 (1 g) was dissolved in dichloromethane (10 mL). The solution was cooled to 0° C., and triethylsilane (2.93 g) and trifluoroacetic acid (30 mL) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (petroleum ether:ethyl acetate=1:4) to give compound 25-7 (636 mg).

MS (ESI, $[M+H]^+$) m/z: 366.19.

$^1H$ NMR (500 MHz, DMSO-$d_6$) δ 12.08 (s, 1H), 6.09 (s, 1H), 4.27-4.18 (m, 1H), 3.93 (dd, J=11.2, 3.3 Hz, 1H), 3.80-3.68 (m, 2H), 3.63 (dd, J=11.3, 2.8 Hz, 1H), 3.47 (td, J=11.8, 3.0 Hz, 1H), 3.36 (s, 6H), 3.06 (td, J=12.6, 3.7 Hz, 1H), 1.42 (s, 9H), 1.13 (d, J=6.7 Hz, 3H).

Step 8: Synthesis of Compound 25-8

Compound 25-7 (400 mg), 3-iodo-1-((2-(trimethylsilyl) ethoxy)methyl)-1H-pyrazole (532 mg), copper(I) iodide (313 mg), (1R,2R)-cyclohexane-1,2-diamine (375 mg), cesium carbonate (1.07 g) and N-methylpyrrolidinone (10 mL) were mixed, microwaved to 140° C. and left to react for 1 h.

Ethyl acetate (100 mL) was added to the reaction solution. The organic phase was washed with 1 M ammonium hydroxide, water and saturated brine successively, and dried over anhydrous sodium sulfate. The filtrate was concentrated, and the crude product was then separated and purified by column chromatography (petroleum ether:ethyl acetate=1:1) to give compound 25-8 (88 mg).

MS (ESI, $[M+H]^+$) m/z: 562.30.

$^1H$ NMR (500 MHz, DMSO-$d_6$) δ 7.94 (d, J=2.2 Hz, 1H), 6.86 (d, J=2.2 Hz, 1H), 6.19 (s, 1H), 5.41 (s, 2H), 4.31-4.21 (m, 1H), 3.95 (dd, J=11.2, 3.0 Hz, 1H), 3.84 (d, J=12.0 Hz, 1H), 3.75 (d, J=11.2 Hz, 1H), 3.64 (dd, J=11.2, 2.5 Hz, 1H), 3.61-3.55 (m, 2H), 3.49 (td, J=11.7, 2.6 Hz, 1H), 3.41 (s, 6H), 3.11 (td, J=12.6, 3.6 Hz, 1H), 1.47 (s, 9H), 1.16 (d, J=6.7 Hz, 3H), 0.88-0.84 (m, 2H), −0.03 (s, 9H).

Step 9: Synthesis of Compound 25

Compound 25-8 (80 mg) was dissolved in dichloromethane (1 mL). The solution was cooled to 0° C., and triethylsilane (331 mg) and trifluoroacetic acid (3 mL) were added. The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=20:1) to give compound 25 (48 mg).

HRMS: (ESI, $[M+H]^+$) m/z: 432.2180.

$^1H$ NMR (500 MHz, DMSO-$d_6$) δ 12.63 (s, 1H), 7.75 (s, 1H), 6.72 (s, 1H), 6.18 (s, 1H), 4.30-4.22 (m, 1H), 3.95 (dd, J=11.2, 3.3 Hz, 1H), 3.84 (d, J=12.0 Hz, 1H), 3.75 (d, J=11.2 Hz, 1H), 3.64 (dd, J=11.3, 2.8 Hz, 1H), 3.48 (td, J=11.8, 3.0 Hz, 1H), 3.41 (s, 6H), 3.10 (td, J=12.6, 3.7 Hz, 1H), 1.48 (s, 9H), 1.16 (d, J=6.7 Hz, 3H).

Example 26: Synthesis of Compound 26

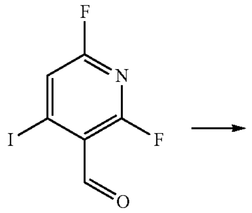

A1-4

-continued
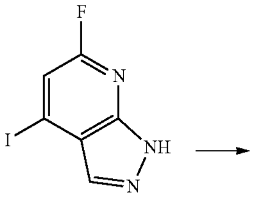
26-1
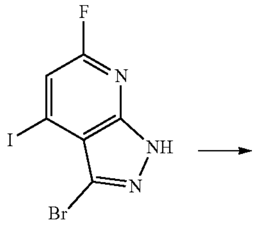
26-2
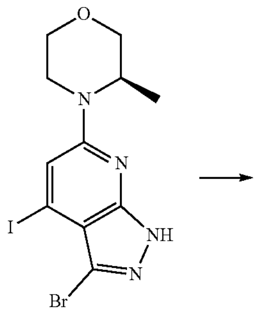
26-3
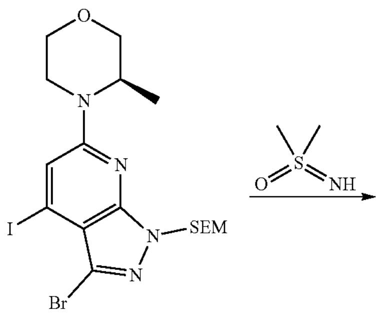
26-4
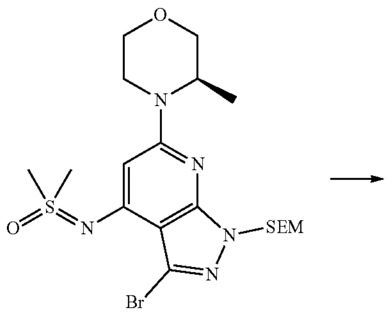
26-5
-continued
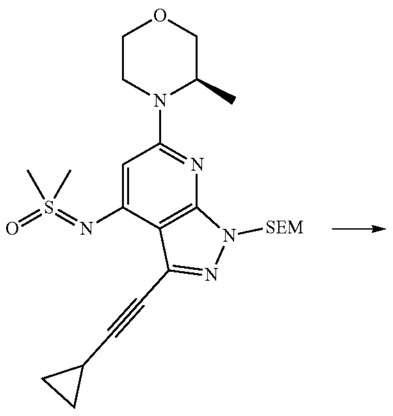
26-6
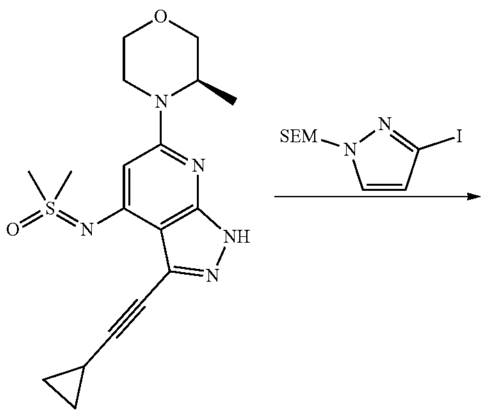
26-7
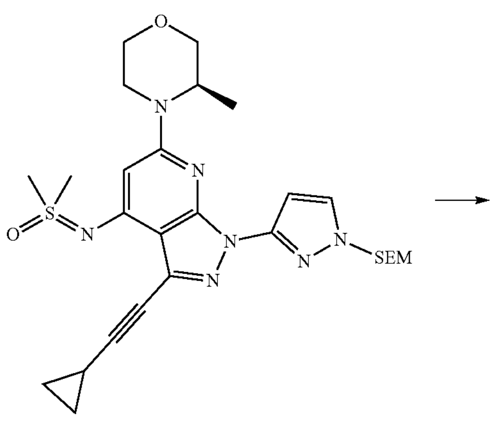
26-8

-continued

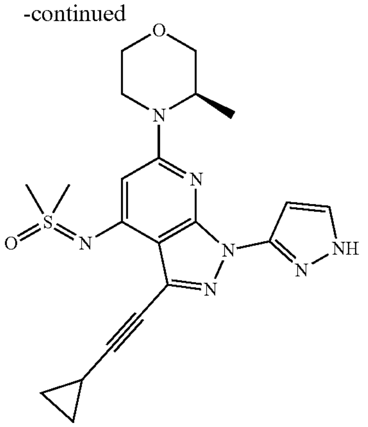

26

Step 1: Synthesis of Compound 26-1

Compound A1-4 (5.3 g) and tetrahydrofuran (100 mL) were mixed and cooled to 0° C., and an 85% solution of hydrazine hydrate (817 mg) was added dropwise. The mixture was left to react overnight at room temperature. The reaction solution was concentrated, and the crude product was separated and purified by column chromatography (petroleum ether:ethyl acetate=5:1) to give compound 26-1 (1.8 g).

MS (ESI, $[M-H]^-$) m/z: 261.83.

$^1$H NMR (500 MHz, DMSO-$d_6$) δ 14.05 (s, 1H), 8.03-7.99 (m, 1H), 7.53 (s, 1H).

Step 2: Synthesis of Compound 26-2

Compound 26-1 (1.8 g) and N,N-dimethylformamide (30 mL) were mixed and cooled to 0° C., and N-bromosuccinimide (1.34 g) was added portionwise. The reaction solution was warmed to room temperature and stirred overnight. Ethyl acetate (100 mL) was added to the reaction solution. The organic phase was washed with water and saturated brine successively and concentrated. The resulting crude product was separated and purified by column chromatography (petroleum ether:ethyl acetate=5:1) to give compound 26-2 (1.72 g).

$^1$H NMR (500 MHz, DMSO-$d_6$) δ 14.35 (s, 1H), 7.67 (s, 1H).

Step 3: Synthesis of Compound 26-3

Compound 26-2 (1.7 g), (R)-3-methylmorpholine (2.51 g) and dimethyl sulfoxide (10 mL) were mixed, heated to 120° C. and left to react for 2 h. Ethyl acetate (100 mL) was added to the reaction solution. The organic phase was washed with water and saturated brine successively and dried over anhydrous sodium sulfate. After filtration and concentration, the crude product was separated and purified by column chromatography (petroleum ether:ethyl acetate=1:1) to give compound 26-3 (1.75 g).

MS (ESI, $[M+H]^+$) m/z: 422.94.

$^1$H NMR (500 MHz, DMSO-d) δ 13.37 (s, 1H), 7.29 (s, 1H), 4.48-4.35 (m, 1H), 3.99-3.87 (m, 2H), 3.71 (d, J=11.4 Hz, 1H), 3.61 (dd, J=11.4, 2.9 Hz, 1H), 3.46 (td, J=11.7, 2.9 Hz, 1H), 3.15 (td, J=12.8, 3.7 Hz, 1H), 1.17 (d, J=6.7 Hz, 3H).

Step 4: Synthesis of Compound 26-4

Compound 26-3 (1.7 g) and N,N-dimethylformamide (20 mL) were mixed and cooled to 0° C., and 60% sodium hydride (193 mg) was added portionwise. The mixture was left to react at 0° C. for 0.5 h. 2-(Trimethylsilyl)ethoxymethyl chloride (1.0 g) was added to the reaction solution, and the mixture was left to react at 0° C. for 0.5 h. Ethyl acetate (100 mL) and saturated ammonium chloride (50 mL) were added to the reaction solution. The organic phase was separated, washed with water and saturated brine successively and concentrated. The resulting crude product was separated and purified by column chromatography (petroleum ether:ethyl acetate=5:1) to give compound 26-4 (1.85 g).

MS (ESI, $[M+H]^+$) m/z: 552.90.

$^1$H NMR (500 MHz, DMSO-$d_6$) δ 7.34 (s, 1H), 5.52 (s, 2H), 4.53-4.43 (m, 1H), 4.06 (d, J=12.4 Hz, 1H), 3.94 (dd, J=11.4, 3.3 Hz, 1H), 3.73 (d, J=11.4 Hz, 1H), 3.63-3.52 (m, 3H), 3.45 (td, J=11.6, 2.6 Hz, 1H), 3.16 (td, J=13.0, 3.7 Hz, 1H), 1.18 (d, J=6.7 Hz, 3H), 0.86-0.78 (m, 2H), −0.10 (s, 9H).

Step 5: Synthesis of Compound 26-5

Compound 26-4 (1.8 g), dimethylsulfoximine (333 mg), tris(dibenzylideneacetone)dipalladium (298 mg), 4,5-bisdiphenylphosphino-9,9-dimethylxanthene (376 mg), cesium carbonate (2.12 g) and 1,4-dioxane (20 mL) were mixed and left to react at 80° C. for 1 h under nitrogen atmosphere. The reaction solution was filtered, and the filtrate was concentrated. The crude product was then separated and purified by column chromatography (petroleum ether:ethyl acetate=1:1) to give compound 26-5 (1.42 g).

MS (ESI, $[M+H]^+$) m/z: 518.13.

$^1$H NMR (500 MHz, DMSO-$d_6$) δ 6.10 (s, 1H), 5.46 (s, 2H), 4.36-4.28 (m, 1H), 3.97-3.89 (m, 2H), 3.73 (d, J=11.3 Hz, 1H), 3.61 (dd, J=11.5, 2.8 Hz, 1H), 3.56 (dq, J=9.7, 3.0 Hz, 2H), 3.46 (td, J=11.8, 2.9 Hz, 1H), 3.39 (s, 6H), 3.10 (td, J=12.8, 3.7 Hz, 1H), 1.15 (d, J=6.7 Hz, 3H), 0.88-0.78 (m, 2H), −0.09 (s, 9H).

Step 6: Synthesis of Compound 26-6

Compound 26-5 (500 mg), cyclopropylacetylene (637 mg), copper(I) iodide (55 mg), bis(triphenylphosphine)palladium(II) dichloride (203 mg), triethylamine (293 mg), cesium carbonate (2.12 g) and acetonitrile (10 mL) were mixed and left to react overnight at 85° C. under nitrogen atmosphere. The reaction solution was filtered, and the filtrate was concentrated. The crude product was then separated and purified by column chromatography (petroleum ether:ethyl acetate=1:1) to give compound 26-6 (298 mg).

MS (ESI, $[M+H]^+$) m/z: 504.30.

$^1$H NMR (500 MHz, DMSO-$d_6$) δ 6.07 (s, 1H), 5.45 (s, 2H), 4.36-4.26 (m, 1H), 3.98-3.86 (m, 2H), 3.73 (d, J=11.2 Hz, 1H), 3.61 (dd, J=11.3, 2.7 Hz, 1H), 3.54 (dq, J=9.8, 3.0 Hz, 2H), 3.49-3.42 (m, 1H), 3.38 (s, 6H), 3.09 (td, J=12.8, 3.7 Hz, 1H), 1.57 (tt, J=8.3, 5.0 Hz, 1H), 1.14 (d, J=6.6 Hz, 3H), 0.92-0.86 (m, 2H), 0.86-0.79 (m, 2H), 0.79-0.74 (m, 2H), −0.10 (s, 9H).

Step 7: Synthesis of Compound 26-7

Compound 26-6 (290 mg) was dissolved in dichloromethane (5 mL). The solution was cooled to 0° C., and triethylsilane (1.46 g) and trifluoroacetic acid (15 mL) were added.

The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (petroleum ether:ethyl acetate=1:1) to give compound 26-7 (191 mg).

MS (ESI, $[M+H]^+$) m/z: 374.20.

$^1$H NMR (500 MHz, DMSO-$d_6$) δ 12.66 (s, 1H), 6.04 (s, 1H), 4.25 (d, J=4.7 Hz, 1H), 3.92 (dd, J=11.2, 3.2 Hz, 1H), 3.80 (d, J=11.2 Hz, 1H), 3.71 (d, J=11.3 Hz, 1H), 3.62 (dd, J=11.3, 2.7 Hz, 1H), 3.46 (td, J=11.7, 2.9 Hz, 1H), 3.36 (s, 6H), 3.08 (td, J=12.7, 3.8 Hz, 1H), 1.56 (tt, J=8.3, 5.0 Hz, 1H), 1.13 (d, J=6.6 Hz, 3H), 0.90-0.84 (m, 2H), 0.78-0.72 (m, 2H).

Step 8: Synthesis of Compound 26-8

Compound 26-7 (150 mg), 3-iodo-1-((2-(trimethylsilyl)ethoxy)methyl)-1H-pyrazole (260 mg), copper(I) iodide (115 mg), (1R,2R)-cyclohexane-1,2-diamine (138 mg), cesium carbonate (393 mg) and N-methylpyrrolidinone (5 mL) were mixed, microwaved to 140° C. and left to react for 0.5 h. Ethyl acetate (100 mL) was added to the reaction solution. The organic phase was washed with 1 M ammonium hydroxide, water and saturated brine successively, and dried over anhydrous sodium sulfate. The filtrate was concentrated, and the crude product was then separated and purified by column chromatography (petroleum ether:ethyl acetate=1:1) to give compound 26-8 (113 mg).

MS (ESI, $[M+H]^+$) m/z: 570.40.

$^1$H NMR (500 MHz, DMSO-$d_6$) δ 7.98 (d, J=2.3 Hz, 1H), 6.89 (d, J=2.3 Hz, 1H), 6.12 (s, 1H), 5.40 (s, 2H), 4.35-4.24 (m, 1H), 3.98-3.86 (m, 2H), 3.74 (d, J=11.3 Hz, 1H), 3.64 (dd, J=11.3, 2.6 Hz, 1H), 3.58 (t, J=8.0 Hz, 2H), 3.48 (td, J=11.8, 2.8 Hz, 1H), 3.41 (s, 6H), 3.12 (td, J=12.7, 3.7 Hz, 1H), 1.61 (tt, J=8.3, 5.0 Hz, 1H), 1.17 (d, J=6.7 Hz, 3H), 0.92 (td, J=6.6, 3.9 Hz, 2H), 0.85 (t, J=8.0 Hz, 2H), 0.82-0.78 (m, 2H), −0.04 (s, 9H).

Step 9: Synthesis of Compound 26

Compound 26-8 (100 mg) was dissolved in dichloromethane (1 mL). The solution was cooled to 0° C., and triethylsilane (408 mg) and trifluoroacetic acid (3 mL) were added. The mixture was left to react at room temperature for 1 h. Dichloromethane (30 mL) was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was purified by column chromatography (dichloromethane:methanol=19:1) to give compound 26 (48 mg).

HRMS: (ESI, $[M+H]^+$) m/z: 440.1872.

$^1$H NMR (500 MHz, DMSO-$d_6$) δ 12.78 (s, 1H), 7.80 (s, 1H), 6.77 (s, 1H), 6.12 (s, 1H), 4.35-4.26 (m, 1H), 3.95 (dd, J=11.2, 3.1 Hz, 1H), 3.90 (d, J=12.5 Hz, 1H), 3.74 (d, J=11.3 Hz, 1H), 3.63 (dd, J=11.3, 2.7 Hz, 1H), 3.48 (td, J=11.7, 2.8 Hz, 1H), 3.41 (s, 6H), 3.12 (td, J=12.7, 3.5 Hz, 1H), 1.64-1.58 (m, 1H), 1.17 (d, J=6.7 Hz, 3H), 0.94-0.89 (m, 2H), 0.83-0.78 (m, 2H).

Example 27: Synthesis of Compound 27

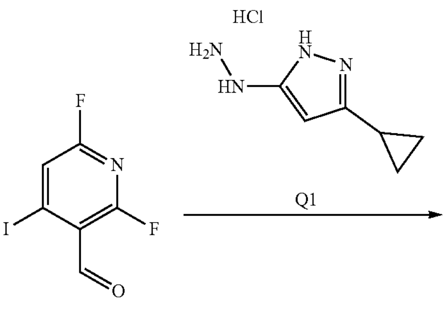

A1-4

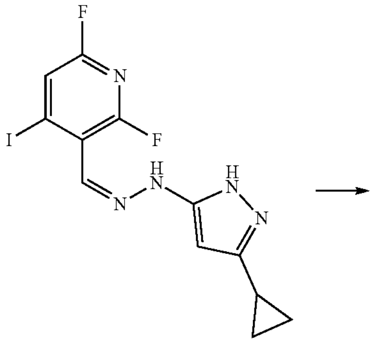

27-1

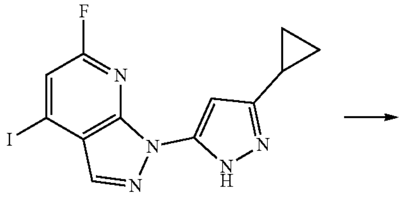

27-2

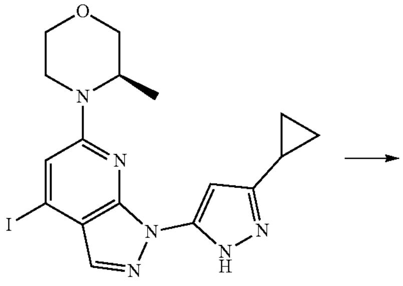

27-3

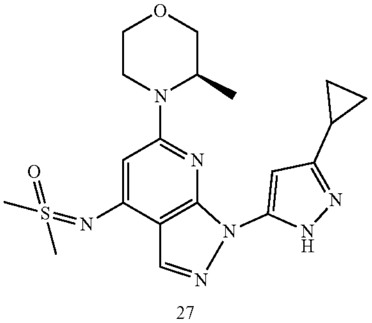

27

Step 1: Synthesis of Compound 27-1

Compound A1-4 (2 g), compound Q1 (5.19 g) and ethanol (30 mL) were mixed and left to react at room temperature for 1 h. The reaction solution was concentrated, and the residue was dissolved in ethyl acetate. The solution was washed with saturated sodium bicarbonate, water and saturated brine successively, dried over anhydrous sodium sulfate, filtered, and concentrated to give compound 27-1 (2.6 g).

MS: (ESI, $[M+H]^+$) m/z: 390.24.

$^1$HNMR (500 MHz, DMSO-$d_6$) δ 11.73 (s, 1H), 10.75 (s, 1H), 7.90 (s, 1H), 7.80 (s, 1H), 5.65 (d, J=9.0 Hz, 1H), 1.83 (dq, J=8.5, 5.1 Hz, 1H), 1.01-0.85 (m, 2H), 0.74-0.61 (m, 2H).

Step 2: Synthesis of Compound 27-2

Compound 27-1 (2.6 g) and N-methylpyrrolidone (20 mL) were mixed, microwaved to 200° C. and left to react for 20 min. Water was added to the reaction solution, and a solid precipitated. The solid was collected by filtration, washed and dried to give compound 27-2 (1.6 g).

MS (ESI, $[M+H]^+$) m/z: 370.14.

$^1$HNMR (500 MHz, DMSO-$d_6$) δ 12.82 (s, 1H), 8.24 (s, 1H), 7.67 (s, 1H), 6.34 (s, 1H), 2.01 (dt, J=8.4, 4.6 Hz, 1H), 1.06-0.96 (m, 2H), 0.86-0.70 (m, 2H).

Step 3: Synthesis of Compound 27-3

Compound 27-2 (500 mg), (R)-3-methylmorpholine (274 mg) and dimethyl sulfoxide (5 mL) were mixed, heated to 120° C. and left to react for 1 h. Water was added to the reaction solution, and a solid precipitated. The solid was collected by filtration, washed and dried to give compound 27-3 (260 mg).

MS (ESI, $[M+H]^+$) m/z: 451.28.

$^1$HNMR (500 MHz, DMSO-$d_6$) δ 12.59 (s, 1H), 7.80 (s, 1H), 7.26 (s, 1H), 6.40 (s, 1H), 4.43 (d, J=5.0 Hz, 1H), 4.03 (d, J=12.9 Hz, 1H), 3.95 (dd, J=11.3, 3.0 Hz, 1H), 3.74 (d, J=11.4 Hz, 1H), 3.63 (dd, J=11.4, 2.7 Hz, 1H), 3.48 (td, J=11.8, 2.7 Hz, 1H), 3.16 (td, J=12.9, 3.4 Hz, 1H), 2.03-1.91 (m, 1H), 1.19 (d, J=6.6 Hz, 3H), 0.98 (d, J=6.5 Hz, 2H), 0.76 (d, J=3.3 Hz, 2H).

Step 4: Synthesis of Compound 27

Compound 27-3 (260 mg), dimethylsulfoximine (81 mg), tris(dibenzylideneacetone)dipalladium (26 mg), 4,5-bisdiphenylphosphino-9,9-dimethylxanthene (33 mg), cesium carbonate (376 mg) and 1,4-dioxane (7 mL) were mixed and left to react at 80° C. for 1 h under nitrogen atmosphere. The reaction solution was filtered, and the filtrate was concentrated. The crude product was then separated and purified by column chromatography (petroleum ether:ethyl acetate=1:1) to give compound 27 (80 mg).

HRMS: (ESI, $[M+H]^+$) m/z: 416.1896.

$^1$HNMR (500 MHz, DMSO-$d_6$) δ 12.45 (s, 1H), 7.86 (s, 1H), 6.42 (s, 1H), 6.16 (s, 1H), 4.30 (d, J=5.3 Hz, 1H), 3.99-3.86 (m, 2H), 3.75 (d, J=11.3 Hz, 1H), 3.64 (dd, J=11.3, 2.8 Hz, 1H), 3.49 (td, J=11.8, 2.9 Hz, 1H), 3.41 (s, 6H), 3.12 (td, J=12.7, 3.5 Hz, 1H), 2.00-1.90 (m, 1H), 1.17 (d, J=6.7 Hz, 3H), 0.96 (d, J=5.8 Hz, 2H), 0.74 (d, J=3.4 Hz, 2H).

Example 28: Synthesis of Compound 28

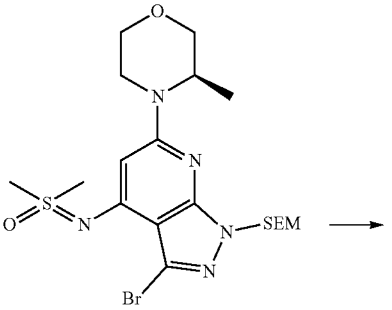

26-5

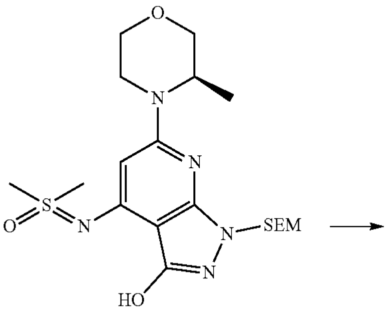

28-1

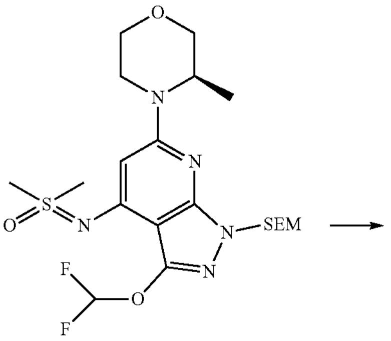

28-2

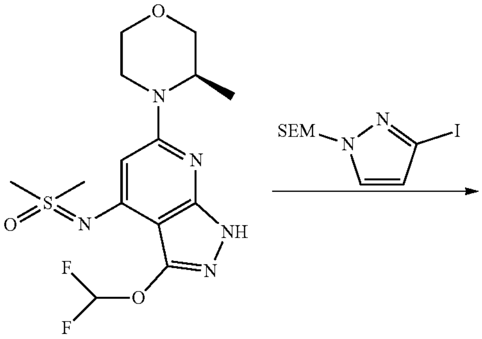

28-3

-continued

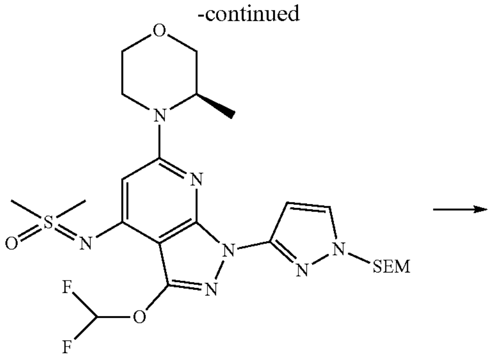

28-4

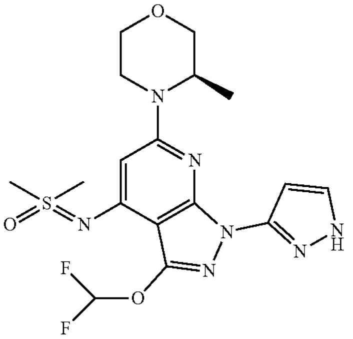

28

Step 1: Synthesis of Compound 28-1

Compound 26-5 (0.5 g), (N1,N2-bis(4-hydroxy-2,6-dimethylphenyl)oxamide (63 mg), copper acetylacetonate (50 mg), lithium hydroxide (69 mg), dimethyl sulfoxide (10 mL) and water (3 mL) were mixed and, under nitrogen atmosphere, microwaved to 140° C. and left to react for 0.5 h. Ethyl acetate was added to the reaction solution. The organic phase was washed with water and saturated brine successively, and dried over anhydrous sodium sulfate. The filtrate was concentrated, and the crude product was then separated and purified by column chromatography (petroleum ether: ethyl acetate=1:1) to give compound 28-1 (400 mg).

MS (ESI, $[M+H]^+$) m/z: 456.30.

Step 2: Synthesis of Compound 28-2

Compound 28-1 (0.4 g), potassium hydroxide (1 g), acetonitrile (10 mL) and water (10 mL) were mixed and cooled to −20° C., and diethyl bromofluoromethylphosphonate (0.7 g) was added portionwise under nitrogen atmosphere. The reaction solution was stirred at −20° C. for 30 min. Ethyl acetate was added to the reaction solution. The organic phase was washed with water and saturated brine successively and concentrated. The resulting crude product was separated and purified by column chromatography (petroleum ether:ethyl acetate=3:1) to give compound 28-2 (330 mg).

MS (ESI, $[M+H]^+$) m/z: 506.26.

Step 3: Synthesis of Compound 28-3

Compound 28-2 (330 mg) was dissolved in dichloromethane (5 mL). The solution was cooled to 0° C., and triethylsilane (0.8 g) and trifluoroacetic acid (9 mL) were added.

The mixture was left to react at room temperature for 1 h. Dichloromethane was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (petroleum ether:ethyl acetate=1:1) to give compound 28-3 (220 mg).

MS (ESI, $[M+H]^+$) m/z: 376.05.

Step 4: Synthesis of Compound 28-4

Compound 28-3 (220 mg), 3-iodo-1-((2-(trimethylsilyl) ethoxy)methyl)-1H-pyrazole (385 mg), copper(I) iodide (165 mg), (1R,2R)-cyclohexane-1,2-diamine (198 mg), cesium carbonate (572 mg) and N-methylpyrrolidinone (11 mL) were mixed, microwaved to 140° C. and left to react for 0.5 h. Ethyl acetate was added to the reaction solution. The organic phase was washed with 1 M ammonium hydroxide, water and saturated brine successively, and dried over anhydrous sodium sulfate. The filtrate was concentrated, and the crude product was then separated and purified by column chromatography (petroleum ether:ethyl acetate=1:1) to give compound 28-4 (200 mg).

MS (ESI, $[M+H]^+$) m/z: 572.27.

Step 5: Synthesis of Compound 28

Compound 28-4 (200 mg) was dissolved in dichloromethane (3 mL). The solution was cooled to 0° C., and triethylsilane (405 mg) and trifluoroacetic acid (5 mL) were added. The mixture was left to react at room temperature for 1 h. Dichloromethane (40 mL) was added to dilute the reaction solution, and the pH was adjusted to 8 with a saturated solution of sodium bicarbonate. The organic phase was washed with water and saturated brine successively and dried over anhydrous sodium sulfate. After filtration and concentration, the crude product was separated and purified by column chromatography (dichloromethane:methanol=18:1) to give compound 28 (120 mg).

HRMS: (ESI, $[M+H]^+$) m/z: 442.1469.

$^1$HNMR (500 MHz, DMSO-$d_6$) δ 12.74 (s, 1H), 7.80 (s, 1H), 7.49 (m, 1H), 6.75 (s, 1H), 6.15 (s, 1H), 4.39-4.27 (m, 1H), 4.01-3.87 (m, 2H), 3.75 (d, J=11.3 Hz, 1H), 3.64 (dd, J=11.4, 2.8 Hz, 1H), 3.49 (dd, J=11.8, 2.9 Hz, 1H), 3.44 (s, 6H), 3.14 (td, J=12.7, 3.7 Hz, 1H), 1.18 (d, J=6.7 Hz, 3H).

Test Example 1: Screening for In Vitro Inhibitory Activity Against ATR Kinase

A 50 ng/μL ATR stock solution was diluted with a kinase buffer (50 mM HEPES, 10 mM $MgCl_2$, 2 mM DTT, 1 mM EGTA, 0.01% Tween 20), and 6 μL of 1.67×, 0.0835 ng/μL working solution was added to each well (final concentration: 0.05 ng/μL). Different compounds dissolved in DMSO were added to wells using a nanoliter pipettor, such that the final concentrations of the compounds were 1000 nM-0.24 nM and the concentrations in positive wells were 100 nM-0.024 nM (4-fold gradient, 7 concentrations in total). Meanwhile, a blank control well (containing no enzyme) and a negative control well (containing enzyme, with the vehicle DMSO added) were set. After the enzyme had reacted with the compound or vehicle for 30 min, a 5×, 50 μM ATP (final concentration: 10 μM) prepared with the kinase buffer and a 5×, 0.5 μM substrate (final concentration: 0.1 μM, U Light-poly GT) were 1:1 mixed, and the mixture was added to wells at 4 μL/well. After the plate was sealed with a sealing film and the plate was incubated at room temperature for 2 h, 5 μL of 4×, 40 mM EDTA (final concentration: 10 mM) was added to each well. After 5 min of incubation at room temperature, 5 μL of a 4×, 8 nM assay reagent (final concentration: 2 nM, Ep-anti-phospho-tyrosine antibody) was added to each well. The plate was incubated at room temperature for 1 h. Plate reading was performed on a PE instrument (excitation: 320 or 340 nm; emission: 665 nm), and four-parameter fitting and $IC_{50}$ calculations were performed. The results are shown in Table 1, where A represents $IC_{50}$<50 nM.

TABLE 1

Inhibitory activity of compounds against ATR kinase

| Compound | $IC_{50}$ (nM) |
|---|---|
| 1 | A |
| 3 | A |
| 4 | A |
| 6 | A |
| 10-A | A |
| 10-B | A |
| 13 | A |
| 14-A | A |
| 15-A | A |
| 16-A | A |
| 17 | A |
| 19-A | A |
| 20 | A |
| 23 | A |
| 24 | A |
| 25 | A |

Test Example 2: Assay for Inhibitory Activity on CHK1 Phosphorylation in TMD-8 Cells TMD-8 cells in a good growth state were collected into a centrifuge tube, adjusted to a cell density of $1\times10^7$ cells/mL, and inoculated onto a 384-well plate (4 μL/well). Compounds were added using a nanoliter pipettor such that the final concentrations of the compounds were 1000 nM-0.24 nM (the addition was performed in duplicate). Meanwhile, a control was set. After the plate was incubated in a cell incubator for 0.5 h, 10 mM HU (4 μL/well) was added. After 2 h of incubation at room temperature, an assay was performed using a p-CHK1 (Ser345) assay kit (manufacturer: perkinelmer) and the Envision microplate reader AlphaLISA program. A four-parameter analysis was performed, a dose-response curve was fit, and $IC_{50}$ was calculated. The results show that the $IC_{50}$ for the inhibitory activity of the example compounds against CHK1 phosphorylation in TMD-8 cells <50 nM.

Test Example 3: Assay for Inhibitory Activity on TMD-8 Cell Proliferation

TMD-8 cells in a good growth state were collected into a centrifuge tube, adjusted to a cell density of $4\times10^4$ cells/mL, and inoculated onto a 96-well plate (100 μL/well), and the plate was incubated overnight in a cell incubator. Compounds were added using a nanoliter pipettor such that the final concentrations of the compounds were 10,000 nM-4.57 nM (the addition was performed in duplicate). Meanwhile, a control was set. After another 72 h of incubation in the cell incubator, the assay reagent CCK-8 (manufacturer: Dojindo Laboratories; 10 μL/well) was added. After 4 h of incubation in the cell incubator, absorbance was measured at 450 nm on an Envision microplate reader. A four-parameter analysis was performed, a dose-response curve was fit, and $IC_{50}$ was calculated. The results are shown in Table 2, where A represents $IC_{50}$≤200 nM.

TABLE 2

Inhibitory activity of compounds on TMD-8 cell proliferation

| Compound | $IC_{50}$ (nM) |
|---|---|
| 1 | A |
| 2 | A |
| 3 | A |
| 4 | A |
| 5 | A |
| 15-A | A |
| 15-B | A |
| 17 | A |
| 19-A | A |
| 19-B | A |
| 20 | A |
| 21 | A |
| 22 | A |
| 23 | A |
| 24 | A |
| 25 | A |
| 26 | A |

Test Example 4: Assay for In Vitro Liver Microsomal Stability

A 200-μL final incubation system contained 20 μL of liver microsomes (protein concentration: 5 mg/mL), 20 μL of NADPH+$MgCl_2$, 2 μL of a substrate, and 158 μL of PBS buffer. The proportion of the organic solvent was 1%. The assay was performed in duplicate (0.2 mL each) for each species. A 180-μL mixture of substrate and enzyme was prepared in each tube. After the mixture and NADPH were pre-incubated at 37° C. for 5 min, 20 μL of NADPH+$MgCl_2$ was added and mixed. 50-μL samples were taken at 0, 15 and 60 min, and the reactions were stopped using ice-cold acetonitrile containing an internal standard.

50-μL incubated samples were taken, and 300 μL of internal standard-containing acetonitrile was added for precipitation. After 5 min of vortexing and shaking, centrifugation (13,000 rpm, 20° C.) was performed for 10 min. 80 μL of the supernatant was added to a 96-well plate and diluted with 80 μL of ultrapure water, and 1 μL of the dilution was injected for LC-MS/MS analysis. The results are shown in Table 3.

TABLE 3

In vitro liver microsomal stability

| Compound | Human liver microsome (Residual % at 60 min) |
|---|---|
| 1 | 102.05 |
| 2 | 85.89 |
| 3 | 106.47 |
| 4 | 96.49 |
| 6 | 94.62 |
| 10-A | 95.39 |
| 10-B | 94.14 |
| 13 | 108.36 |

Test Example 5: Pharmacokinetic Evaluation of Compounds in Mice

ICR mice, weighing 18-22 g, were randomized into 4 groups of 9 after 3-5 days of acclimatization, and were administered intragastrically (IG) a test compound at a dose of 10 mg/kg and intravenously (IV) a test compound at a dose of 1 mg/kg.

The test animals (ICR mice) were fasted for 12 h before the administration and given food 4 h after the administration, and they were given ad libitum access to water before, during and after the experiment.

Orbital blood samples of about 0.1 mL were collected at 15 min, 30 min, 1 h, 2 h, 3 h, 4 h, 6 h, 8 h, 10 h and 24 h after the intragastric administration. Orbital blood samples of about 0.1 mL were collected at 5 min, 10 min, 30 min, 1 h, 2 h, 4 h, 6 h, 8 h, 10 h and 24 h after the intravenous administration. The blood sample collection was performed at 3-4 time points for each mouse, 3 mice/per time point. The collected whole blood was placed in EDTA-K2-containing centrifuge tubes and stored at 4° C., and, within 1 h, was centrifuged at 4° C. at 4000 rpm for 10 min to separate plasma. All plasma samples were collected and immediately stored at −20° C. for testing. 30 μL of a plasma sample to be tested and a standard-curve sample were collected, and 300 μL of an acetonitrile solution containing an internal standard (20 ng/mL diazepam) was added and well mixed by 5 min of shaking. The mixture was centrifuged at 13,000 rpm for 10 min, and 80 L of the supernatant was collected and diluted with 80 μL of ultrapure water. After well mixing, 2 μL of the dilution was collected for liquid chromatography-mass spectrometry analysis, and pharmacokinetic parameters were calculated. The results are shown in Table 4.

TABLE 4

The results of the pharmacokinetic evaluation of compounds in mice

| Compound | IG half-life t½ (h) | Peak concentration $C_{max}$ (ng/mL) | Area under plasma concentration-time curve $AUC_{0\text{-}last}$ (h · ng/ml) | Tissue distribution Vd (L/kg) | Absolute bioavailability F (%) |
|---|---|---|---|---|---|
| 10-A | 1.3 | 4888 | 13943 | 0.68 | 66% |
| 10-B | 3.3 | 4633 | 10311 | 1.38 | 81% |
| 19-A | 1.16 | 2948 | 5403 | 4.58 | 88% |
| 19-B | 2.65 | 2210 | 4445 | 8.46 | 85% |
| 20 | 1.93 | 6518 | 14581 | 1.04 | 74% |

The invention claimed is:

1. A compound of formula (I), a stereoisomer thereof or a pharmaceutically acceptable salt thereof, (I)

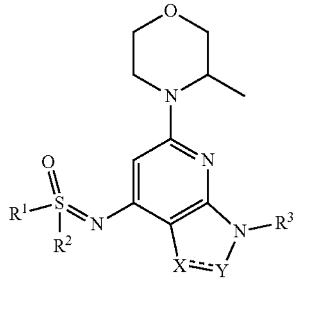

wherein

------ is a double bond, X is selected from $CR^a$, and Y is selected from N; or, ------ is a single bond, X is selected from C═O, and Y is selected from $NR^b$;

$R^a$ is selected from the group consisting of hydrogen, hydroxy, cyano, halogen, $C_{1-6}$ alkyl, $C_{1-6}$ alkoxy, $C_{1-6}$ alkylamino, $C_{3-10}$ cycloalkyl, 3-10 membered heterocycloalkyl and $C_{3-10}$ cycloalkyl-$C_{2-6}$ alkynyl, wherein the $C_{1-6}$ alkyl, $C_{1-6}$ alkoxy, $C_{1-6}$ alkylamino, $C_{3-10}$ cycloalkyl, 3-10 membered heterocycloalkyl and $C_{3-10}$ cycloalkyl-$C_{2-6}$ alkynyl are optionally substituted with one or more halogen, hydroxy or cyano substituents;

$R^b$ is selected from the group consisting of hydrogen and $C_{1-6}$ alkyl;

$R^1$ and $R^2$ are each independently selected from the group consisting of $C_{1-10}$ alkyl, $C_{3-10}$ cycloalkyl, 3-10 membered heterocycloalkyl, $C_{6-10}$ membered aryl and 5-10 membered heteroaryl, wherein the $C_{3-10}$ cycloalkyl, 3-10 membered heterocycloalkyl, $C_{6-10}$ membered aryl and 5-10 membered heteroaryl are optionally substituted with one or more $R^c$;

or $R^1$ and $R^2$, together with the sulfur atom to which they are attached, form 3-10 membered heterocyclyl, and the 3-10 membered heterocyclyl is optionally substituted with one or more $R^d$;

$R^c$ and $R^d$ are each independently selected from the group consisting of halogen, hydroxy, amino, $C_{1-6}$ alkyl, $C_{1-6}$ alkoxy, $C_{1-6}$ alkyl-C(O)—, $C_{1-6}$ alkyl-$S(O)_2$—, $C_{3-10}$ cycloalkyl, 3-10 membered heterocycloalkyl, $C_{6-10}$ membered aryl and 5-10 membered heteroaryl;

$R^3$ is selected from 5-10 membered heteroaryl optionally substituted with one or more $R^e$;

$R^e$ is selected from the group consisting of hydroxy, amino, halogen, $C_{1-6}$ alkyl, $C_{1-3}$ haloalkyl, $C_{3-6}$ cycloalkyl and 3-6 membered heterocycloalkyl.

2. The compound according to claim 1, wherein $R^a$ is selected from the group consisting of hydrogen, halogen, $C_{1-6}$ alkyl, $C_{1-6}$ alkoxy, $C_{3-10}$ cycloalkyl and $C_{3-10}$ cycloalkyl-$C_{2-6}$ alkynyl, wherein the $C_{1-6}$ alkyl, $C_{1-6}$ alkoxy, $C_{3-10}$ cycloalkyl and $C_{3-10}$ cycloalkyl-$C_{2-6}$ alkynyl are optionally substituted with one or more halogens;

or $R^a$ is selected from the group consisting of hydrogen, hydroxy, halogen and $C_{1-6}$ alkyl, wherein the $C_{1-6}$ alkyl is optionally substituted with one or more halogens;

or $R^a$ is selected from the group consisting of hydrogen, hydroxy, halogen and $C_{1-3}$ alkyl, wherein the $C_{1-3}$ alkyl is optionally substituted with one or more halogens;

or $R^a$ is selected from the group consisting of hydrogen, halogen, $C_{1-4}$ alkyl, $C_{1-4}$ alkoxy, $C_{3-6}$ cycloalkyl and $C_{3-6}$ cycloalkyl-$C_{2-4}$ alkynyl, wherein the $C_{1-4}$ alkyl, $C_{1-4}$ alkoxy, $C_{3-6}$ cycloalkyl and $C_{3-6}$ cycloalkyl-$C_{2-4}$ alkynyl are optionally substituted with one or more halogens;

or $R^a$ is selected from the group consisting of hydrogen, bromine, methyl, n-propyl, isobutyl, tert-butyl, methoxy, cyclopropyl and cyclopropylethynyl, wherein the methyl, n-propyl, isobutyl, tert-butyl, methoxy, cyclopropyl and cyclopropylethynyl are optionally substituted with one or more halogens;

or $R^a$ is selected from the group consisting of hydrogen, bromine, methyl, trifluoromethyl, 3,3,3-trifluoropropyl, isobutyl, tert-butyl, difluoromethoxy, cyclopropyl and cyclopropylethynyl;

or $R^a$ is selected from the group consisting of hydrogen and bromine.

3. The compound according to claim 1, wherein $R^b$ is selected from the group consisting of hydrogen and $C_{1-3}$ alkyl;

or $R^b$ is selected from hydrogen.

4. The compound according to claim 1, wherein ------ is a double bond, X is selected from the group consisting of CH and CBr, and Y is selected from N.

5. The compound according to claim 1, wherein ------ is a single bond, X is selected from C═O, and Y is selected from NH.

6. The compound according to claim 1, wherein $R^1$ and $R^2$ are each independently selected from the group consisting of $C_{1-6}$ alkyl, $C_{3-8}$ cycloalkyl, 3-8 membered heterocycloalkyl, phenyl and 5-6 membered heteroaryl, wherein the $C_{3-8}$ cycloalkyl, 3-8 membered heterocycloalkyl, phenyl and 5-6 membered heteroaryl are optionally substituted with one or more $R^c$;

or $R^1$ and $R^2$ are each independently selected from the group consisting of $C_{1-4}$ alkyl, $C_{3-6}$ cycloalkyl, 3-6 membered heterocycloalkyl, phenyl and 5-6 membered heteroaryl, wherein the $C_{3-6}$ cycloalkyl, 3-6 membered heterocycloalkyl, phenyl and 5-6 membered heteroaryl are optionally substituted with one or more $R^c$;

or $R^1$ and $R^2$ are each independently selected from the group consisting of methyl, ethyl, n-propyl, isopropyl, n-butyl, isobutyl, tert-butyl, cyclopropyl, cyclobutyl, cyclopentyl, cyclohexyl, phenyl, pyrrolyl, thienyl, pyridinyl, pyrimidinyl and furanyl, wherein the cyclopropyl, cyclopentyl, cyclohexyl, phenyl, pyrrolyl, thienyl, pyridinyl, pyrimidinyl or furanyl is optionally substituted with one or more $R^c$;

optionally, $R^1$ and $R^2$ are each independently selected from the group consisting of $C_{1-3}$ alkyl, $C_{3-4}$ cycloalkyl, phenyl and 5-6 membered heteroaryl, wherein the $C_{3-4}$ cycloalkyl, phenyl and 5-6 membered heteroaryl are optionally substituted with one or more $R^c$;

or $R^1$ and $R^2$ are each independently selected from the group consisting of methyl, ethyl, tert-butyl, cyclopropyl, cyclopentyl, cyclohexyl, phenyl and pyridinyl, wherein the cyclopropyl, cyclopentyl, cyclohexyl, phenyl and pyridinyl are optionally substituted with one or more $R^c$;

or $R^1$ and $R^2$ are each independently selected from the group consisting of methyl, ethyl, cyclopropyl, phenyl and pyridinyl.

7. The compound according to claim 1, wherein $R^c$ and $R^d$ are each independently selected from the group consisting of halogen, hydroxy, amino, $C_{1-4}$ alkyl, $C_{1-4}$ alkoxy, $C_{1-4}$ alkyl-C(O)—, $C_{1-4}$ alkyl-$S(O)_2$—, $C_{3-8}$ cycloalkyl, 3-8 membered heterocycloalkyl, $C_{6-8}$ membered aryl and 5-8 membered heteroaryl;

or $R^c$ and $R^d$ are each independently selected from the group consisting of halogen, hydroxy, amino, $C_{1-3}$ alkyl, $C_{1-3}$ alkoxy, $C_{1-3}$ alkyl-C(O)—, $C_{1-3}$ alkyl-$S(O)_2$ —, $C_{3-6}$ cycloalkyl, 3-6 membered heterocycloalkyl, phenyl and 5-6 membered heteroaryl;

or $R^c$ and $R^d$ are each independently selected from the group consisting of fluorine, chlorine, bromine, hydroxy, amino, methyl, ethyl, n-propyl, isopropyl, methoxy, ethoxy, n-propoxy, isopropoxy, $CH_3C(O)$—, $CH_3CH_2C(O)$—, $CH_3CH_2CH_2C(O)$—, $(CH_3)_2CH$ (O)—, $CH_3S(O)_2$—, $CH_3CH_2S(O)_2$—, $CH_3CH_2CH_2S$ $(O)_2$—, $(CH_3)_2CHS(O)_2$—, cyclopropyl, cyclopentyl, cyclohexyl, tetrahydrofuranyl, tetrahydropyrrolyl, piperazinyl, piperidinyl, phenyl, furanyl, pyrrolyl, thienyl, pyridinyl and pyrimidinyl;

optionally, $R^c$ and $R^d$ are each independently selected from the group consisting of halogen, hydroxy, amino, $C_{1-4}$ alkyl and $C_{1-4}$ alkoxy;

or $R^c$ and $R^d$ are each independently selected from the group consisting of halogen, hydroxy, amino, $C_{1-3}$ alkyl and $C_{1-3}$ alkoxy;

or $R^c$ and $R^d$ are each independently selected from the group consisting of halogen and $C_{1-3}$ alkyl.

8. The compound according to claim 1, wherein $R^1$ and $R^2$, together with the sulfur atom to which they are attached, form 4-, 5-, 6-, 7-, 8-, 9- or 10-membered heterocycloalkyl, and the heterocycloalkyl is optionally substituted with one or more $R^d$;

or $R^1$ and $R^2$, together with the sulfur atom to which they are attached, form 4-6 membered mono heterocycloalkyl or 7-10 membered spiro heterocycloalkyl, and the mono heterocycloalkyl or spiro heterocycloalkyl is optionally substituted with one or more $R^d$;

or $R^1$ and $R^2$, together with the sulfur atom to which they are attached, form 4-, 5- or 6-membered mono heterocycloalkyl, or 7- or 9-membered spiro heterocycloalkyl, and the mono heterocycloalkyl or spiro heterocycloalkyl is optionally substituted with 1, 2 or 3 $R^d$;

or $R^1$ and $R^2$, together with the sulfur atom to which they are attached, form

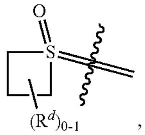 , 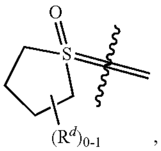 , 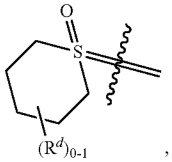 ,

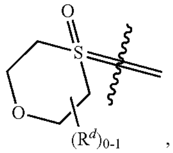 , 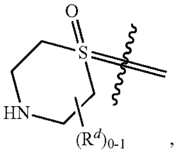 ,

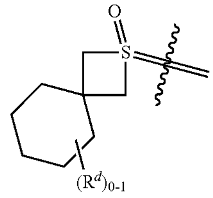 or 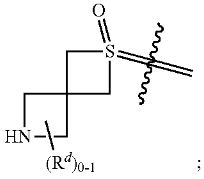 ;

or $R^1$ and $R^2$, together with the sulfur atom to which they are attached, form

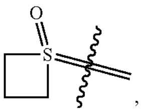 , 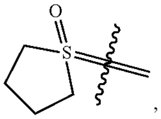 , 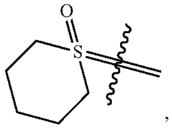 ,

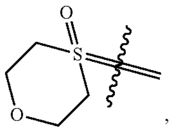 , 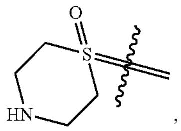 , 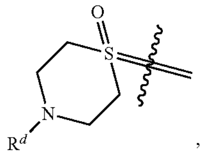 ,

-continued

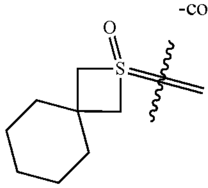

,

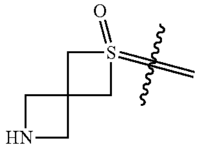

or

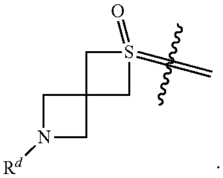

.

9. The compound according to claim 1, wherein $R^3$ is selected from 5-6 membered heteroaryl optionally substituted with one or more $R^e$;

or $R^3$ is selected from 5-membered heteroaryl optionally substituted with one or more $R^e$;

or $R^3$ is selected from 5-membered N-containing heteroaryl optionally substituted with one or more $R^e$;

or $R^3$ is selected from pyrazolyl optionally substituted with one or more $R^e$;

or $R^3$ is selected from pyrazolyl optionally substituted with one $R^e$;

or $R^3$ is selected from the group consisting of

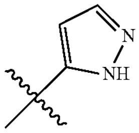

and

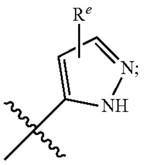

;

or $R^3$ is selected from the group consisting of

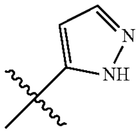

and

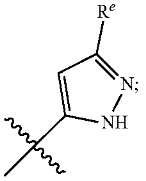

;

or $R^3$ is selected from the group consisting of

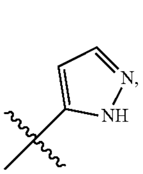

,

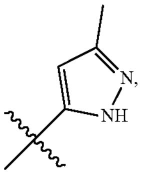

,

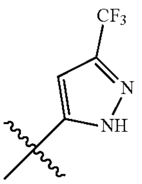

and

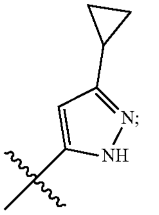

;

or $R^3$ is selected from

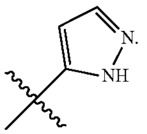 [SMILES: *c1ccn[nH]1]

.

10. The compound according to claim 1, wherein $R^e$ is selected from the group consisting of hydroxy, amino, halogen, $C_{1-3}$ alkyl, $C_{1-3}$ haloalkyl, $C_{3-6}$ cycloalkyl and 3-6 membered heterocycloalkyl;

or $R^e$ is selected from the group consisting of $C_{1-3}$ alkyl, $C_{1-3}$ haloalkyl and $C_{3-6}$ cycloalkyl;

or $R^e$ is selected from the group consisting of methyl, trifluoromethyl and cyclopropyl.

11. The compound of formula (I), the stereoisomer thereof or the pharmaceutically acceptable salt thereof according to claim 1, being selected from a compound of formula (II) or formula (III), a stereoisomer thereof or a pharmaceutically acceptable salt thereof:

(II)

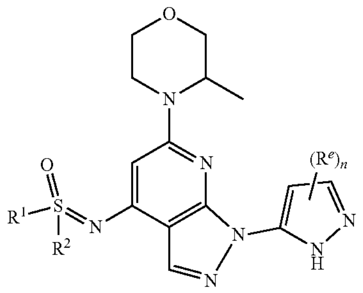

(III)

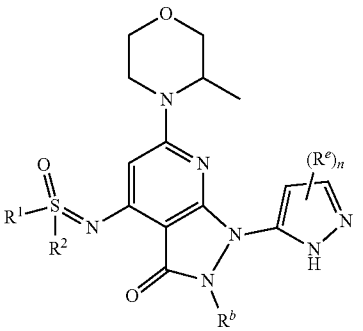

wherein $R^1$, $R^2$, $R^b$ and $R^e$ are as defined in claim 1;

n is selected from the group consisting of 0, 1 and 2.

12. The compound of formula (I), the stereoisomer thereof or the pharmaceutically acceptable salt thereof according to claim 1, being selected from the group consisting of a compound of formula (I-a), a compound of formula (I-b), a compound of formula (II-a), a compound of formula (II-b), a compound of formula (III-a), a compound of formula (III-b), a stereoisomer thereof and a pharmaceutically acceptable salt thereof, (I-a)
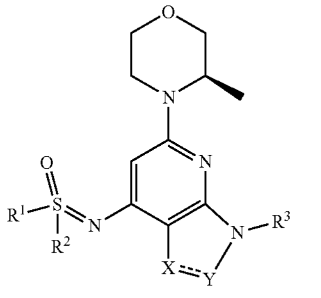
(I-b)
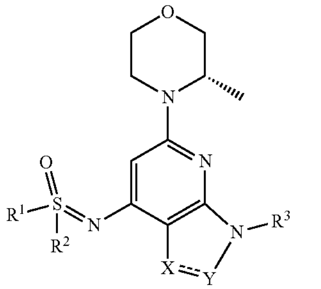
(II-a)
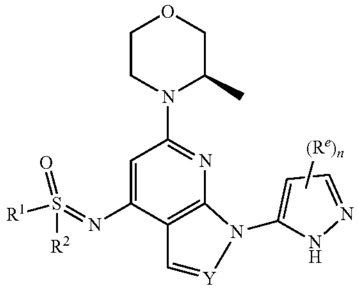
(II-b)
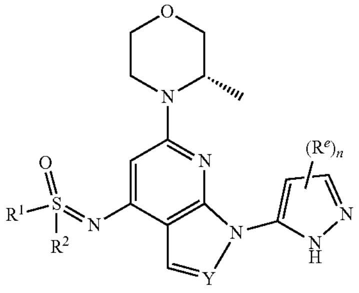
(III-a)
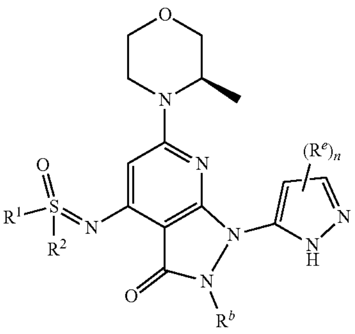
-continued
(III-b)
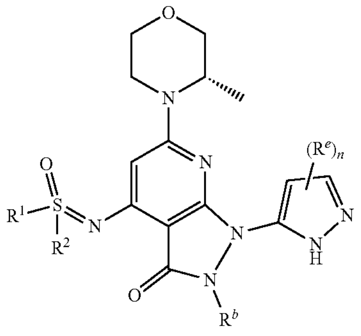
wherein
X, Y, $R^1$, $R^2$, $R^3$, $R^b$ and $R^e$ are as defined in claim 1;
n is selected from the group consisting of 0, 1 and 2.
13. A compound of Formula (I) a stereoisomer thereof or a pharmaceutically acceptable salt thereof according to claim 1, wherein the compound of Formula (I) is selected from the group consisting of:
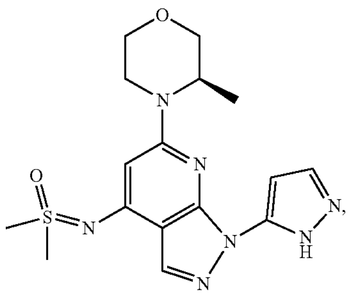
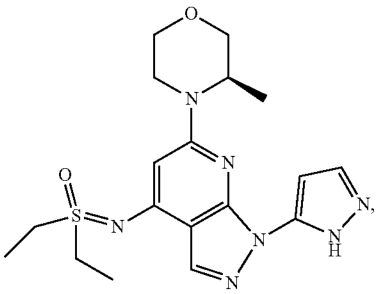
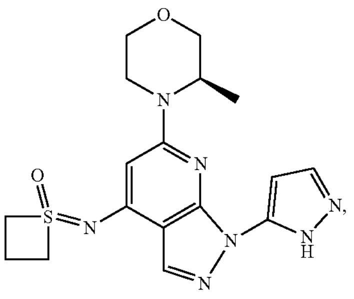

-continued
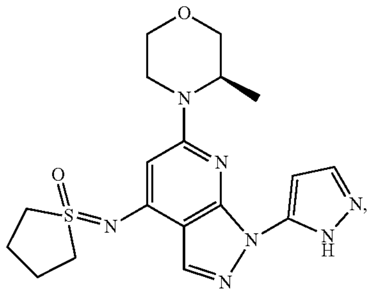
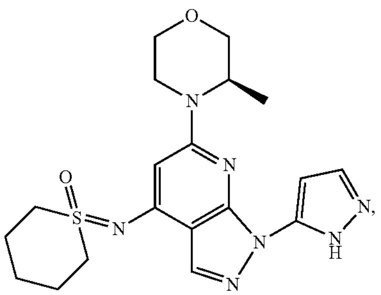
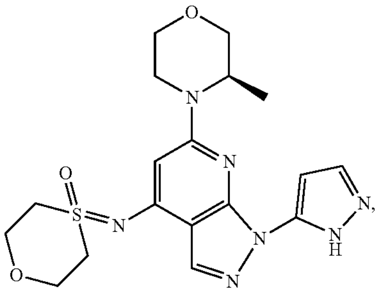
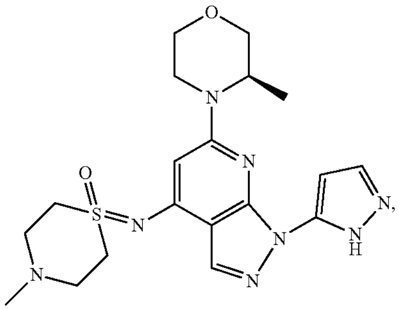
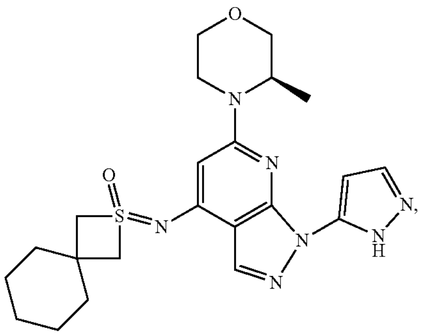
-continued
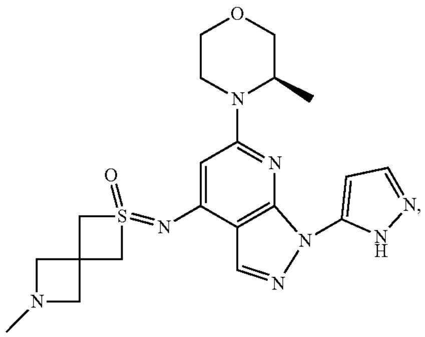
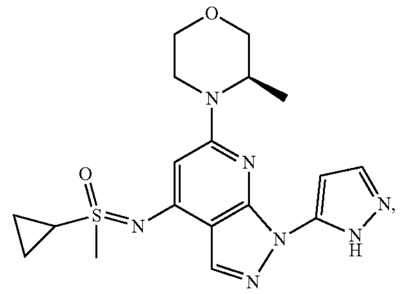
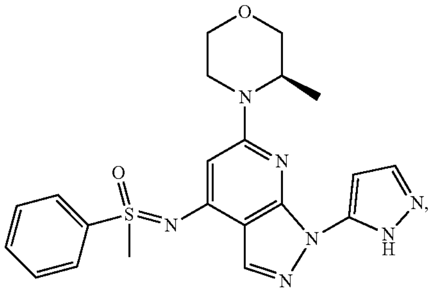
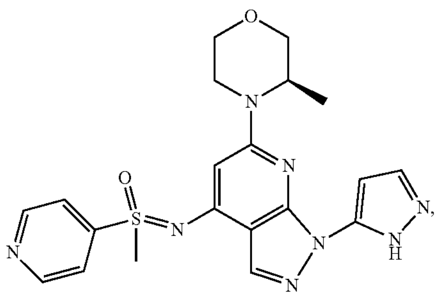
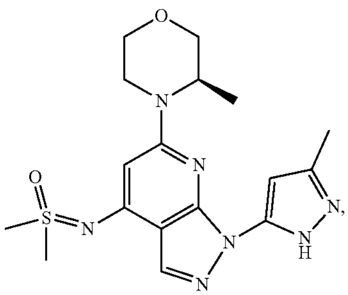

-continued
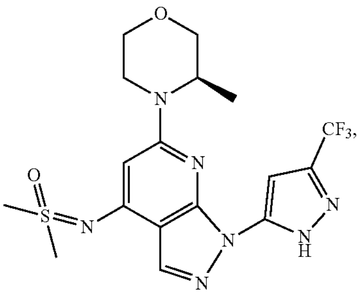
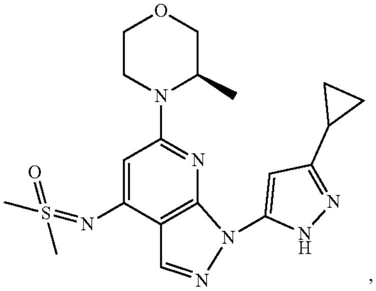
,
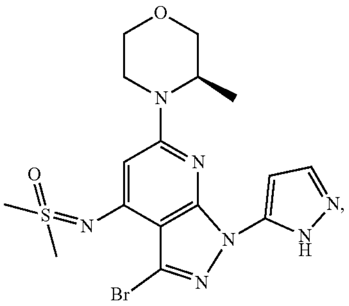
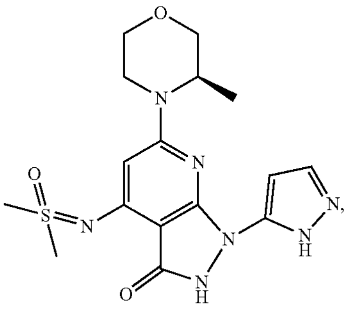
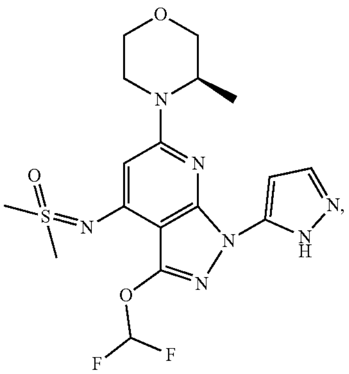
-continued
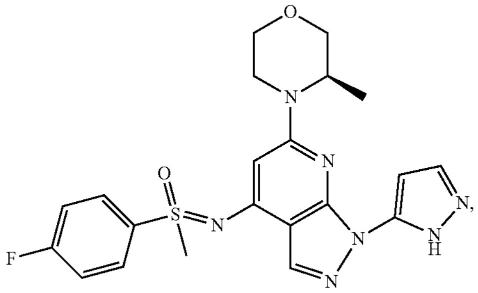
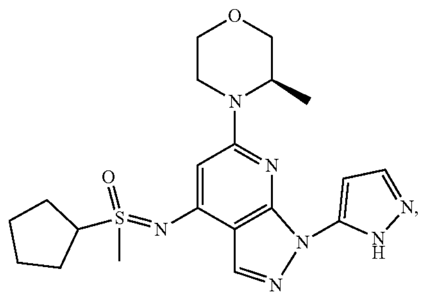
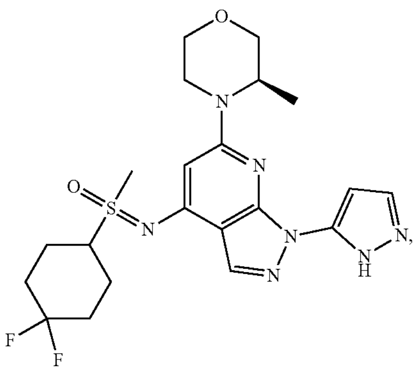
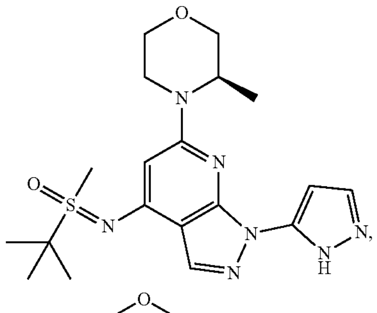
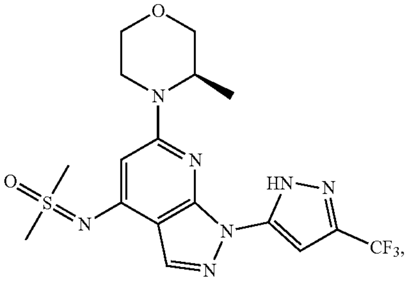

-continued
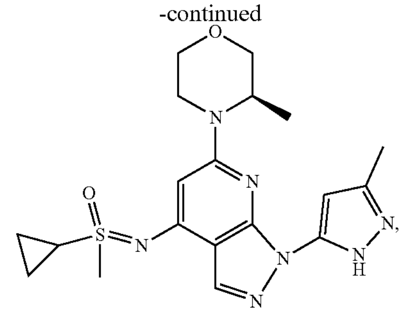
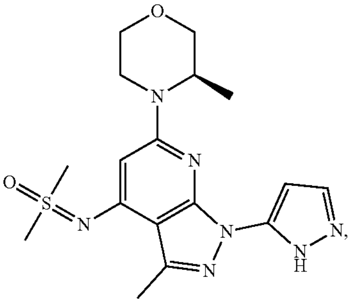
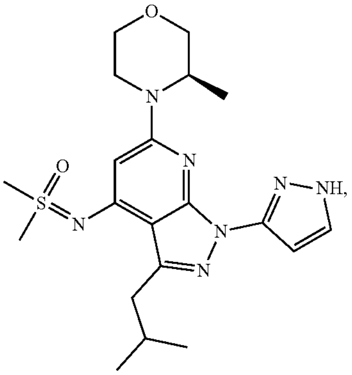
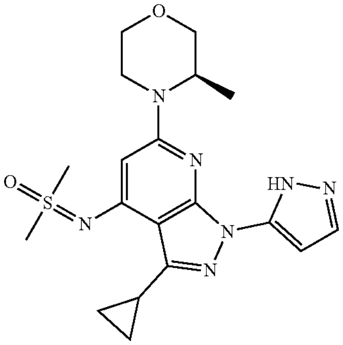
,
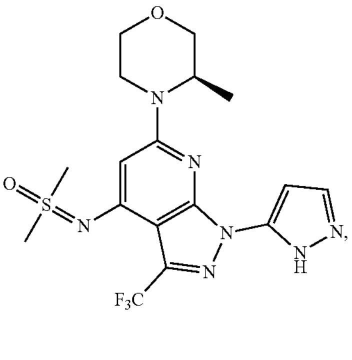
-continued
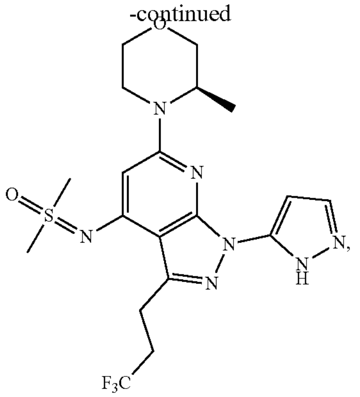
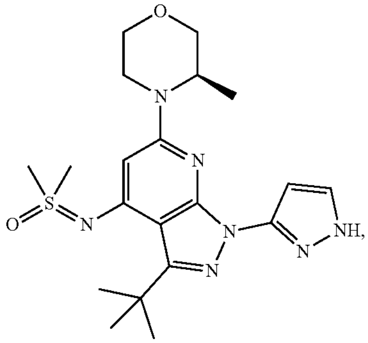
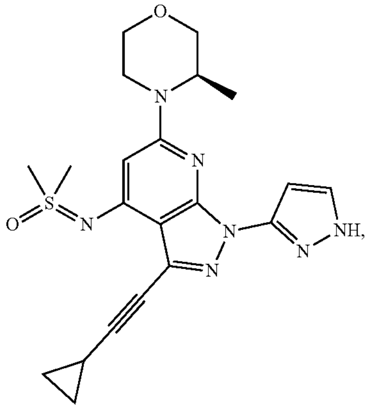
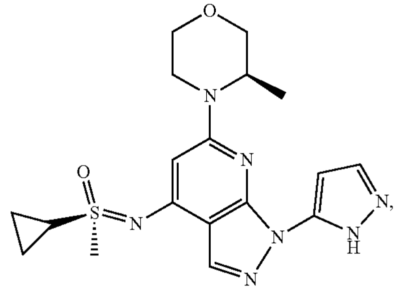
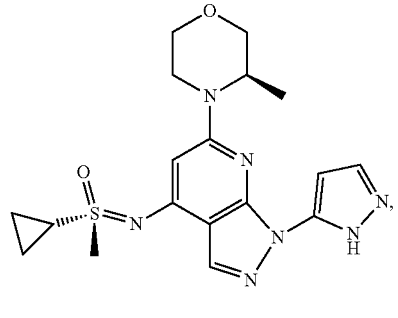

-continued
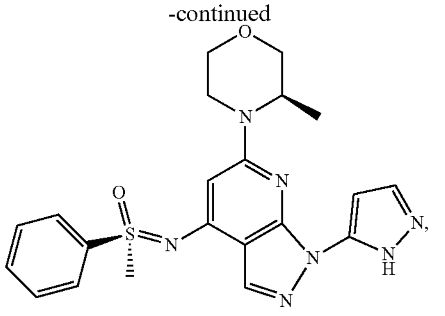,
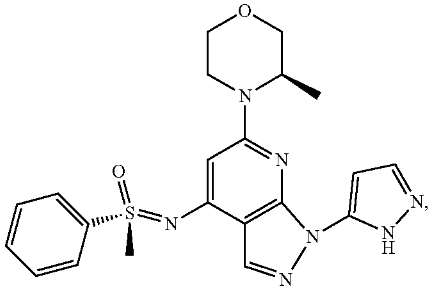,
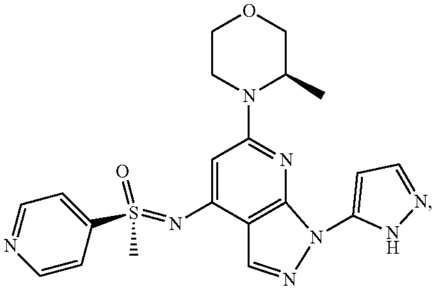,
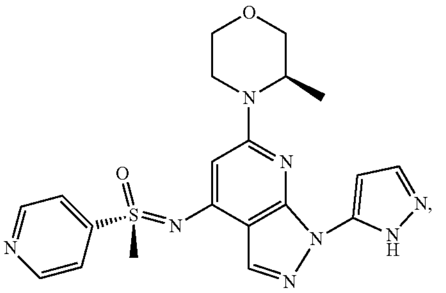,
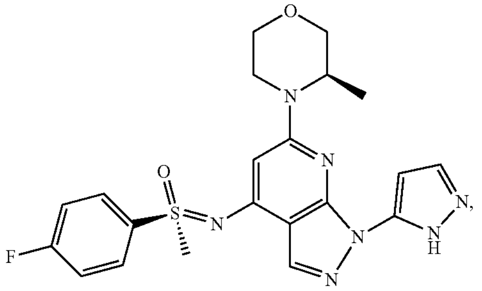,
-continued
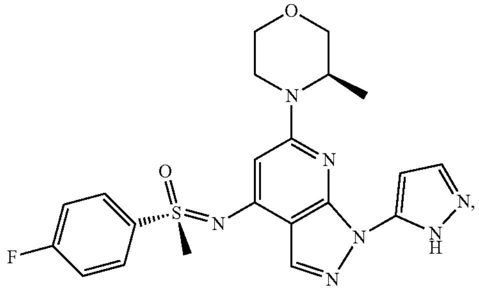,
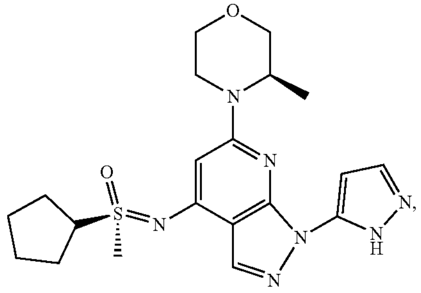,
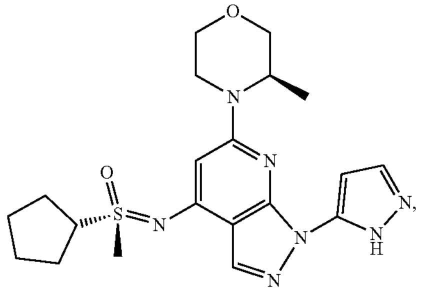,
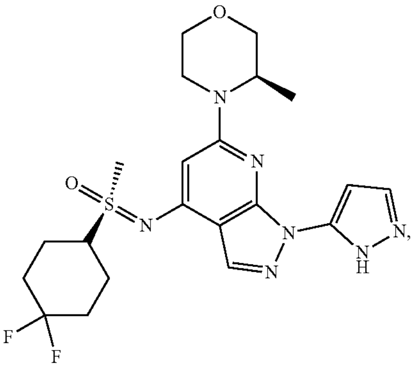,
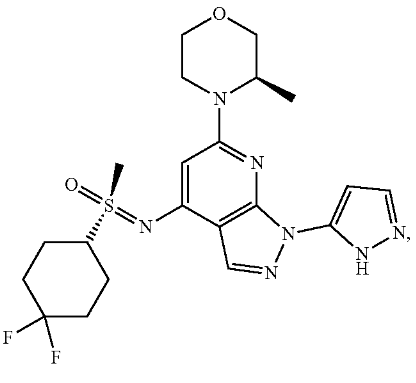, -continued

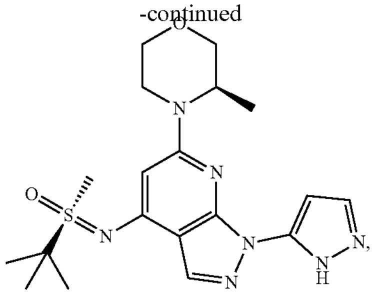

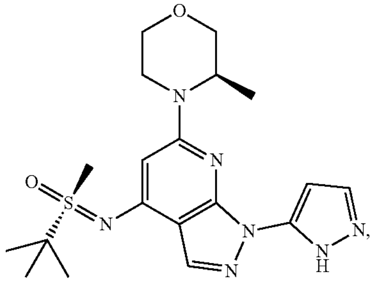

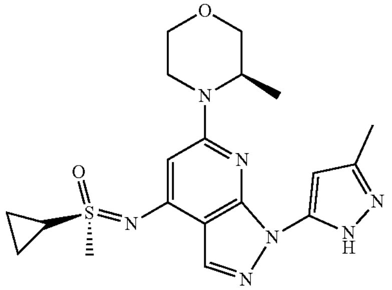

and

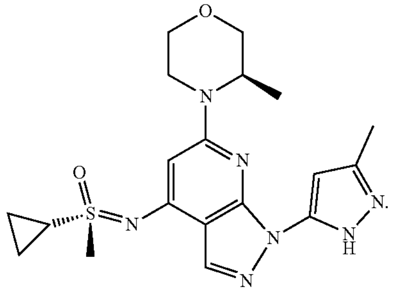

14. A pharmaceutical composition comprising the compound, the stereoisomer thereof or the pharmaceutically acceptable salt thereof according to claim 1.

15. The compound according to claim 6, wherein the structural unit

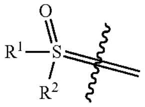

is selected from the group consisting of

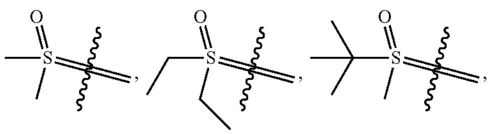

-continued

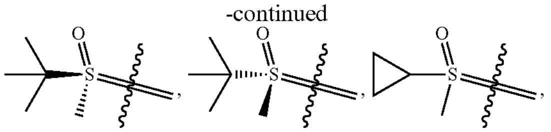

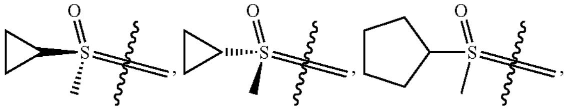

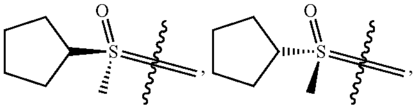

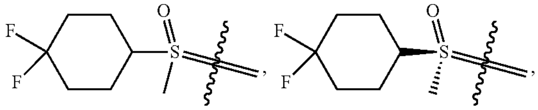

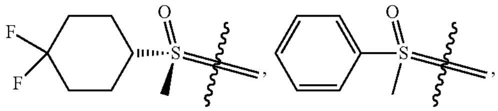

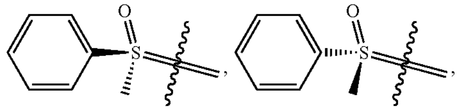

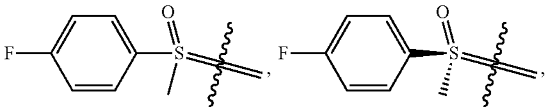

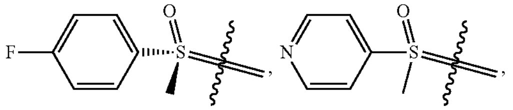

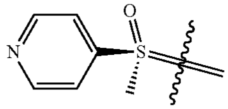

and

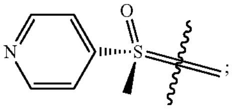

;

optionally, the structural unit

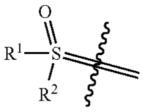

is selected from the group consisting of

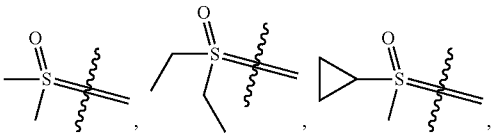

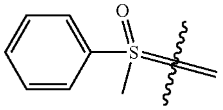

and

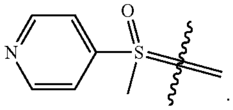

.

16. The compound according to claim 1, wherein $R^c$ is selected from the group consisting of halogen, hydroxy, amino, $C_{1-3}$ alkyl, $C_{1-3}$ alkoxy, $C_{1-3}$ alkyl-C(O)— and $C_{1-3}$ alkyl-$S(O)_2$—;

or $R^c$ is selected from the group consisting of halogen, hydroxy and amino;

or $R^c$ is selected from the group consisting of fluorine, chlorine and bromine;

or $R^c$ is selected from bromine.

17. The compound according to claim 1, wherein $R^d$ is selected from the group consisting of halogen, hydroxy, amino, $C_{1-3}$ alkyl, $C_{1-3}$ alkoxy, $C_{1-3}$ alkyl-C(O)—, $C_{1-3}$ alkyl-$S(O)_2$—, $C_{3-6}$ cycloalkyl, 3-6 membered heterocycloalkyl, phenyl and 5-6 membered heteroaryl;

or $R^d$ is selected from the group consisting of halogen, hydroxy, amino, $C_{1-3}$ alkyl and $C_{1-3}$ alkoxy;

or $R^d$ is selected from the group consisting of $C_{1-3}$ alkyl and $C_{1-3}$ alkoxy;

optionally, $R^d$ is selected from $C_{1-6}$ alkyl;

or $R^d$ is selected from $C_{1-3}$ alkyl;

or $R^d$ is selected from the group consisting of methyl, ethyl, n-propyl and isopropyl;

or $R^d$ is selected from methyl.

18. The compound according to claim 8, wherein $R^1$ and $R^2$ are each independently selected from the group consisting of methyl, ethyl, tert-butyl, cyclopropyl, cyclopentyl, cyclohexyl, phenyl and

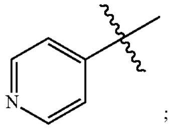

;

or $R^1$ and $R^2$, together with the sulfur atom to which they are attached, form

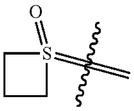
,
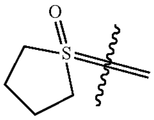
,
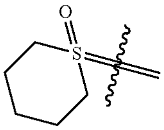
,
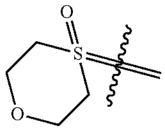
,
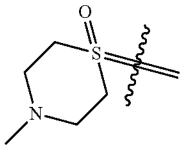
,
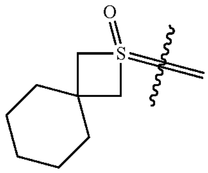
and
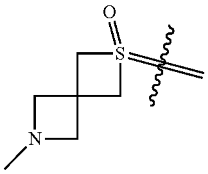
.

19. A method for treating an ATR-related or ATR-mediated disease and/or disorder, comprising administering an effective amount of the compound of Formula (I), the stereoisomer thereof or the pharmaceutically acceptable salt thereof according to claim 1 to a subject in need thereof, wherein the ATR-related or ATR-mediated disease and/or disorder is optionally a hyperproliferative disease.

* * * * *